US012421517B2

(12) United States Patent
Blurton-Jones et al.

(10) Patent No.: US 12,421,517 B2
(45) Date of Patent: Sep. 23, 2025

(54) GENETIC MODIFICATION OF MAMMALIAN CELLS TO CONFER RESISTANCE TO CSF1R ANTAGONISTS

(71) Applicant: THE REGENTS OF THE UNIVERSITY OF CALIFORNIA, Oakland, CA (US)

(72) Inventors: Mathew Blurton-Jones, Irvine, CA (US); Jean Paul Chadarevian, Irvine, CA (US); Robert Spitale, Irvine, CA (US); Sunil Gandhi, Irvine, CA (US); Whitney England, Irvine, CA (US); Hayk Davtyan, Irvine, CA (US); Jonathan Hasselmann, Irvine, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 18/069,543

(22) Filed: Dec. 21, 2022

(65) Prior Publication Data
US 2023/0203500 A1  Jun. 29, 2023

Related U.S. Application Data

(63) Continuation of application No. PCT/US2022/023139, filed on Apr. 1, 2022.

(60) Provisional application No. 63/236,951, filed on Aug. 25, 2021, provisional application No. 63/169,578, filed on Apr. 1, 2021.

(51) Int. Cl.
| | | |
|---|---|---|
| *C12N 15/113* | (2010.01) | |
| *A61K 9/00* | (2006.01) | |
| *A61K 31/4439* | (2006.01) | |
| *A61K 31/444* | (2006.01) | |
| *A61K 31/713* | (2006.01) | |
| *A61K 35/30* | (2015.01) | |
| *C07K 14/715* | (2006.01) | |

(52) U.S. Cl.
CPC ........ *C12N 15/1138* (2013.01); *A61K 9/0019* (2013.01); *A61K 31/4439* (2013.01); *A61K 31/444* (2013.01); *A61K 31/713* (2013.01); *A61K 35/30* (2013.01); *C07K 14/7153* (2013.01); *C12N 2310/14* (2013.01); *C12N 2320/32* (2013.01)

(58) Field of Classification Search
CPC .................. C12N 15/1138; C12N 2310/14
See application file for complete search history.

(56) References Cited

U.S. PATENT DOCUMENTS

| | | |
|---|---|---|
| 9,044,503 B2 | 6/2015 | Hersh et al. |
| 9,192,631 B2 | 11/2015 | Neumann et al. |
| 9,487,752 B2 | 11/2016 | Meyer et al. |
| 10,081,792 B2 | 9/2018 | Thomson et al. |
| 10,106,775 B2 | 10/2018 | Kato et al. |
| 10,238,692 B2 | 3/2019 | Yang et al. |
| 10,724,003 B2 | 7/2020 | Lim et al. |
| 11,124,765 B2 | 9/2021 | Thomson et al. |
| 11,136,548 B2 | 10/2021 | Muffat et al. |
| 11,149,250 B2 | 10/2021 | Douvaras et al. |
| 11,473,057 B2 | 10/2022 | Saito |
| 2006/0216760 A1 | 9/2006 | Dieterich et al. |
| 2012/0107898 A1 | 5/2012 | Neumann et al. |
| 2012/0135051 A1 | 5/2012 | Chien et al. |
| 2016/0186137 A1 | 6/2016 | Thomson et al. |
| 2016/0186146 A1 | 6/2016 | Thomson et al. |
| 2017/0253856 A1 | 9/2017 | Douvaras et al. |
| 2017/0369904 A1 | 12/2017 | Lim et al. |
| 2018/0179494 A1 | 6/2018 | Muffat et al. |
| 2020/0038439 A1 | 2/2020 | Biffi et al. |
| 2020/0239844 A1 | 7/2020 | Blurton-Jones et al. |
| 2020/0316039 A1 | 10/2020 | Filiano et al. |
| 2020/0390857 A1 | 12/2020 | Kay et al. |

(Continued)

FOREIGN PATENT DOCUMENTS

| | | |
|---|---|---|
| CA | 3054730 A1 | 9/2018 |
| EP | 2249861 B1 | 7/2016 |

(Continued)

OTHER PUBLICATIONS

Stanley, E. Richard, and Violeta Chitu. "CSF-1 receptor signaling in myeloid cells." Cold Spring Harbor perspectives in biology 6.6 (2014): a021857.

(Continued)

*Primary Examiner* — J. E. Angell
(74) *Attorney, Agent, or Firm* — NGUYEN TARBET IP LAW

(57) ABSTRACT

Microglia/monocytes exist within a 'niche' which limits the total number of microglia/monocytes/macrophages that reside within a mammalian central nervous system (CNS). Therefore, methods are needed that can help therapeutically modify microglia, monocytes, and macrophages or the cells that give rise to them to compete with endogenous microglia and partially or completely occupy the CNS niche. The present disclosure features therapeutic microglia, monocytes, or macrophages that have a selective advantage in comparison to endogenous brain resident microglia in their response to CSF1R inhibitors. Specifically, therapeutic cells developed in the present disclosure do not die at a given dose of CSF1R inhibitor that is sufficient to kill endogenous microglia. The therapeutic cells described herein can be used to treat neurological diseases.

24 Claims, 18 Drawing Sheets

Figure 2D:
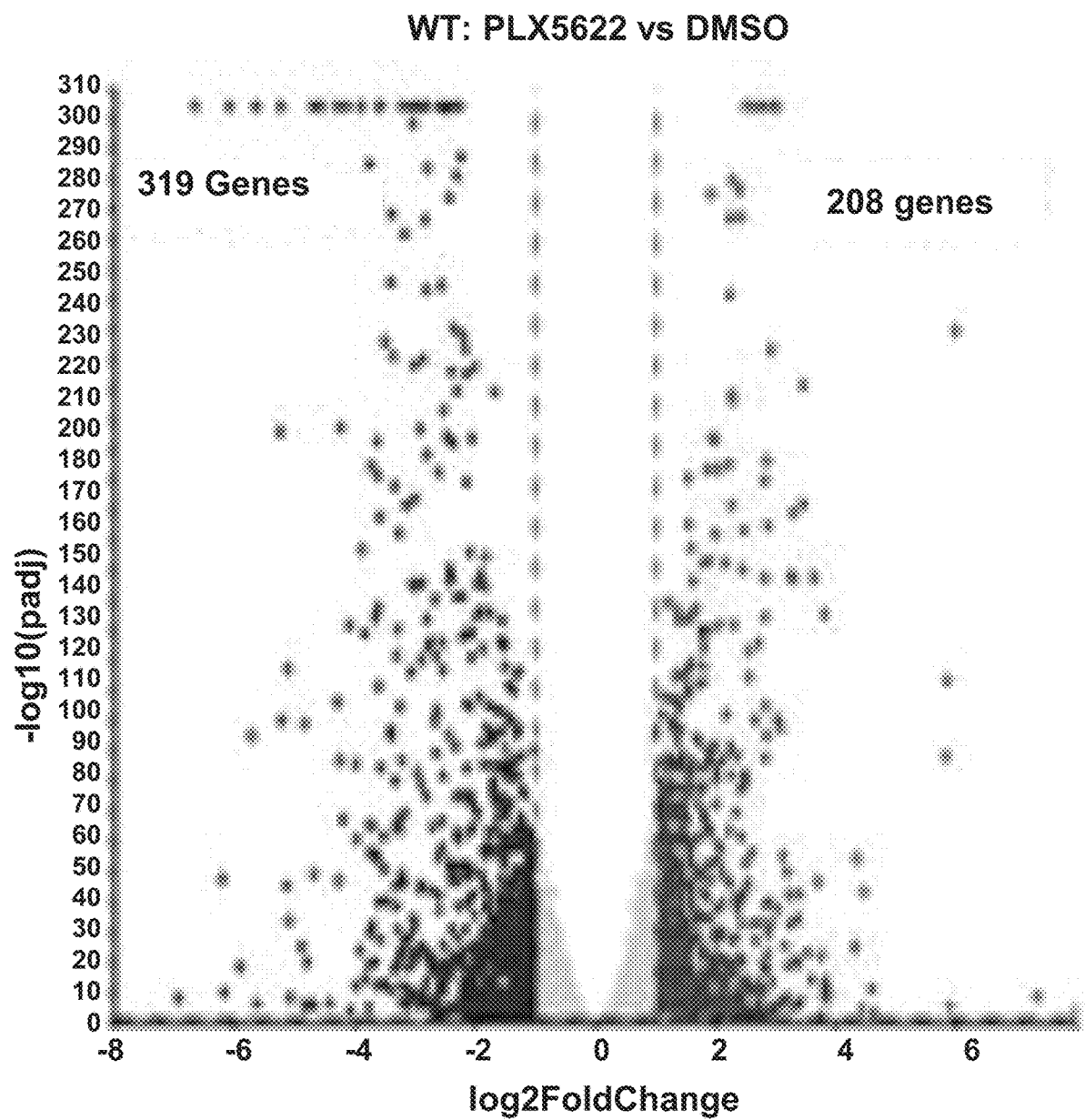

Specification includes a Sequence Listing.

(56) References Cited

U.S. PATENT DOCUMENTS

| | | |
|---|---|---|
| 2020/0399601 A1 | 12/2020 | Lim et al. |
| 2021/0102174 A1 | 4/2021 | Chiou et al. |
| 2021/0214681 A1 | 7/2021 | Studer et al. |
| 2022/0033773 A1 | 2/2022 | Thomson et al. |
| 2022/0152115 A1 | 5/2022 | Zhang |
| 2022/0251516 A1 | 8/2022 | Rajesh et al. |
| 2022/0323503 A1 | 10/2022 | Biffi et al. |
| 2023/0081264 A1* | 3/2023 | Bennett .................. A61K 45/06 424/93.7 |
| 2023/0165906 A1 | 6/2023 | Hebert et al. |
| 2023/0203500 A1 | 6/2023 | Blurton-Jones et al. |
| 2023/0248775 A1 | 8/2023 | Blurton-Jones et al. |

FOREIGN PATENT DOCUMENTS

| | | |
|---|---|---|
| EP | 3423564 A1 | 1/2019 |
| EP | 3589293 A1 | 1/2020 |
| EP | 4142745 A1 | 3/2023 |
| JP | 2020513794 A | 5/2020 |
| WO | WO-2004048549 A2 | 6/2004 |
| WO | 2009089635 A1 | 7/2009 |
| WO | 2016114723 A1 | 7/2016 |
| WO | 2016123100 A1 | 8/2016 |
| WO | 2016210313 A1 | 12/2016 |
| WO | 2018067826 A1 | 4/2018 |
| WO | 2018071898 A1 | 4/2018 |
| WO | 2018160496 A1 | 9/2018 |
| WO | 2019118951 A2 | 6/2019 |
| WO | 2020033791 A1 | 8/2019 |
| WO | 2020186237 A1 | 9/2020 |
| WO | 2020232512 A1 | 11/2020 |
| WO | 2021221879 A1 | 11/2021 |
| WO | 2021247710 A2 | 12/2021 |
| WO | 2022023773 A1 | 2/2022 |
| WO | 2022040798 A1 | 3/2022 |
| WO | 2022212897 A1 | 10/2022 |

OTHER PUBLICATIONS

Stephan et al., The Complement System: An Unexpected Role in Synaptic Pruning During Development and Disease, Annual Review of Neuroscience, vol. 35, pp. 369-389, 2012.
Sturgeon et al., Wnt Signaling Controls the Specification of Definitive and Primitive Hematopoiesis From Human Pluripotent Stem Cells, Nature Biotechnology, vol. 32, pp. 554-561, 2014.
TESR TM-E8TM: Feeder-free, animal component-free culture medium for maintenance of human ES and IPS cells. Stemcell Technologies, Version 4, 2 pages, 2021.
U.S. Appl. No. 16/489,338 Office Action dated Dec. 24, 2021.
U.S. Appl. No. 16/489,338 Office Action dated Jun. 30, 2022.
Villegas-Llerena et al., Microglial Genes Regulation Neuroinflammation in the Progression of Alzheimer's disease, Current Opinion in Neurobiology, vol. 36, pp. 74-81, 2015.
Vodyanik et al "Leukosialin (CD43) defines hematopoietic progenitors in human embryonic stem cell differentiation cultures," Blood, Sep. 15, 2006, 108:6.
Wang et al., IL-34 Is a Tissue-Restricted Ligand of CSF1 R Required for the Development of Langerhans Cells and Microglia, Nature Immunology, vol. 13, pp. 753-760, 2012.
Wang et al., Role of Pro-Inflammatory Cytokines Released From Microglia in Alzheimer's Disease, Annals of Translational Medicine, vol. 3, pp. 136, 2015.
Yamasaki et al., Differential Roles of Microglia and Monocytes in the Inflamed Central Nervous System, Journal of Experimental Medicine, vol. 211, pp. 1533-1549, 2014.
Yeh et al., TREM2 Binds to Apolipoproteins, Including APOE and CLU/APOJ, and Thereby Facilitates Uptake of Amyloid-Beta by Microglia, Neuron, vol. 91, pp. 328-340, 2016.
Zhang et al., An RNA-Sequencing Transcriptome and Splicing Database of Glia, Neurons, and Vascular Cells of the Cerebral Cortex, Journal of Neuroscience Research, vol. 34, pp. 11929-11947, 2014.
Chitu et al. "Emerging roles for CSF-1 receptor and its ligands in the nervous system." Trends in neurosciences 39.6 (2016): 378-393.
Etemad et al. "A novel in vitro human microglia model: characterization of human monocyte-derived microglia." Journal of neuroscience methods 209.1 (2012): 79-89.
Gupta et al. "Differentiation and characterization of myeloid cells." Current protocols in Immunology 104.1 (2014): 22F-5.
Heidel et al. "Clinical resistance to the kinase inhibitor PKC412 in acute myeloid leukemia by mutation of Asn-676 in the FLT3 tyrosine kinase domain." Blood 107.1 (2006): 293-300.
U.S. Appl. No. 16/566,675 Office Action Dated Mar. 1, 2023.
Tap et al. "Structure-guided blockade of CSF1R kinase in tenosynovial giant-cell tumor." New England Journal of Medicine 373.5 (2015): 428-437.
Yu et al. "Macrophage proliferation is regulated through CSF-1 receptor tyrosines 544, 559, and 807." Journal of Biological Chemistry 287.17 (2012): 13694-13704.
Hong et al., Complement and Microglia Mediate Early Synapse Loss in Alzheimer Mouse Models, Science, vol. 352, pp. 712-716, 2016.
Hong et al., New Insights on the Role of Microglia in Synaptic Pruning in Health and Disease, Current Opinion in Neurobiology, vol. 36, pp. 128-134, 2016.
International Preliminary Report on Patentability, mailed Sep. 9, 2019, in International Application No. PCT/US2018/019763.
International Search Report & Written Opinion, mailed Jul. 3, 2018, in International Application No. PCT/US2018/019763.
Karch et al., Alzheimer's Disease Risk Polymorphisms Regulate Gene Expression in the ZCWPW1 and the CELF1 Loci, PLoS One, vol. 11, No. e0148717, 2016.
Kennedy et al., Development of the Hemangioblast Defines the Onset of Hematopoiesis in HumanES Cell Differentiation Cultures, Blood, vol. 109, pp. 2679-2687, 2007.
Kessel, K.U., et al., Emergence of CD43-Expressing Hematopoietic Progenitors from Human Induced Pluripotent Stem Cells. Transfus Med Hemother 2017;44:143-150 DOI: 10.1159/000477357.
Kettenmann et al., Physiology of Microglia, Physiological Reviews, vol. 91, pp. 461-553, 2011.
Kierdorf et al., Factors regulating microglia activation, Frontier in Cellular Neuroscience, vol. 7, pp. 44, 2013.
Kierdorf et al., Microglia Emerge From Erythromyeloid Precursors Via Pu. 1-And Irf8-Dependent Pathways, Nature Neuroscience, vol. 16, pp. 273-280, 2013.
Koenigsknecht-Talboo et al., Microglial Phagocytosis Induced By Fibrillar Beta-Amyloid and Iggs are Differentially Regulated By Proinflammatory Cytokines, The Journal of Neuroscience, vol. 25, pp. 8240-8249, 2005.
Lancaster et al., Cerebral organoids model human brain development and microcephaly, Nature, vol. 501, pp. 373-379, 2013.
Lasagna-Reeves et al., Identification of Oligomers at Early Stages of Tau Aggregation in Alzheimer's Disease, The FASEB Journal, vol. 26, pp. 1946-1953, 2012.
Lavin et al., Tissue-resident Macrophage Enhancer Landscapes Are Shaped By the Local Microenvironment, Cell, vol. 159, pp. 1312-1326, 2014.
Li et al., RSEM: Accurate Transcript Quantification From RNA-Seq Data With or Without a Reference Genome, BMC Bioinformatics, vol. 12, pp. 323, 2011.
Linnartz-Gerlach et al., Sensing the Neuronal Glycocalyx By Glial Sialic Acid Binding Immunoglobulin-Like Lectins, Neuroscience, vol. 275, pp. 113-124, 2014.
Liu et al., CX3CR1 In Microglia Regulates Brain Amyloid Deposition Through Selective Protofibrillar Amyloid-Beta Phagocytosis, The Journal of Neuroscience, vol. 30, pp. 17091-17101, 2010.
Loo et al., *Apoptosis* Is Induced By Beta-Amyloid in Cultured Central Nervous System Neurons, Proceedings of the National Academy of Sciences of the United States of America, vol. 90, pp. 7951-7955, 1993.
Lui et al., Progranulin Deficiency Promotes Circuit-Specific Synaptic Pruning by Microglia via Complement Activation, Cell, vol. 165, pp. 921-935, 2016.
Marsh et al., The Adaptive Immune System Restrains Alzheimer's Disease Pathogenesis By Modulating Microglial Function, Proceed-

(56) References Cited

Figure 2E:
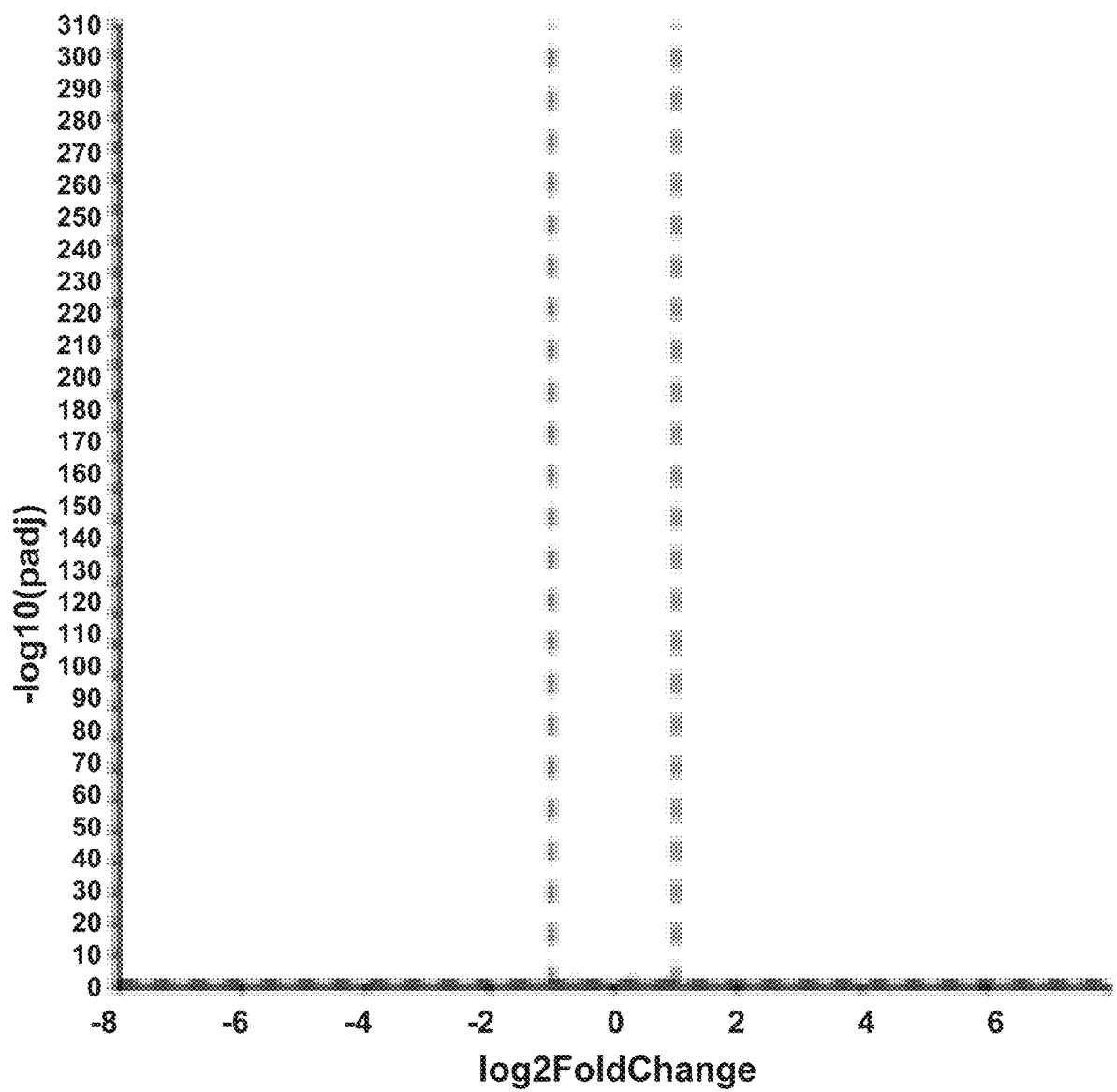
Figure 2F:
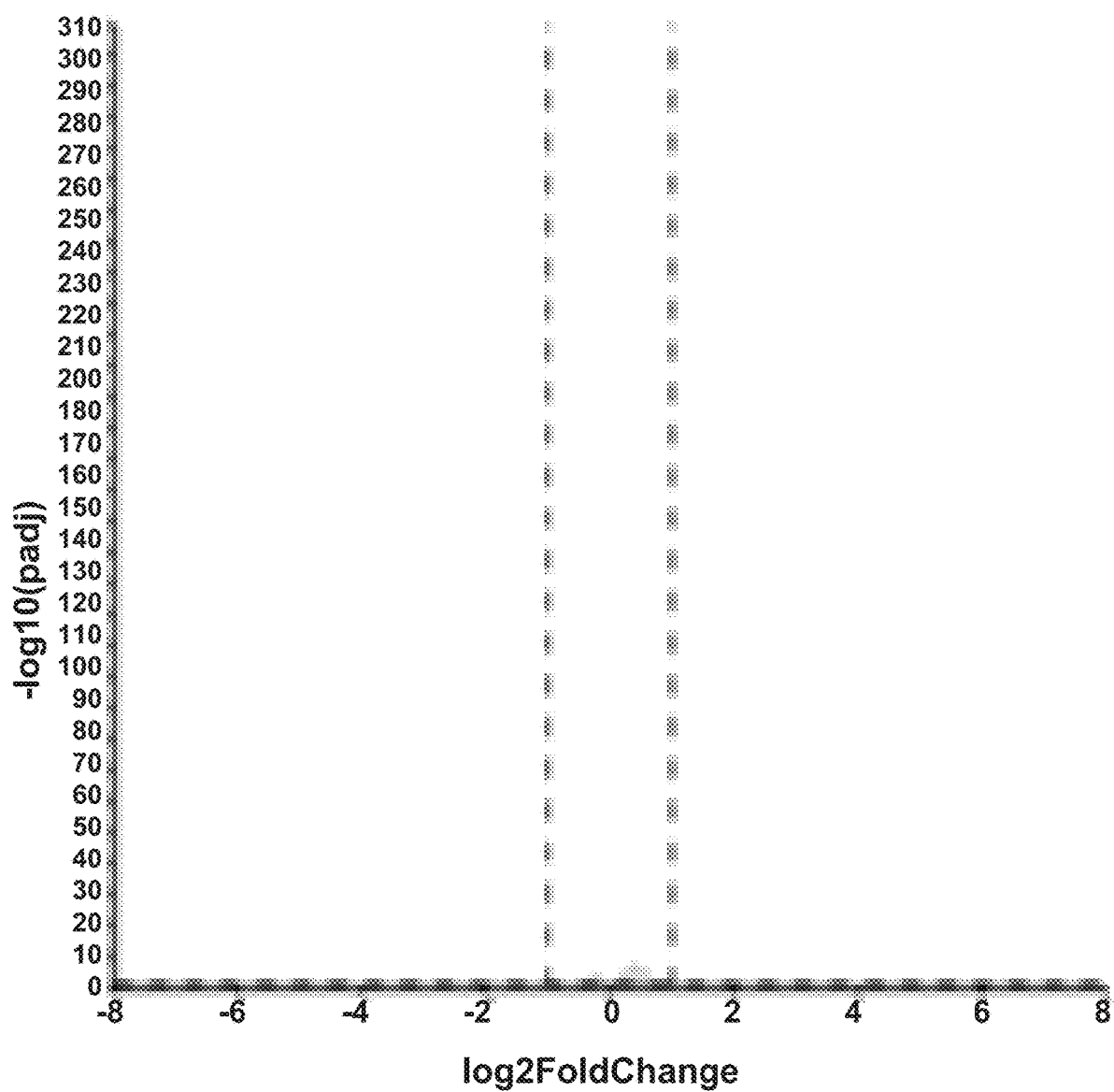

OTHER PUBLICATIONS ings of the National Academy of Sciences of the United States of America, vol. 113, pp. E1316-1325, 2016.
Matcovitch-Natan et al., Microglia Development Follows a Stepwise Program to Regulate Brain Homeostasis, Science, 353, aad8670, 2016.
McQuade, et al., Development and validation of a simplified method to generate human microglia from pluripotent stem cells, Molecular Neurodegeneration, vol. 13, No. 67, 2018.
Mildner et al., P2Y12 Receptor Is Expressed on Human Microglia Under Physiological Conditions Throughout Development and Is Sensitive to Neuroinflammatory Diseases, Glia, vol. 65, pp. 375-387, 2017.
Moore et al., P2Y12 Expression and Function in Alternatively Activated Human Microglia, Neurology Neuroimmunology & Neuroinflammation, vol. 2, No. e80, 2015.
Muffat et al., Efficient Derivation of Microglia-Like Cells From Human Pluripotent Stem Cells, Nature Medicine, 2016.
Nguyen et al. "A Bump-Hole Strategy for Increased Stringency of Cell-Specific Metabolic Labeling of RNA". ACS Chem. Biol., Nov. 21, 2020, vol. 15, No. 12, pp. 3099-3105, whole doc.
Nguyen et al. "Cell-Selective Bioorthogonal Metabolic Labeling of RNA". J. Am. (,hem. Soc. 2017, vol. 139, No. 6, pp. 2148-2151; abstract, Fig.2 Legand.
Office Action in Japanese Application No. 2019-546831 mailed Mar. 15, 2022.
Office Action in Japanese Application No. 2019-546831 mailed Sep. 13, 2022.
O'Rourke et al., C9orf72 Is Required for Proper Macrophage and Microglial Function in Mice, Science, vol. 351, pp. 1324-1329, 2016.
Pandya, et al., Differentiation of human murine induced pluripotent stem cells to microglia-like cells, Nature Neuroscience, vol. 20, No. 5, pp. 753-759, 2017.
Paolicelli et al., Synaptic Pruning By Microglia Is Necessary for Normal Brain Development, Science, vol. 333, pp. 1456-1458, 2011.
Patel et al., Inflammatory Cytokine Levels Correlate With Amyloid Load in Transgenic Mouse Models of Alzheimer's disease, Journal of Neuroinflammation, vol. 2, pp. 9, 2005.
PCT/US2021/035454 International Search Report and Written Opinion dated Dec. 21, 2021.
Prinz et al., Heterogeneity of CNS Myeloid Cells and Their Roles in Neurodegeneration, Nature Neuroscience, vol. 14, pp. 1227-1235, 2011.
Prinz et al., Microglia and Brain Macrophages in the Molecular Age: From Origin to Neuropsychiatric Disease, Nature Reviews Neuroscience, vol. 15, pp. 300-312, 2014.
Prinz et al., Tickets to the Brain: Role of CCR2 and CX3CR1 in Myeloid Cell Entry in the CNS, Journal of Neuroimmunology, vol. 224, pp. 80-84, 2010.
Product sheet CD200. Datasheet [Online]. Abeam/ no date. [retrieved on Dec. 13, 2021]. retrieved from the internet: www.abeam.com/recombi nant-human-cd200-ox2-protein-ab 152536 .html.
Product sheet human reombinant CX3CL 1, Data sheet [online]. Abeam, 2020 [retrived on Dec. 13, 2021]. retrieved from the internet: www .abcam.com/recombinant-human-cx3cl 1-protein-active-ab269216.html.
Rezaie et al., Colonisation of the Developing Human Brain and Spinal Cord By Microglia: A Review, Microscopy Research and Technique, vol. 45, pp. 359-382, 1999.
Robinson et al., edgeR: a Bioconductor Package for Differential Expression Analysis of Digital Gene Expression Data, Bioinformatics, vol. 26, pp. 139-140, 2010.
Rongvaux et al., Development and Function of Human Innate Immune Cells in a Humanized Mouse Model, Nature Biotechnology, vol. 32, pp. 364-372, 2014.
Rustenhoven et al., Isolation of Highly Enriched Primary Human Microglia for Functional Studies, Scientific Reports, vol. 6, pp. 19371, 2016.

Schilling et al., Astrocyte-released Cytokines Induce Ramification and Outward K + Channel Expression in Microglia Via Distinct Signaling Pathways, European Journal of Neuroscience, vol. 14, pp. 463-473, 2001.
Schulz et al., A Lineage of Myeloid Cells Independent of Myb and Hematopoietic Stem Cells, Science, vol. 336, pp. 86-90, 2012.
Shemer, et al. Engrafted parenchymal brain macrophages differ from microglia in transcriptome, chromatin landscape and response to challenge. Nat Commun. 2018; 9: 5206. Published online Dec. 6, 2018. doi: 10.1038/s41467-018-07548-5. bioRxiv (Jul. 16, 2018): 369942.
Shibuya, Y. et al., Treatment of a genetic brain disease by CNS-wide microglia replacement, Sci Transl Med. Mar. 16, 2022;14(636):eabl9945. doi: 10.1126/scitranslmed.ab19945. Epub Mar. 16, 2022.
Shulman et al., Functional Screening in Drosophila Identifies Alzheimer's Disease Susceptibility Genes and Implicates Tau-Mediated Mechanisms, Human Molecular Genetics, vol. 23, pp. 870-877, 2014.
Sirkis et al., Rare TREM2 Variants Associated With Alzheimer's Disease Display Reduced Cell Surface Expression, Acta Neuropathologica Communications, vol. 4, pp. 98, 2016.
Stalder et al., Invasion of Hematopoietic Cells Into the Brain of Amyloid Precursor Protein Transgenic Mice, the Journal of Neuroscience, vol. 25, pp. 11125-11132, 2005.
U.S. Appl. No. 16/566,675, OrbiMed Advisors LLC & Board of Tru.
Abbas et al., Up-regulation of the Inflammatory Cytokines IFN-gamma and IL-12 and Down-Regulation of IL-4 in Cerebral Cortex Regions of APP(SWE) Transgenic Mice, Journal of Neuroimmunology, vol. 126, DD. 50-57, 2002.
Abdollahi et al., Interferon Regulatory Factor 1 Is a Myeloid Differentiation Primary Response Gene Induced By Interleukin 6 and Leukemia Inhibitory Factor: Role in Growth Inhibition, Cell Growth and Differentiation, vol. 2, pp. 401-407, 1991.
Abud, E., Generation of Human Microglia from Induced Pluripotent Stem Cells to Study Innate Immunity in Neurological Diseases, Dissertation, Doctor of Philosophy, University of California, Irvine, 2017.
Abud, et al., iPSC-Derived Human Microglia-like Cells to Study Neurological Diseases, Neuron, vol. 94, No. 2, pp. 278-293,2017.
Abutbul et al., TGF-beta Signaling Through Smad2/3 Induces the Quiescent Microglial Phenotype Within the CNS Environment, Glia, 60, pp. 1160-1171, 2012.
Aguzzi et al., Microglia: Scapegoat, Saboteur, or Something Else?, Science, vol. 339, pp. 156-161, 2013.
Andreasson et al., Targeting Innate Immunity for Neurodegenerative Disorders of the Central Nervous System, Journal of Neurochemistry, vol. 138, pp. 653-693, 2016.
Asai et al., Depletion of Microglia and Inhibition of Exosome Synthesis Halt Tau Propagation, Nature Neuroscience, vol. 18, pp. 1584-1593, 2015.
Bachstetter et al., Disease-Related Microglia Heterogeneity in the Hippocampus of Alzheimer's Disease, Dementia With Lewy Bodies, and Hippocampal Sclerosis of Aging, Acta Neuropathologica Communications, vol. 3, pp. 32, 2015.
Baron et al., Accelerated Microglial Pathology Is Associated With Abeta Plaques in Mouse Models of Alzheimer's Disease, Aging Cell, vol. 13, pp. 584-595, 2014.
Bennett et al., New Tools for Studying Microglia in the Mouse and Human CNS, Proceedings of the National Academy of Sciences of the United States of America U SA, vol. 113, pp. E1738-1746, 2016.
Bennett, M. et al., The influence of environment and origin on brain resident macrophages and implications for therapy. Nature Neuroscience | vol. 23 | Feb. 2020 | 157-166 | www.nature.com/natureneuroscience.
Biber et al., Central Nervous System Myeloid Cells as Drug Targets: Current Status and Translational Challenges, Nature Reviews Drug Discovery, vol. 15, pp. 110-124, 2016.
Biber et al., Neuronal 'On' and 'Off' Signals Control Microglia, Trends in Neurosciences, vol. 30, pp. 596-602, 2007.
Blum-Degen et al., Interleukin-1 Beta and Interleukin-6 are Elevated in the Cerebrospinal Fluid of Alzheimer's and De Novo Parkinson's Disease Patients, Neuroscience Letters, vol. 202, pp. 17-20, 1995.

(56) References Cited

OTHER PUBLICATIONS

Blurton-Jones et al., Neural stem cells improve cognition via BDNF in a transgenic model of Alzheimer disease, Proc Natl Acad Sci U S A., vol. 106, No. 32, pp. 13594-13599, 2009.

Bradshaw et al., CD33 Alzheimer's Disease Locus: Altered Monocyte Function and Amyloid Biology, Nature Neuroscience, vol. 16, pp. 848-850, 2013.

Butovsky et al., Identification of a Unique TGF-Beta-Dependent Molecular and Functional Signature in Microglia, Nature Neurosciences, vol. 17, pp. 131-143, 2014.

Capotondo, A. et al., Brain conditioning is instrumental for successful microglia reconstitution following hematopoietic stem cell transplantation. PNAS, Sep. 11, 2012, vol. 109,No. 37; pp. 15018-15023.

Capotondo, A. et al., Intracerebroventricular delivery of hematopoietic progenitors results in rapid and robust engraftment of microglia-like cells. Sci. Adv. 2017;3: e1701211.

Chan et al., The Origin and Cell Lineage of Microglia: New Concepts, Brain Research Reviews, vol. 53, pp. 344-354, 2007.

Choi, Kyung-Dal et al., Hematopoietic and Endothelial Differentiation of Human Induced Pluripotent Stem Cells. Stem Cells. Mar. 2009 ; 27(3): 559-567. doi:10.1634/stemcells.2008-0922.

Choi, Kyung-Dal et al., Hematopoietic differentiation and production of mature myeloid cells from human pluripotent stem cells. Nature Protocols, Feb. 17, 2011, vol. 6 No. 3. pp. 296-313.

Chung et al., Astrocytes Mediate Synapse Elimination Through MEGF10 and MERTK pathways, Nature, vol. 504, pp. 394-400, 2013.

Communication Pursuant to Article 94(3) EPC in EP Application No. 18760945.8 dated Dec. 9, 2022.

Cronk, J.C. et al., Peripherally derived macrophages can engraft the brain independent of irradiation and maintain an identity distinct from microglia.J. Exp. Med. 2018 vol. 215 No. 6 1627-1647.

Crotti et al., Mutant Huntingtin Promotes Autonomous Microglia Activation Via Myeloid Lineage-Determining Factors, Nature Neuroscience, vol. 17, pp. 513-521, 2014.

De Simone et al., TGF-beta and LPS modulate ADP-Induced Migration of Microglial Cells Through P2Y1 and P2Y12 Receptor Expression, Journal of Neurochemistry, vol. 115, pp. 450-459, 2010.

Dobin et al., STAR: Ultrafast Universal RNA-seq Aligner, Bioinformatics, vol. 29, pp. 15-21, 2013.

Dorn, I. et al., Erythroid differentiation of human induced pluripotent stem cells is independent of donor cell type of origin. Haematologica, 2015; 100(1). pp. 32-41.

Durafourt et al., Isolation, Culturing, and Polarizing Primary Human Adult and Fetal Microglia, Methods in Molecular Biology, vol. 1041, pp. 199-211, 2013.

Erny et al., Host Microbiota Constantly Control Maturation and Function of Microglia in the CNS, Nature Neuroscience, vol. 18, pp. 965-977, 2015.

Extended European Search Report, dated Nov. 18, 2020, in Application No. 18760945.8.

Fu et al., ABSA7 Mediates Phagocytic Clearance of Amyloid-beta in the Brain, Journal of Alzheimer's Disease, vol. 54, pp. 569-584, 2016.

Gay et al. "Mouse TU tagging: a chemical/genetic intersectional method for purifying cell type-specific nascent RNA". Genes & Development, Jan. 1, 2013, vol. 27, No. 1, pp. 98-115; abstract, p. 100, col. 2, para 2, p. 101, col. 1, para 3, p. 104, col. 1, para 3, p. 108, col. 2, para 2.

Ghosh et al. "UPRT, a suicide-gene therapy candidate in higher eukaryotes, is required for *Drosophila* larvalgrowth and normal adult lifespan". Scientific Reports, Aug. 24, 2015, vol. 5, article 13176 (pp. 1-11 ); abstract, p. 5, para 1, p. 6, para 3.

Ginhoux et al., Fate Mapping Analysis Reveals That Adult Microglia Derive From Primitive Macrophages, Science, vol. 330, pp. 841-845, 2010.

Glass et al., Molecular Control of Activation and Priming in Macrophages, Nature Immunology, vol. 17, pp. 26-33, 2016.

Gosselin et al., Environment Drives Selection and Function of Enhancers Controlling Tissue-Specific Macrophage Identities, Cell, vol. 159, pp. 1327-1340, 2014.

Grabert et al., Microglial Brain Region-Dependent Diversity and Selective Regional Sensitivities to Aging, Nature Neuroscience, vol. 19, pp. 504-516, 2016.

Greer et al., A Family of non-GPCR Chemosensors Defines an Alternative Logic for Mammalian Olfaction, Cell, vol. 165, pp. 1734-1748, 2016.

Greter et al., Strama-Derived Interleukin-34 Controls the Development and Maintenance of Langerhans Cells and the Maintenance of Microglia, Immunity, vol. 37, pp. 1050-1060, 2012.

Guillot-Sestier et al., Innate immunity in Alzheimer's disease: a complex affair, CNS & Neurological Disorders-Drug Targets, vol. 12, pp. 593-607, 2013.

Gyl Ys et al., Quantitative Characterization of Crude Synaptosomal Fraction (P-2) Components By Flow Cytometry, Journal of Neuroscience Research, vol. 61, pp. 186-192, 2000.

Haney et al. "Genetically modified macrophages accomplish targeted gene delivery to the inflamed brain in transgenic Parkin Q311X (A) mice: importance of administration routes." Scientific reports 10.1 (2020): 1-13.

Hanna et al., The transcription factor NR4A1 (Nur77) Controls Bone Marrow Differentiation and the Survival of Ly6C-Monocytes, Nature Immunology, vol. 12 pp. 778-785, 2011.

Haynes et al., The P2Y12 Receptor Regulates Microglial Activation By Extracelluar Nucleotides, Nature Neuroscience, vol. 9, pp. 1512-1519, 2006.

Hickman et al., Microglial Dysfunction and Defective Beta-Amyloid Clearance Pathways in Aging Alzheimer's Disease Mice, The Journal of Neuroscience, vol. 28, pp. 8354-8360, 2008.

Hickman et al., The Microglial Sensome Revealed By Direct RNA Sequencing, Nature Neuroscience, vol. 16, pp. 1896-1905, 2013.

Hohsfield, L. A. et al., Effects of long-term and brain-wide colonization of peripheral bone marrow-derived myeloid cells in the CNS. J Neuroinflammation. Sep. 20, 2020;17(1):279. doi: 10.1186/s12974-020-01931-0.

Dräger et al. "A CRISPRi/a platform in human iPSC-derived microglia uncovers regulators of disease states." Nature neuroscience 25.9 (2022): 1149-1162.

Fong et al. "Genetic correction of tauopathy phenotypes in neurons derived from human induced pluripotent stem cells." Stem cell reports 1.3 (2013): 226-234.

Jiang et al. "Integrative system biology analyses of CRISPR-edited iPSC-derived neurons and human brains reveal deficiencies of presynaptic signaling in FTLD and PSP." Translational psychiatry 8.1 (2018): 265.

Kampmann, Martin. "CRISPR-based functional genomics for neurological disease." Nature Reviews Neurology 16.9 (2020): 465-480.

Ortiz-Virumbrales, Maitane, et al. "CRISPR/Cas9-Correctable mutation-related molecular and physiological phenotypes in iPSC-derived Alzheimer's PSEN2 N141I neurons." Acta neuropathologica communications 5 (2017): 1-20.

Xu et al. "Efficient strategies for microglia replacement in the central nervous system." Cell reports 32.6 (2020).

Wang et al. "CRISPR/Cas9-mediated targeted gene correction in amyotrophic lateral sclerosis patient iPSCs." Protein & Cell 8.5 (2017): 365-378.

Dulski et al. "Brain abnormalities, neurodegeneration, and dysosteosclerosis (BANDDOS): new cases, systematic literature review, and associations with CSF1R-ALSP." Orphanet Journal of Rare Diseases 18.1 (2023): 1-17.

Bennett, F. Chris, et al. "A combination of ontogeny and CNS environment establishes microglial identity." Neuron 98.6 (2018): 1170-1183.

Bruttger, et al.: Genetic Cell Ablation Reveals Clusters of Local Self-Renewing Microglia in the Mammalian Central Nervous System. Immunity. Jul. 21, 2015;43(1):92-106. doi: 10.1016/j.immuni.2015.06.012. Epub Jul. 7, 2015.

Buttgereit, et al.: Sall1 is a transcriptional regulator defining microglia identity and function. Nat Immunol. Dec. 2016;17(12):1397-1406. doi: 10.1038/ni.3585. Epub Oct. 24, 2016.

(56) References Cited

OTHER PUBLICATIONS

Capuccini et al.: Transcriptomic profiling of microglia reveals signatures of cell activation and immune response, during experimental cerebral malaria, Nature Scientific Reports 6:39258; Dec. 19, 2016.
Castro-Poceiro, Jesús et al.: Mesenchymal stromal cells in the treatment of perianal fistulas in Crohn's disease. Cell Report 24:1203-1217 (2018). DOI: 10.2217/imt-2018-0099 (abstract).
Cerami et al.: The cBio cancer genomics portal: an open platform for exploring multidimensional cancer genomics data. Cancer Discov. 2:401-404 (2012).
Chiu, et al.: A neurodegeneration-specific gene-expression signature of acutely isolated microglia from an amyotrophic lateral sclerosis mouse model. Cell Rep. 4:385-401 (2013).
Clarke, et al.: Normal aging induces A1-like astrocyte reactivity. Proc. Natl. Acad. Sci. USA 115:E1896-E1905 (2018).
Dai, et al.: Targeted disruption of the mouse col•ony-stimulating factor 1 receptor gene results in osteopetrosis, mononuclear phagocyte deficiency, increased primitive progenitor cell frequencies, and reproductive defects. Blood 99:111-120 (2002).
Davalos, et al. ATP mediates rapid microglial response to local brain injury in vivo. Nat Neurosci. Jun. 2005; 8(6):752-8. Epub May 15, 2005.
De Chaumont, et al.: Icy: an open bioimage informatics platform for extended repr••ducible research. Nat. Methods 9, 690-696 (2012).
Dzenko, et al.: The chemokine receptor CCR2 mediates the binding and internalization of mono-cyte chemoattractant protein-1 along brain microvessels. J. Neurosci. 21, 9214-9223 (2001).
Elmore, Monica Renee Pittman et al.: CSF1 receptor signaling is necessary for microglia viability, which unmasks a cell that rapidly repopulates the microglia-depleted adult brain. Neuron. 82(2):380-397 (2014). doi: 10.1016/j.neuron.2014.02.040.
Escolar, et al.: Transplantation of umbilical-cord blood in babies with infantile Krabbe's disease. N Engl J Med. May 19, 2005;352(20):2069-81.
Filipello, et al.: The Microglial Innate Immune Receptor TREM2 Is Required for Synapse Elimination and Normal Brain Connectivity. Immunity. May 15, 2018;48(5):979-991.e8. doi: 10.1016/j.immuni.2018.04.016. Epub May 8, 2018.
Gomez Perdiguero, et al.: Tissue-resident macrophages originate from yolk-sac-derived erythro-myeloid progenitors. Nature 518:547-551 (2015).
Hagemeyer, et al.: Transcriptome-based profiling of yolk sac-derived macrophages reveals a role for Irf8 in macrophage maturation. EMBO J. 35:1730-1744 (2016).
Hammond, et al.: Complex cell-state changes revealed by single cell RNA sequencing of 76, 149 microglia throughout the mouse lifespan and in the injured brain. bioRxiv ( Aug. 31, 2018): 406140.
Han, Jinming et al.: Microglial replacement therapy: a potential therapeutic strategy for incurable CSF1R-related leukoencephalopathy. Acta Neuropathologica Communications 8:217 (2020).
Heng, et al.: Immunological Genome Project Consortium (2008). The Immunological Genome Project: networks of gene expression in immune cells. Nat. Immunol. 9, 1091-1094.
Hickman et al.: TREM2 and the neuroimmunology of Alzheimer's disease, Biochemical Pharmacology 88 (2014) 495-498.
Hoeffel, et al.: (2015). C-Myb(+) erythro-myeloid progenitor-derived fetal monocytes give rise to adult tissue-resident macr••phages. Immunity 42, 665-678.
Hollingworth, et al.: Alzheimer's Disease Neuroimaging Initiative; Charge consortium; EADI1 consortium (2011). Common variants at ABCA7, MS4A6A/MS4A4E, EPHA1 CD33 and CD2AP are associated with Alzheimer's disease. Nat. Genet. 43, 429-435.
Honda et al.: Extracellular ATP or ADP Induce Chemotaxis of Cultured Microglia through Gi/o-Coupled P2Y Receptors, The Journal of Neuroscience, Mar. 15, 2001, 21 (6):1975-1982.
Horlbeck, et al.: Compact and highly active next-generation libraries for CRISPR-mediated gene repression and activation. eLife. 2016; 5: e19760. Published online Sep. 23, 2016. doi: 10.7554/eLife. 19760.

Huang, et al.: Repopulated microglia are solely derived from the proliferation of residual microglia after acute depletion. Nat. Neurosci. 21, 530-540 (2018).
Koizumi et al.: Purinergic Receptors in Microglia: Functional Modal Shifts of Microglia Mediated by P2 and P1 Receptor. GLIA 61: 47-54 (2013).
Konno, et al.: Clinical and genetic characterization of adult-onset leukoencephalopathy with axonal spheroids and pigmented glia associated with CSF1R mutation. Eur J Neurol. Jan. 2017; 24(1): 37-45. Published online Sep. 29, 2016. doi: 10.1111/ene.13125.
Krasemann, et al.: The TREM2-APOE pathway drives the transcriptional phenotype of dysfunctional microglia in neurodegenerative diseases. Immunity 47:566-581.e9 (2017).
Lee et al.: Cytokines, Chemokines, and Cytokine Receptors in Human Microglia. Journal of Neuroscience Research 69:94-103 (2002).
Li, et al.: Conditional deletion of the colony stimulating factor-1 receptor (c-fms proto-oncogene) in mice. Genesis 44:328-335 (2006).
Li, et al.: Microglia and macrophages in brain homeost••sis and disease. Nat. Rev. Immunol. 18, 225-242 (2018).
Li, et al.: Developmental heterogeneity of microglia and brain myeloid cells revealed by deep single-cell RNA sequencing. bioRxiv (2018): 406363.
Liddelow, et al.: Neurotoxic reactive astrocytes are induced by activated micro-glia. Nature 541:481-487 (2017).
Lovly, et al.: Molecular Pathways: Resistance to Kinase Inhibitors and Implications for Therapeutic Strategies. Clin Cancer Res. May 1, 2014; 20(9): 2249-2256. doi: 10.1158/1078-0432.CCR-13-1610.
Maher, et al.: Cellular Transplant Therapies for Globoid Cell Leukodystrophy: Preclinical and Clinical Observations. J Neurosci Res. Nov. 2016; 94(11): 1180-1188. doi: 10.1002/jnr.23782.
Maier, et al.: ff14SB: Improving the accuracy of protein side chain and backbone parameters from ff99SB. J Chem Theory Comput. Aug. 11, 2015; 11(8): 3696-3713. Published online Jul. 23, 2015. doi: 10.1021/acs.jctc.5b00255.
Marques et al.: Microglial cells initiate vigorous yet non-protective immune responses during HSV-1 brain infection, Virus Research 121:1-10 (2006).
Mass, et al.: Specification of tissue-resident macrophages during organogenesis. Science 353, aaf4238 (2016).
Metsalu, et al.: ClustVis: a web tool for visualizing clustering of multivariate data using principal component analysis and heatmap. Nucleic Acids Res. 43 (W1), W566-70 (2015).
Mildner, et al.: Microglia in the adult brain arise from Ly-6ChiCCR2+ monocytes only under defined host co••ditions. Nat. Neurosci. 10, 1544-1553 (2007).
Morgens, et al.: Genome-scale measurement of off-target activity using Cas9 toxicity in high-throughput screens. Nat Commun. 8:15178 (2017). Published online May 5, 2017. doi: 10.1038/ncomms15178.
Obermeier, et al.: Development, maintenance and disruption of the blood-brain barrier. Nat. Med. 19:1584-1596 (2013).
Ohgidani, et al.: Direct induction of ramified microglia-like cells from human monocytes: dynamic mi-croglial dysfunction in Nasu-Hakola disease. Sci. Rep. 4:4957 (2014).
Phillips et al.: Scalable molecular dynamics with NAMD. J. Comp. Chem. 26.16 (2005): 1781-1802. doi: 10.1002/jcc.20289.
Priller, et al.: Targeting gene-modified hematopoietic cells to the central nervous system: use of green fluorescent protein uncovers microglial engraftment. Nat. Med. 7:1356-1361 (2001).
Prokop et al.: Microglia actions in Alzheimer's disease. Acta Neuropathol 126:461-477 (2013).
Qian, et al.: Brain Region-specific Organoids using Mini-bioreactors for Modeling ZIKV Exposure. Cell. May 19, 2016; 165(5): 1238-1254. Published online Apr. 22, 2016. doi: 10.1016/j.cell.2016.04.032.
Rathinam, et al.: Efficient differentiation and function of human macrophages in hu•manized CSF-1 mice. Blood 118:3119-3128 (2011).
Rock et al: Transcriptional response of human microglial cells to interferon-g. Genes and Immunity 6:712-719 (2005).

(56) References Cited

OTHER PUBLICATIONS

Saederup, et al.: Selective chemokine receptor usage by central nervous system myeloid cells in CCR2-red fluorescent protein knock-in mice. PLoS ONE5, e13693 (2010).
Schuberth, M., et al. "Hereditäre diffuse Leukenzephalopathie mit Sphäroiden: Eine Mikrogliopathie durch Fehlfunktion des CSF1-Rezeptors (Originalien)." Der Nervenarzt 85.4 (2014): 465-470.
Examination Report under Section 18(3) dated Sep. 25, 2023 for corresponding GB patent application GB2219686.9.
Office Action dated Nov. 23, 2021 for German Utility Model Patent Application 20 2022 002 866.0.
Sarter, Martin. "Animal cognition: defining the issues." Neuroscience & Biobehavioral Reviews 28.7 (2004): 645-650.
Anger, W. Kent. "Animal test systems to study behavioral dysfunctions of neurodegenerative disorders." Neurotoxicology 12.3 (1991): 403-413.
Tayebati, Seyed Khosrow. "Animal models of cognitive dysfunction." Mechanisms of ageing and development 127.2 (2006): 100-108.
Cuadros et al. "Microglia and microglia-like cells: similar but different." Frontiers in cellular neuroscience 16 (2022): 816439.
Clayton et al. "Plaque associated microglia hyper-secrete extracellular vesicles and accelerate tau propagation in a humanized APP mouse model." Molecular neurodegeneration 16 (2021): 1-16.
International Search Report and Written Opinion for PCT/US23/66323 dated Aug. 5, 2024.
A Public Health Approach to Alzheimer's and Other Dementias Module 1: Alzheimer's Disease as a Public Health Crisis. Alzheimer's Association—Centers for Disease Control and Prevention. Date unknown.
Ajami, et al.: Infiltrating monocytes trigger EAE progression, but do not contribute to the resident microglia pool. Nat Neurosci. Jul. 31, 2011;14(9):1142-9. doi: 10.1038/nn.2887.
Ajami, et al.: Local self-renewal can sustain CNS microglia maintenance and function throughout adult life. Nat Neurosci. Dec. 2007;10(12):1538-43. Epub Nov. 18, 2007.
Bain, et al.: Constant replenishment from circulating monocytes maintains the macrophage pool in adult intestine. Nat Immunol. Oct. 2014; 15(10): 929-937.
Barbato, Angelo.: Nations for mental health: Schizophrenia and public health. Geneva: World Health Organization Division of Mental Health and Prevention of Substance Abuse (MSA) (1998).
Bardou, et al.: jvenn: an interactive Venn diagram viewer. BMC Bioinformatics. 2014; 15(1): 293.
Berman, et al.: The protein data bank. Nucleic acids research 28.1 (2000): 235-242.
Biffi, A.: Hematopoietic Stem Cell Gene Therapy for Storage Disease: Current and New Indications. Mol Ther. May 3, 2017; 25(5): 1155-1162. Published online Apr. 4, 2017. doi: 10.1016/j.ymthe.2017.03.025.
Office Action dated Aug. 18, 2023 issued in U.S. Appl. No. 18/069,631.
Office Action dated Dec. 21, 2023 issued in U.S. Appl. No. 16/566,675.
Office Action dated Jan. 25, 2024 issued in U.S. Appl. No. 18/069,631.
Office Action dated Mar. 1, 2023 issued in U.S. Appl. No. 16/566,675.
PCT/US2022/023139 International Search Report and Written Opinion dated Aug. 30, 2022 (Publ. No. WO2022212897A1).
U.S. Appl. No. 16/489,338 Office Action dated Apr. 12, 2023.
Machiraju et al. "Identification, synthesis and evaluation of CSF1R inhibitors using fragment based drug design." Computational Biology and Chemistry 80 (2019): 374-383.
Oosterhof et al. "Colony-stimulating factor 1 receptor (CSF1R) regulates microglia density and distribution, but not microglia differentiation in vivo." Cell reports 24.5 (2018): 1203-1217.
Han et al. "Microglial replacement therapy: a potential therapeutic strategy for incurable CSF1R-related leukoencephalopathy." Acta neuropathologica communications 8.1 (2020): 1-12.
Mancuso et al. "CSF1R inhibitor JNJ-40346527 attenuates microglial proliferation and neurodegeneration in P301S mice." Brain 142.10 (2019): 3243-3264.
Rubino et al. "Acute microglia ablation induces neurodegeneration in the somatosensory system." Nature communications 9.1 (2018): 4578.
Chadarevian et al. "Engineering an inhibitor-resistant human CSF1R variant for microglia replacement." Journal of Experimental Medicine 220.3 (2022): e20220857.
Salter, et al.: Microglia emerge as central players in brain disease. Nat. Med. 23, 1018-1027.
Schafer, et al.: Microglia Sculpt Postnatal Neural Circuits in an Activity and Complement-Dependent Manner. Neuron. May 24, 2012; 74(4): 691-705. doi: 10.1016/j.neuron.2012.03.026.
Schindelin, et al. Fiji: an open-source platform for biological-image analysis. Nat Methods. Jun. 28, 2012;9 (7):676-682. doi: 10.1038/nmeth.2019.
Schneider, Caroline, et al.: NIH Image to ImageJ: 25 Years of Image Analysis. Nature Methods. vol. 9, Issue No. 7 (2012): 671-675.
Schubert, C. et al.: Crystal structure of the tyrosine kinase domain of colony-stimulating factor-1 receptor (cFMS) in complex with two inhibitors. The Journal of Biological Chemistry 282(6):4094-4101 (2007).
Schuberth, M et al.: Hereditary diffuse leukencephalopathy with spheroids: a microgliopathy due to CSF1 receptor impairment. Nervenarzt 85(4):465-70 (2014). doi: 10.1007/s00115-014-4052-4 (abstract).
Scott, et al.: Bone marrow-derived monocytes give rise to self-renewing and fully differentiated Kupffer cells. Nat. Commun. 7:10321 (2016).
Sekar, et al.: Schizophrenia risk from complex variation of complement component 4. Nature. Feb. 11, 2016; 530 (7589): 177-183. Published online Jan. 27, 2016. doi: 10.1038/nature 16549.
Sellgren, et al.: Patient-specific models of microglia-mediated engulfment of synapses and neural progenitors. Mol. Psychiatry 22:170-177 (2017).
Shi, et al.: Alzheimer's Disease Neuroimaging Initiative (2017). ApoE4 markedly exacerbates tau-mediated neurodegenera-tion in a mouse model of tauopathy. Nature 549, 523-527.
Spangenberg, Elizabeth et al.: Sustained microglial depletion with CSF1R inhibitor impairs parenchymal plaque development in an Alzheimer's disease model. Nature Communications 10: 3758 (2019).
Subramanian, et al.: Gene set enrichment analysis: a knowledge-based approach for interpreting genome-wide expression profiles. Proc. Natl. Acad. Sci. USA 102:15545-15550 (2005).
Suzuki, et al.: pvclust: hierarchical clustering with p-values via multiscale Bootstrap resampling. R package version 1.2-2 (2014). https://cran.r-project.org/web/packages/pvclust/index.html.
The gene summary of CSF1R from the website: bioinfo.uth.edu/mutLBSgene_search_result.cgi?page=page&type=quick_search&quick_search=1436 retrieved on Jul. 18, 2023.
Thion, et al.: Microbiome Influences Prenatal and Adult Microglia in a Sex-Specific Manner. Cell. Jan. 25, 2018; 172(3): 500-516.e16. doi: 10.1016/j.cell.2017.11.042.
Trapnell, et al. (2012). Differential gene and tra••script expression analysis of RNA-seq experiments with TopHat and Cufflinks. Nat. Protoc. 7, 562-578.
Trapnell, et al.: Pseudo-temporal ordering of individual cells reveals dynamics and regulators of cell fate decisions. Nat Biotechnol. Apr. 2014; 32(4): 381-386. Published online Mar. 23, 2014. doi: 10.1038/nbt.2859.
Van De Laar, et al.: Yolk sac macrophages, fetal liver, and adult monocytes can colonize an empty niche and develop into functional tissue-resident macrophages. Immunity 44:755-768 (2016).
Varvel, et al.: (2012). Microglial repopulation model reveals a robust homeostatic process for replacing CNS myeloid cells. Proc. Natl. Acad. Sci. USA 109, 18150-18155.
Villa, et al.: Sex-specific features of microglia from adult mice. Cell reports 23.12 (2018): 3501-3511.
Waisman, et al.: Homeostasis of Microglia in the Adult Brain: Review of Novel Microglia Depletion Systems. Trends Immunol. Oct. 2015;36(10):625-636. doi: 10.1016/j.it.2015.08.005.

(56) References Cited

OTHER PUBLICATIONS

Wang, et al.: TREM2 lipid sensing sustains the microglial response in an Alzheimer's disease model. Cell 160, 1061-1071 (2015).

Wenger, et al.: Krabbe disease: One Hundred years from the bedside to the bench to the bedside. J Neurosci Res. Nov. 2016;94(11):982-9. doi: 10.1002/jnr.23743.

Wong, et al. (2017). Mice deficient in NRROS show abnormal microglial development and neurological disorders. Nat. Immunol. 18, 633-641.

Yang, et al.: Perivascular, but not Parenchymal, Cerebral Engraftment of Donor Cells after Non-Myeloablative Bone Marrow Transplantation. Exp Mol Pathol. Aug. 2013; 95(1): 7-17. Published online Apr. 6, 2013. doi: 10.1016/j.yexmp.2013.03.010.

Zhang, C. et al.: Design and pharmacology of a highly specific dual FMS and KIT kinase inhibitor. PNAS 110(14):5689-5694 (2013). https://doi.org/10.1073/pnas. 1219457110.

Zhou, et al.: In vivo simultaneous transcriptional activation of multiple genes in the brain using CRISPR-dCas9-activator transgenic mice. Nat Neurosci. Mar. 2018;21(3):440-446. doi: 10.1038/s41593-017-0060-6. Epub Jan. 15, 2018.

Biffi, et al.: Lentiviral hematopoietic stem cell gene therapy benefits metachromatic leukodystrophy. Science. Aug. 23, 2013;341(6148):1233158. doi: 10.1126/science. 1233158. Epub Jul. 11, 2013.

Bohlen, et al.: Diverse requirements for microglial survival, specification, and function revealed by defined-medium cultures. Neuron. May 17, 2017; 94(4): 759-773.e8.

Sagar, et al.: Antibody blockade of CLEC12A delays EAE onset and attenuates disease severity by impairing myeloid cell CNS infiltration and restoring positive immunity. Sci. Rep. 7:2707 (2017).

Da Silva Figueiredo, Priscila et al.: Insight on Mutation-Induced Resistance from Molecular Dynamics Simulations of the Native and Mutated CSF-1R and Kit. PLOS One 11(7):e0160165 (2016). DOI:10.1371/journal.pone.0160165.

Extended European Search Report dated Feb. 7, 2025 issued in EP22782325.9.

Gandin, Valentina et al.: Targeting kinases with anilinopyrimidines: discovery of N-phenyl-N'-[4-(pyrimidin-4-ylamino)phenyl]urea derivatives as selective inhibitors of class III receptor tyrosine kinase subfamily. Scientific Reports 5(1):1-16 (2015). DOI: 10.1038/srep16750.

Morley, GM et al.: Cell specific transformation by c-fms activating loop mutations is attributable to constitutive receptor degradation. Oncogene 18:3076-3084 (1999).

Pridans, Clare et al.: CSF1R mutations in hereditary diffuse leukoencephalopathy with spheroids are loss of function. Scientific Reports 3: 3013 (2013). DOI: 10.1038/srep03013.

Bailey, et al.: The Resistance Tetrad: Amino Acid Hotspots for Kinome-Wide Exploitation of Drug-Resistant Protein Kinase Alleles. Methods in Enzymology 548:117-146 (2014).

U.S. Appl. No. 16/566,675 Office Action dated Jun. 13, 2024.

Cole, et al. Mutation of a highly conserved aspartate residue in subdomain IX abolishes Fer protein-tyrosine kinase activity. Protein Engineering 12(2):155-162 (1999).

Gani, et al.: Evaluating the predictivity of virtual screening for ABL kinase inhibitors to hinder drug resistance. Chemical Biology and Drug Design 82(5):506-519 (2013).

Krishnamurty, et al. Biochemical Mechanisms of Resistance to Small-Molecule Protein Kinase Inhibitors. ACS Chemical Biology 5(1):121-138 (2010).

U.S. Appl. No. 18/069,631 Office Action dated Jan. 25, 2024.

\* cited by examiner

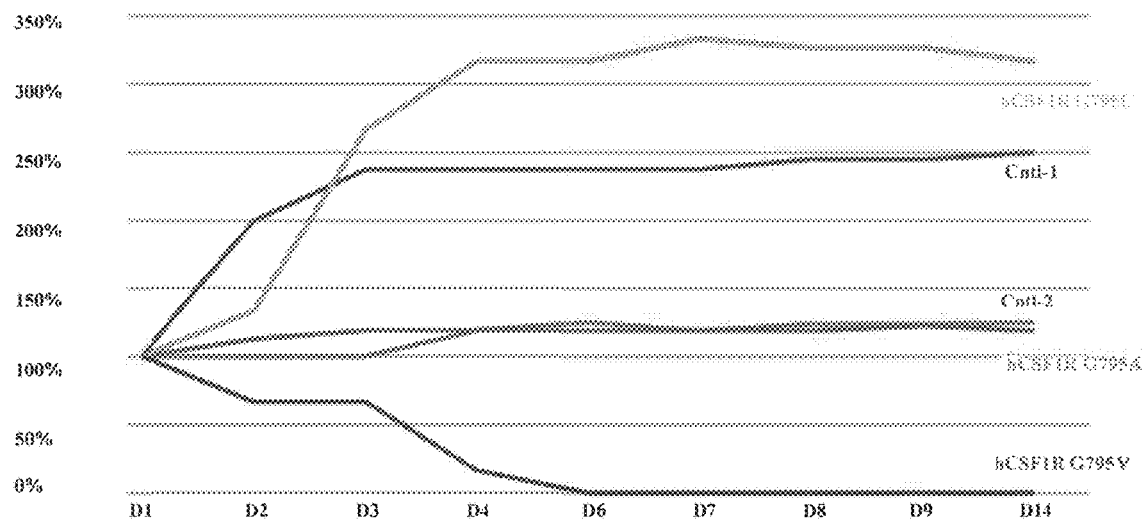
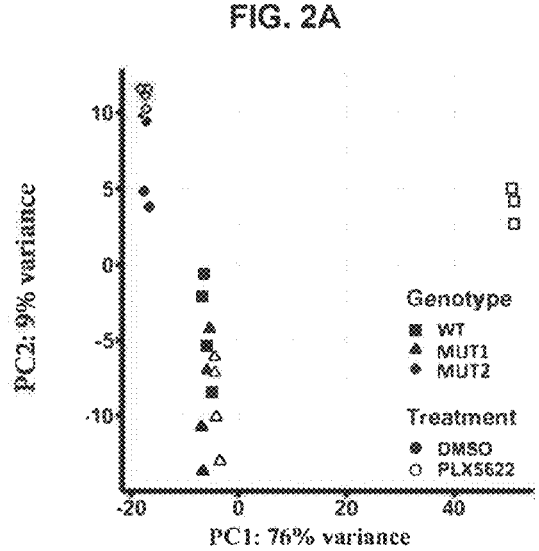
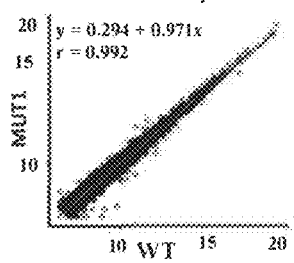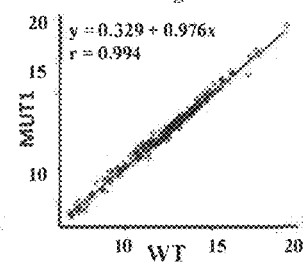
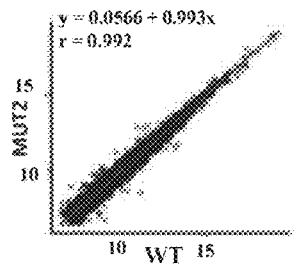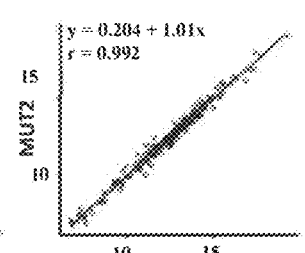

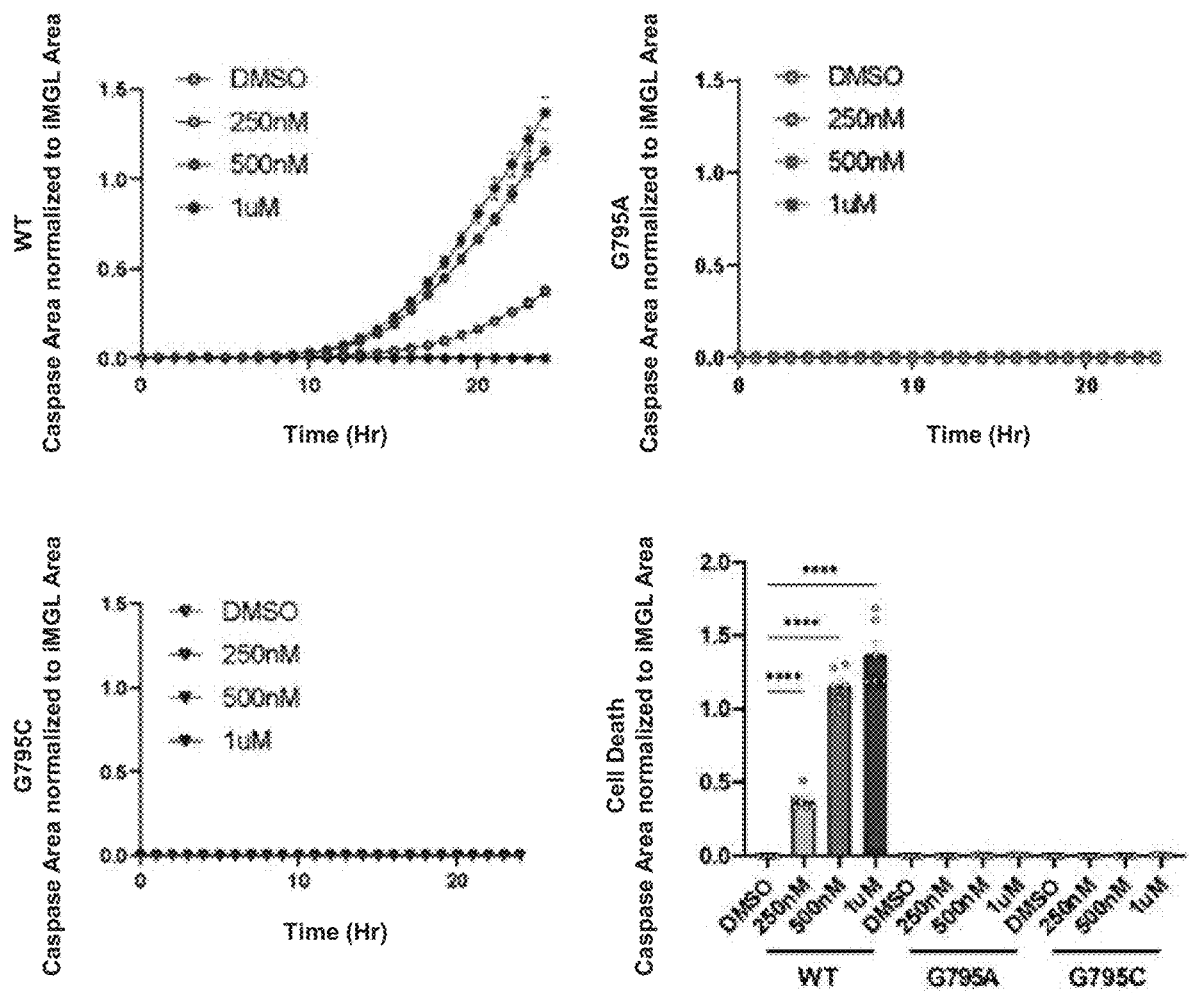

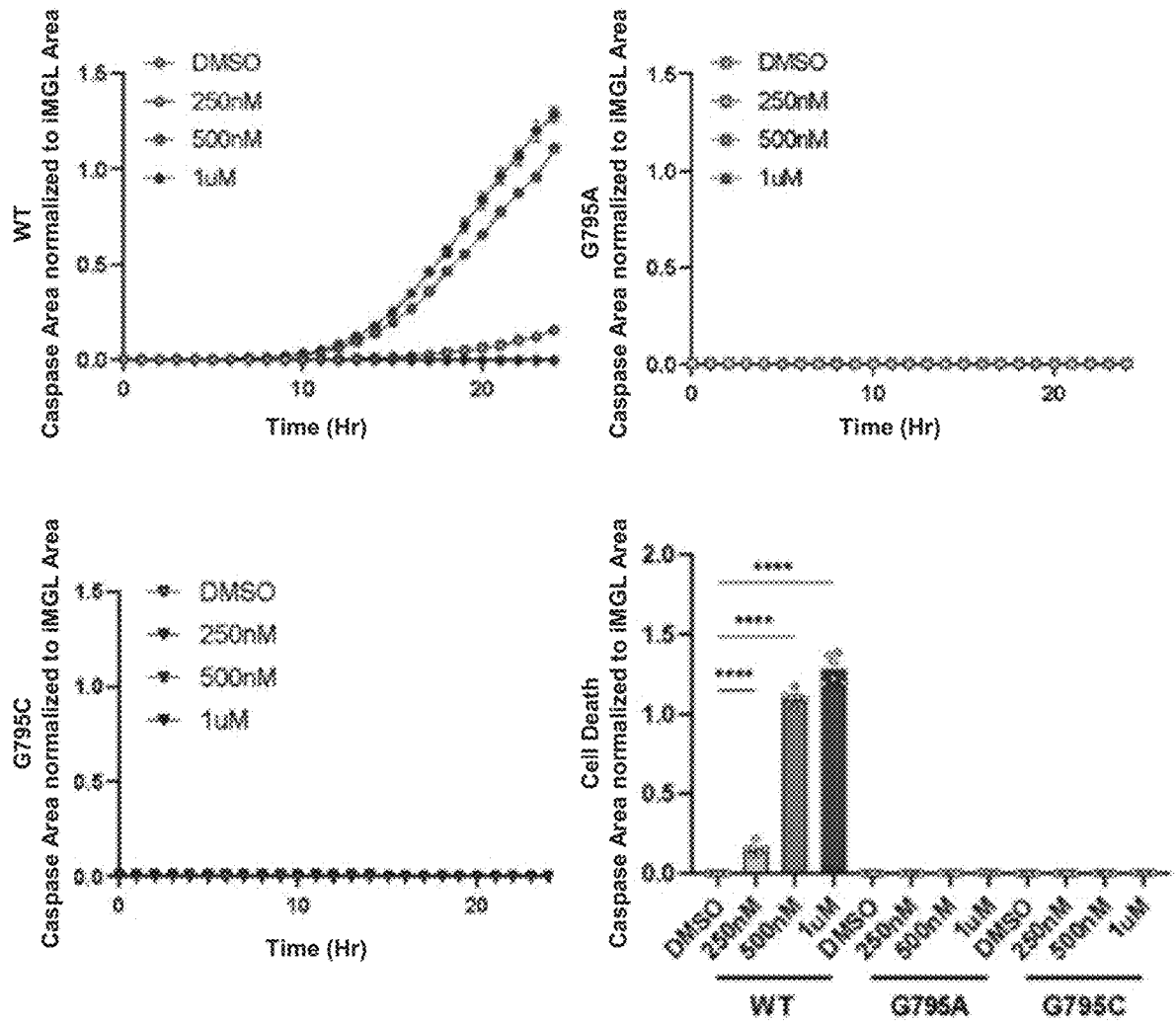

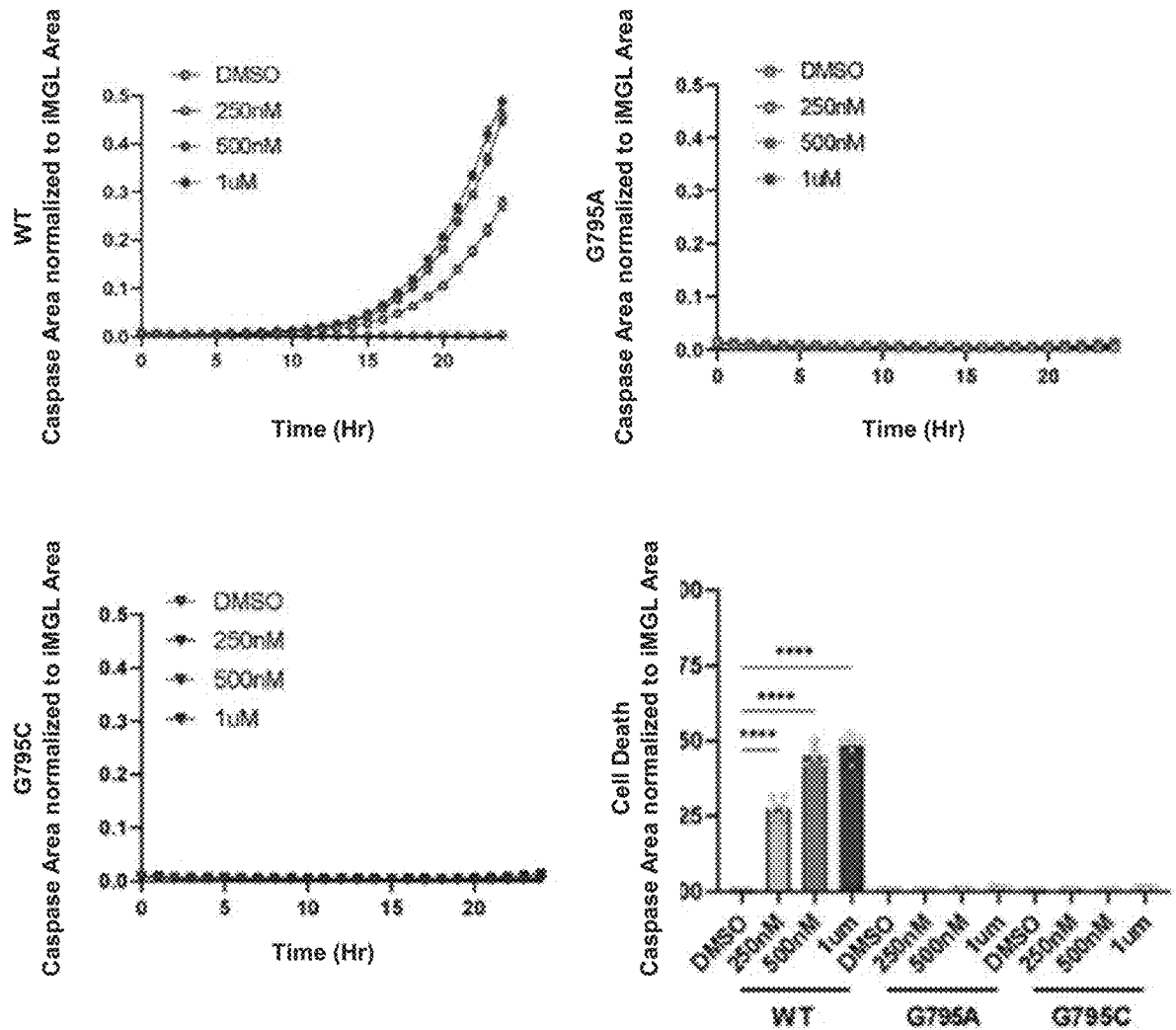

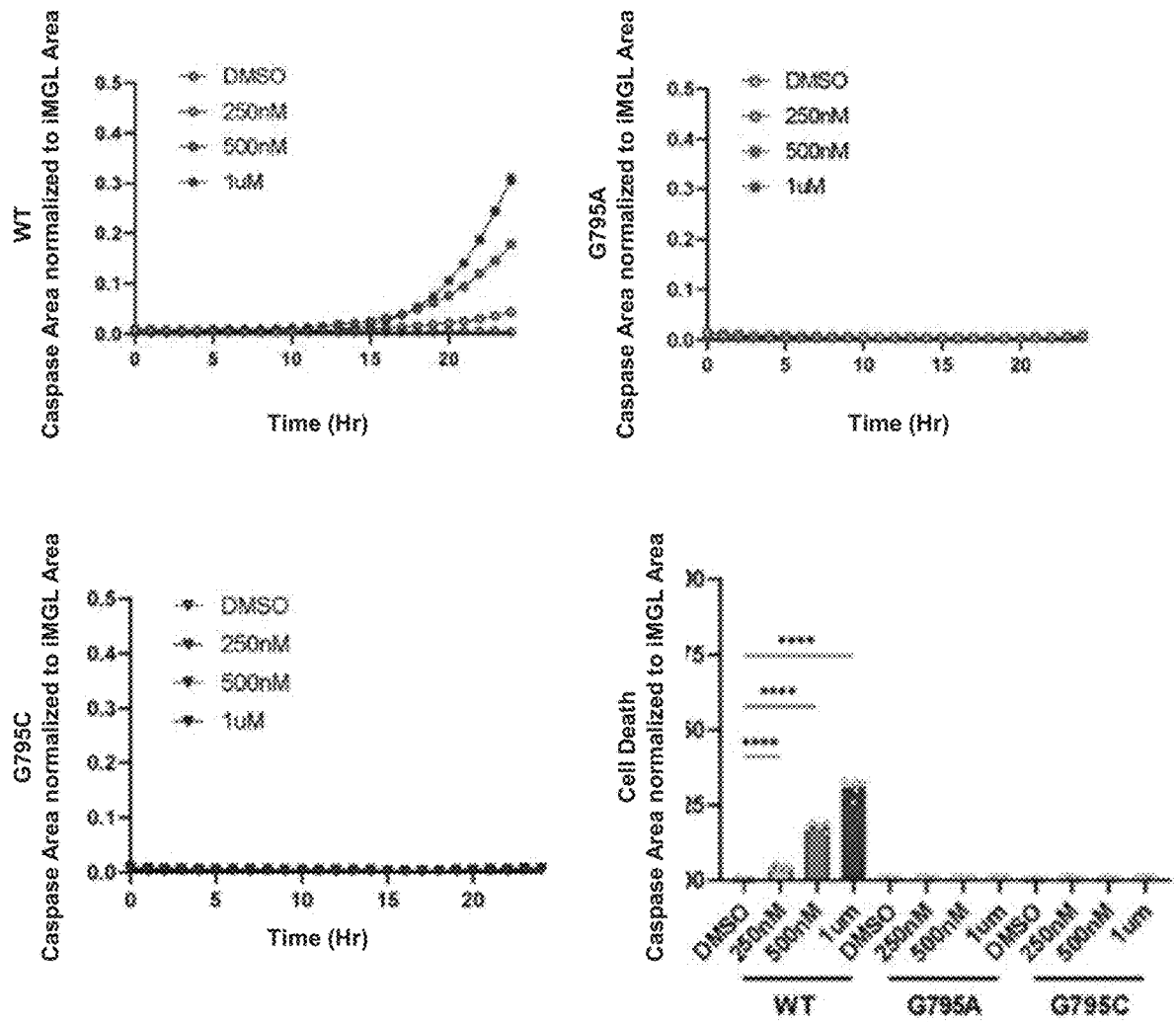

FIG. 4E
Plexxikon 3397
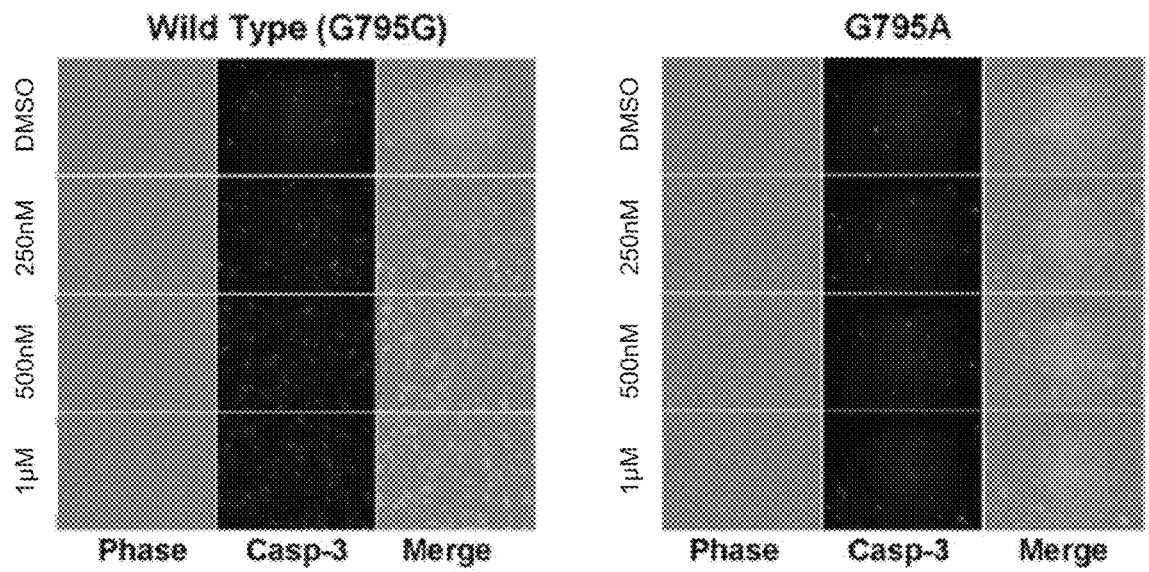
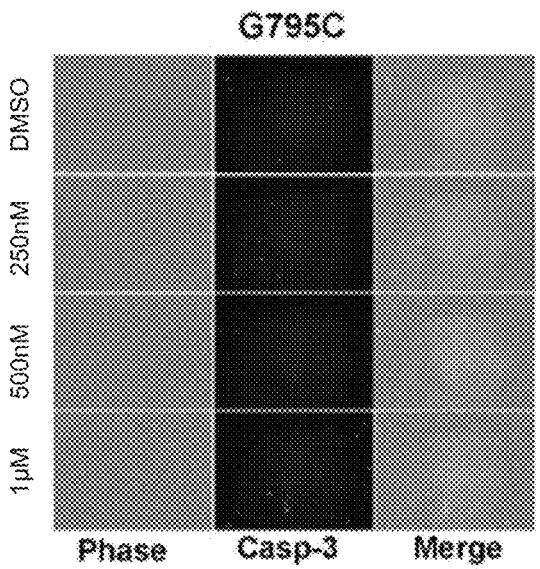
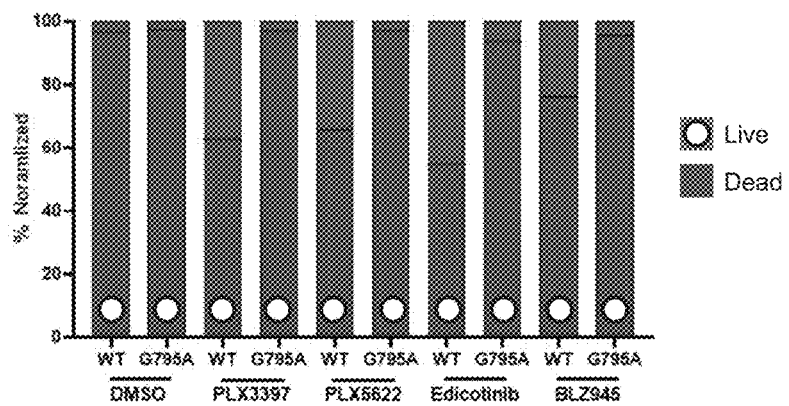
FIG. 5A hCSF1R-PLX5622 complex

PDB 6N33
PLX5622 hCSF1R-PLX3397 complex

PDB 4R7H
PLX3397

IBA-1

Human Nuclei (Ku80)

Ki67 (mitotic nuclei)

IBA-1/Ku80/Ki67

IBA-1/Ku80/Ki67

Figure 11A:
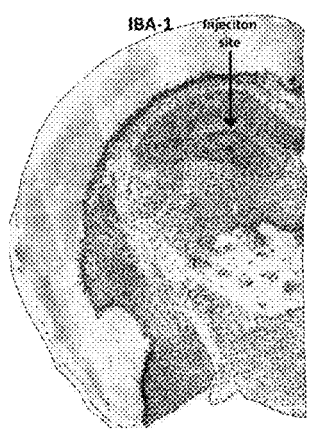
Figure 11B:
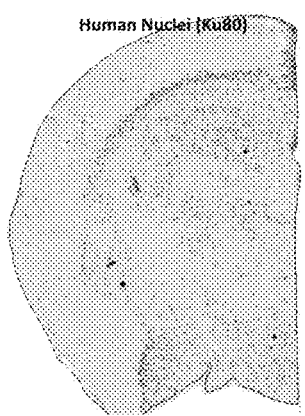
Figure 11C:
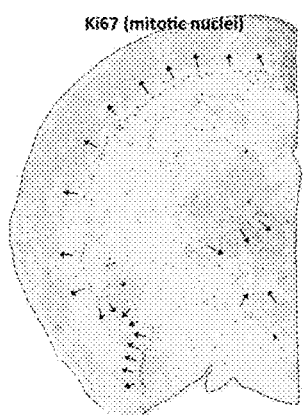
Figure 11D:
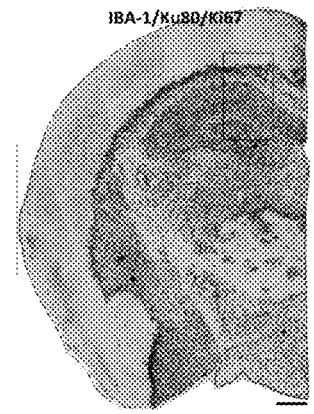

FIG. 11F
IBA-1
FIG. 11G
Human Nuclei (Ku80)
FIG. 11H
Ki67 (mitotic nuclei)
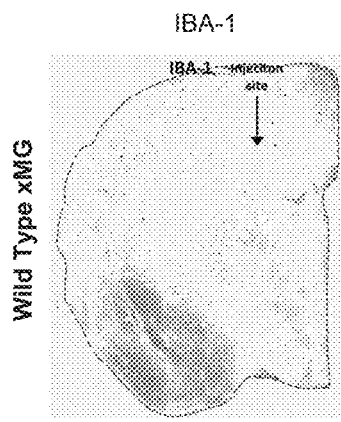
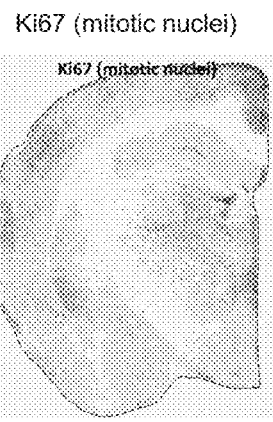
FIG. 11I
IBA-1/Ku80/Ki67
FIG. 11J
IBA-1/Ku80/Ki67
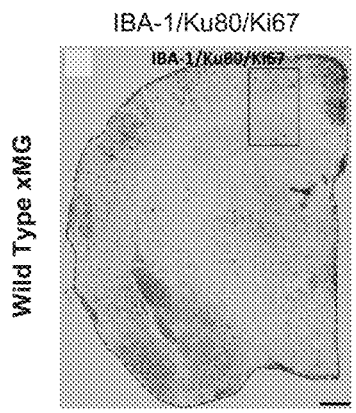
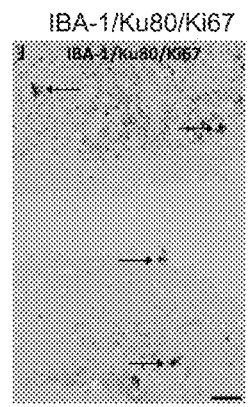
FIG. 12
Engraftment of G795A iMGs
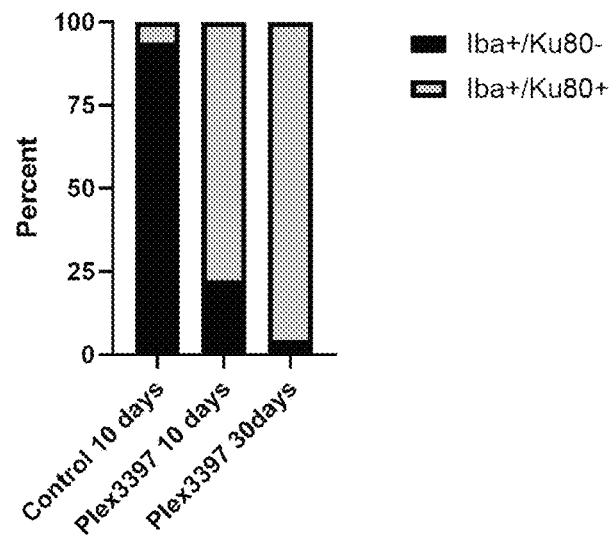

SEQUENCE LISTING

```
Sequence total quantity: 8
SEQ ID NO: 1            moltype = DNA  length = 2919
FEATURE                 Location/Qualifiers
source                  1..2919
                        mol_type = genomic DNA
                        organism = Homo sapiens
SEQUENCE: 1
atgggcccag gagttctgct gctcctgctg gtggccacag cttggcatgg tcagggaatc  60
ccagtgatag agcccagtgt ccctgagctg gtcgtgaagc caggagcaac ggtgaccttg  120
cgatgtgtgg gcaatggcag cgtggaatgg gatggccccc catcacctca ctggaccctg  180
tactctgatg gctccagcag catcctcagc accaacaacg ctaccttcca aaacacgggg  240
acctatcgct gcactgagcc tggagacccc ctgggaggca gcgccgccat ccacctctat  300
gtcaaagacc ctgcccggcc ctggaacgtg ctagcacagg aggtggtcgt gttcgaggac  360
caggacgcac tactgccctg tctgctcaca gacccggtgc tggaagcagg cgtctcgctg  420
gtgcgtgtgc gtggccggcc cctcatgcgc cacaccaact actccttctc gccctggcat  480
ggcttcacca tccacagggc caagttcatt cagagccagg actatcaatg cagtgccctg  540
atgggtggca ggaaggtgat gtccatcagc atccggctga aagtgcagaa agtcatccca  600
gggcccccag ccttgacact ggtgcctgca gagctggtgc ggattcgagg ggaggctgcc  660
cagatcgtgt gctcagccag cagcgttgat gttaactttg atgtcttcct ccaacacaac  720
aacaccaagc tcgcaatccc tcaacaatct gactttcata ataaccgtta ccaaaaagtc  780
ctgaccctca acctcgatca agtagatttc caacatgccg gcaactactc ctgcgtggcc  840
agcaacgtgc agggcaagca ctccacctcc atgttcttcc gggtggtaga gagtgcctac  900
ttgaacttga gctctgagca gaacctcatc caggaggtga ccgtggggga ggggctcaac  960
ctcaaagtca tggtggaggc ctacccaggc ctgcaaggtt ttaactggac ctacctggga  1020
cccttttctg accaccagcc tgagcccaag cttgctaatg ctaccaccaa ggacacatac  1080
aggcacacct tcaccctctc tctgccccgc ctgaagccct ctgaggctgg ccgctactcc  1140
ttcctggcca gaaacccagg aggctggaga gctctgacgt ttgagctcac ccttcgatac  1200
cccccagagg taagcgtcat atggacattc atcaacggct ctggcaccct tttgtgtgct  1260
gcctctgggt acccccagcc caacgtgaca tggctgcagt gcagtggcca cactgatagg  1320
tgtgatgagg cccaagtgct gcaggtctgg gatgacccat accctgaggt cctgagccag  1380
gagcccttcc acaaggtgac ggtgcagagc ctgctgactg ttgagacctt agagcacaac  1440
caaacctacg agtgcagggc ccacaacagc gtggggagtg gctcctgggc cttcataccc  1500
atctctgcag gagcccacac gcatcccccg gatgagttcc tcttcacacc agtggtggtc  1560
gcctgcatgt ccatcatggc cttgctgctg ctgctgctcc tgctgctatt gtacaagtat  1620
```

```
aagcagaagc caagtacca ggtccgctgg aagatcatcg agagctatga gggcaacagt    1680
tatactttca tcgaccccac gcagctgcct tacaacgaga agtgggagtt cccccgaac    1740
aacctgcagt ttggtaagac cctcggagct ggagcctttg gaaggtggt ggaggccacg    1800
gcctttggtc tgggcaagga ggatgctgtc ctgaaggtgg ctgtgaagat gctgaagtcc    1860
acggcccatg ctgatgagaa ggaggccctc atgtccagcc tgaagatcat gagccacctg    1920
ggccagcacg agaacatcgt caaccttctg ggagcctgta cccatggagg ccctgtactg    1980
gtcatcacgg agtactgttg ctatggcgac ctgctcaact ttctgcgaag gaaggctgag    2040
gccatgctgg gacccagcct gagccccggc caggaccccg agggaggcgt cgactataag    2100
aacatccacc tcgagaagaa atatgtccgc agggacagtg gcttctcaca gcagggtgtg    2160
gacacctatg tggagatgag gcctgtctcc acttcttcaa atgactcctt ctctgagcag    2220
gacctggaca aggaggatgg acggcccctg gagctccggg acctgcttca cttctccagc    2280
caagtagccc agggcatggc cttcctgcct tccaagaatt gcatccaccg ggacgtggca    2340
gcgcgtaacg tgctgttgac caatggtcat gtggccaaga ttggggactt cgggctggct    2400
agggacatca tgaatgactc caactacatt gtcaaggcca atgcccgcct gcctgtgaag    2460
tggatggccc cagagagcat ctttgactgt gtctacacgg ttcagagcga cgtctggtcc    2520
tatggcatcc tcctctggga gatcttctca cttgggctga tcctaccc tggcatcctg    2580
gtgaacagca agttctataa actggtgaag gatggatacc aaatggccca gcctgcattt    2640
gccccaaaga atatatacag catcatgcag gcctgcctgg ccttggagcc cacccacaga    2700
cccaccttcc agcagatctg ctccttcctt caggagcagg cccaagagga caggagagag    2760
cgggactata ccaatctgcc gagcagcagc agaagcggtg gcagcggcag cagcagcagt    2820
gagctggagg aggagagctc tagtgagcac ctgacctgct gcgagcaagg ggatatcgcc    2880
cagcccttgc tgcagcccaa caactatcag ttctgctga                           2919

SEQ ID NO: 2           moltype = AA   length = 972
FEATURE                Location/Qualifiers
source                 1..972
                       mol_type = protein
                       organism = Homo sapiens
SEQUENCE: 2
MGPGVLLLLL VATAWHGQGI PVIEPSVPEL VVKPGATVTL RCVGNGSVEW DGPPSPHWTL    60
YSDGSSSILS TNNATFQNTG TYRCTEPGDP LGGSAAIHLY VKDPARPWNV LAQEVVVFED   120
QDALLPCLLT DPVLEAGVSL VRVRGRPLMR HTNYSFSPWH GFTIHRAKFI QSQDYQCSAL   180
MGGRKVMSIS IRLKVQKVIP GPPALTLVPA ELVRIRGEAA QIVCSASSVD VNFDVFLQHN   240
NTKLAIPQQS DFHNNRYQKV LTLNLDQVDF QHAGNYSCVA SNVQGKHSTS MFFRVVESAY   300
LNLSSEQNLI QEVTVGEGLN LKVMVEAYPG LQGFNWTYLG PFSDHQPEPK LANATTKDTY   360
RHTFTLSLPR LKPSEAGRYS FLARNPGGWR ALTFELTLRY PPEVSVIWTF INGSGTLLCA   420
ASGYPQPNVT WLQCSGHTDR CDEAQVLQVW DDPYPEVLSQ EPFHKVTVQS LLTVETLEHN   480
QTYECRAHNS VGSGSWAFIP ISAGAHTHPP DEFLFTPVVV ACMSIMALLL LLLLLLLYKY   540
KQKPKYQVRW KIIESYEGNS YTFIDPTQLP YNEKWEFPRN NLQFGKTLGA GAFGKVVEAT   600
AFGLGKEDAV LKVAVKMLKS TAHADEKEAL MSELKIMSHL GQHENIVNLL GACTHGGPVL   660
VITEYCCYGD LLNFLRRKAE AMLGPSLSPG QDPEGGVDYK NIHLEKKYVR RDSGFSSQGV   720
DTYVEMRPVS TSSNDSFSEQ DLDKEDGRPL ELRDLLHFSS QVAQGMAFLA SKNCIHRDVA   780
ARNVLLTNGH VAKIGDFGLA RDIMNDSNYI VKGNARLPVK WMAPESIFDC VYTVQSDVWS   840
YGILLWEIFS LGLNPYPGIL VNSKFYKLVK DGYQMAQPAF APKNIYSIMQ ACWALEPTHR   900
PTFQQICSFL QEQAQEDRRE RDYTNLPSSS RSGGSGSSSS ELEEESSSEH LTCCEQGDIA   960
QPLLQPNNYQ FC                                                       972

SEQ ID NO: 3           moltype = DNA   length = 2919
FEATURE                Location/Qualifiers
misc_feature           1..2919
                       note = G795A CSF1R
misc_difference        2383..2385
                       note = nnn is gct
misc_difference        2383..2385
                       note = nnn is gcc
misc_difference        2383..2385
                       note = nnn is gca
misc_difference        2383..2385
                       note = nnn is gcg
source                 1..2919
                       mol_type = other DNA
                       organism = synthetic construct
SEQUENCE: 3
atgggcccag gagttctgct gctcctgctg gtgccacag cttggcatgg tcagggaatc     60
ccagtgatag agcccagtgt ccctgagctg gtcgtgaagc aggagcaac ggtgaccttg    120
cgatgtgtgg gcaatggcag cgtggaatgg gatggccccc catcacctca ctggaccctg    180
tactctgatg gctccagcag catcctcagc accaacaacg ctaccttca aaacacgggg    240
acctatcgct gcactgagcc tggagaccc ctgggaggca gcgccgccat ccacctctat    300
gtcaaagacc ctgcccggcc ctggaacgtg ctagcacagg aggtggtcgt gttcgaggac    360
caggacgcac tactgccctg tctgctcaca gacccggtgc tggaagcagg cgtctcgctg    420
gtgcgtgtgc gtggccggcc cctcatgcgc cacaccaact actccttctc gccctggcat    480
ggcttcacca tccacagggc caagttcatt cagagccagg actatcaatg cagtgccctg    540
atgggtggca ggaaggtgat gtccatcagc atccggctga aagtcagaa agtgatccca    600
gggccccaaa ccttgacact ggtgcctgca gagctggtga ggattcgagg gaggcctgcc    660
cagatcgtgt gctcagccag cagcgttgat gttaactttg atgtcttcct ccaacacaac    720
aacaccaagc tcgcaatccc tcaacaatct gactttcata taaccgtta ccaaaaagtc    780
ctgaccctca acctgatca gtagatttc aacatgccg gcaactactc ctgcgtggcc    840
agcaacgtgc agggcaagca ctccacctcc atgttcttcc gggtggtaga gagtgcctac    900
ttgaactga gctctgagca gaacctcatc caggaggtga ccgtggggga ggggctcaac    960
```

```
ctcaaagtca tggtggaggc ctacccaggc ctgcaaggtt ttaactggac ctacctggga   1020
cccttttctg accaccagcc tgagcccaag cttgctaatg ctaccaccaa ggacacatac   1080
aggcacacct tcaccctctc tctgcccccgc ctgaagccct ctgaggctgg ccgctactcc  1140
ttcctggcca gaaacccagg aggctggaga gctctgacgt tgagctcac ccttcgatac    1200
cccccagagg taagcgtcat atggacattc atcaacgct ctggcaccct tttgtgtgct    1260
gcctctgggt acccccagcc caacgtgaca tggctgcagt gcagtggcca cactgatagg   1320
tgtgatgagg cccaagtgct gcaggtctgg gatgacccat accctgaggt cctgagccag   1380
gagcccttcc acaaggtgac ggtgcagagc ctgctgactg ttgagacctt agagcacaac   1440
caaacctacg agtgcaggc ccacaacagc gtggggagtg gctcctgggc cttcataccc    1500
atctctgcag gagcccacac gcatgagttcc tcttcacacc agtggtggtc              1560
gcctgcatgt ccatcatggc cttgctgctg ctgctgctcc tgctgctatt gtacaagtat   1620
aagcagaagc ccaagtacca ggtccgctgg aagatcatcg agagctatga gggcaacagt   1680
tatactttca tcgaccccac gcagctgcct tacaacgaga agtgggagtt cccccggaac   1740
aacctgcagt ttggtaagac cctcggagct ggagccttt ggaaggtggt ggaggccacg    1800
gcctttggtc tgggcaagga ggatgctgtc ctgaaggtgg ctgtgaagat gctgaagtcc   1860
acggcccatg ctgatgagaa ggaggccctc atgtccgagc tgaagatcat gagccacctg   1920
ggccagcacg agaacatcgt caaccttctg ggagcctgta cccatggagg ccctgtactg   1980
gtcatcacgg agtactgttg ctatgcgac ctgctcaact ttctgcgaag gaaggctgag    2040
gccatgctgg gacccagcct gagccccggc caggacccccg agggaggcgt cgactataag   2100
aacatccacc tcgagaagaa atatgtccgc agggacagtg gcttctccag ccagggtgtg   2160
gacacctatg tggagatgag gcctgtctcc acttcttcaa atgactcctt ctctgagcaa   2220
gacctggaca aggagatgg acggcccctg gagctccggg acctgcttca cttctccagg    2280
caagtagccc agggcatggc cttcctgcgct ccaagaatt gcatccaccg ggacgtggca   2340
gcgcgtaacg tgctgttgac caatggtcat gtgccaaga ttnnngactt cgggctggct    2400
agggacatca tgaatgactc caactacatt gtcaagggca tgcccgcct gcctgtgaag   2460
tggatgccc cagagagcat cttttgactgt gtctcacagg ttcagagcga cgtctggtcc   2520
tatggcatcc tcctctggga gatcttctca cttgggctga atcctacc tggcatcctg     2580
gtgaacagca agttctataa actggtgaag gatggatacc aaatggccca gcctgcattt   2640
gccccaaaga atatatacag catcatgcag gcctgctggg ccttggagcc cacccacaga   2700
cccaccttcc agcagatctg ctccttcctt caggagcagg cccaagagga caggagagag   2760
cgggactata ccaatctgcc gagcagcagc agaagcggtg gcagcggcag cagcagcagt   2820
gagctggagg aggagagctc tagtgagcac ctgacctgct gcgagcaagg ggatatcgcc   2880
cagcccttgc tgcagcccaa caactatcag ttctgctga                          2919

SEQ ID NO: 4           moltype = AA   length = 972
FEATURE                Location/Qualifiers
REGION                 1..972
                       note = G795A CSF1R
source                 1..972
                       mol_type = protein
                       organism = synthetic construct
SEQUENCE: 4
MGPGVLLLLL VATAWHGQGI PVIEPSVPEL VVKPGATVTL RCVGNGSVEW DGPPSPHWTL    60
YSDGSSSILS TNNATFQNTG TYRCTEPGDP LGGSAAIHLY VKDPARPWNV LAQEVVFED    120
QDALLPCLLT DPVLEAGVSL VRVRGRPLMR HTNYSFSPWH GFTIHRAKFI QSDDYQCSAL   180
MGGRKVMSIS IRLKVQKVIP GPPALTLVPA ELVRIRGEAA QIVCSASSVD VNFDVFLQHN   240
NTKLAIPQQS DFHNNRYQKV LTLNLDQVDF QHAGNYSCVA KGHKHSTS MFFRVVESAY     300
LNLSSEQNLI QEVTVGEGLN LKVMVEAYPG LQGFNWTYLG PFSDHQPEPK LANATTKDTY   360
RHTFTLSLPR LKPSEAGRYS FLARNPGGWR ALTFELTLRY PPEVSVIWTF INGSGTLLCA   420
ASGYPQPNVT WLQCSGHTDR CDEAQVLQVW DDPYPEVLSQ EPFHKVTVQS LLTVETLEHN   480
QTYECRAHNS VGSGSWAFIP ISAGAHTHPP DEFLFTPVMN ACMSIMALLL LLLLLLYKY    540
KQKPKYQVRW KIIESYEGNS YTFIDPTQLP YNEKWEFPRN NLQFGKTLGA GAFGKVVEAT   600
AFGLGKEDAV LKVAVKMLKS TAHADEKEAL MSELKIMSHL GQHENIVNLL GACTHGGPVL   660
VITEYCCYGD LLNFLRRKAE AMLGPSLSPG QDPEGGVDYK NIHLEKKYVR RDSGFSSQGV   720
DTYVEMRPVS TSSNDSFSEQ DLDKEDGRPL ELRDLLHFSS QVAQGMAFLA SKNCIHRDVA   780
ARNVLLTNGH VAKIADFGLA RDIMNDSNYI VKGNARLPVK WMAPESIFDC VYTVQSDVWS   840
YGILLWEIFS LGLNPYPGIL VNSKFYKLVK DGYQMAQPAF APKNIYSIMQ ACWALEPTHR   900
PTFQQICSFL QEQAQEDRRE RDYTNLPSSS RSGGSGSSSS ELEEESSSEH LTCCEQGDIA   960
QPLLQPNNYQ FC                                                      972

SEQ ID NO: 5           moltype = DNA   length = 2919
FEATURE                Location/Qualifiers
misc_feature           1..2919
                       note = G795C CSF1R
misc_difference        2328..2385
                       note = nnn is tgt
misc_difference        2328..2385
                       note = nnn is tgc
source                 1..2919
                       mol_type = other DNA
                       organism = synthetic construct
SEQUENCE: 5
atgggcccag gagttctgct gctcctgctg gtggccacag cttggcatgg tcagggaatc    60
ccagtgatag agcccagtgt ccctgagctg gtcgtgaagc caggagcaac ggtgaccttg   120
cgatgtgtgg gcaatggcag cgtggaatgg gatggccccc catcacctca ctggaccctg   180
tactctgatg gctccagcag catccctcagc accaacaacg ctaccttcca aaacacgggg   240
acctatcgct gcactgagcc tggagacccc ctggggaggca cgccgccat ccacctctat    300
gtcaaagacc ctgcccggcc ctggaacgtg ctagcacagg aggtggtcgt gttcgaggac   360
caggacgcac tactgccctg tctgctcaca gacccggtgc tggaagcagg cgtctcgctg   420
```

```
gtgcgtgtgc gtggccggcc cctcatgcgc cacaccaact actccttctc gccctggcat    480
ggcttcacca tccacagggc caagttcatt cagagccagg actatcaatg cagtgccctg    540
atgggtggca ggaaggtgat gtccatcagc atccggctga aagtgcagaa agtcatccca    600
gggcccccag ccttgacact ggtgcctgca gagctggtgc ggattcgagg ggaggctgcc    660
cagatcgtgt gctcagccag cagcgttgat gttaactttg atgtcttcct ccaacacaac    720
aacaccaagc tcgcaatccc tcaacaatct gactttcata taaccgttac ccaaaaagtc    780
ctgaccctca acctcgatca agtagatttc aacatgccgg caactactcc tgcgtggcc     840
agcaacgtgc agggcaagca ctccacctcc atgttcttcc gggtggtaga gagtgcctac    900
ttgaacttga gctctgagca gaacctcatc caggaggtga ccgtgggga ggggctcaac      960
ctcaaagtca tggtgaggc ctacccaggc ctgcaaggtt ttaactggac ctacctggga    1020
cccttttctg accaccagcc tgagcccaag cttgctaatg ctaccaccaa ggacacatac    1080
aggcacacct tcaccctctc tctgccccgc ctgaagccct tgaggctgg ccgctactcc     1140
ttcctggcca gaaacccagg aggctggaga gctctgacgt tgagctcac ccttcgatac     1200
ccccagagg taagcgtcat atggacattc atcaacgct ctggcaccct tttgtgtgct      1260
gcctctgggt accccagcc aacgtgaca tggcgcagt gcagtggcca cactgatagg       1320
tgtgatgagc cccaagtgct gcaggtctgg atgacccat accctgaggt cctgagccag     1380
gagcccttcc acaaggtgac ggtgcagagc tgctgactg ttgagacctt agagcacaac      1440
caaacctacg agtgcaggc ccaaacagc gtggggagtg gctcctgggc cttcatcccc      1500
atctctgcag gagcccacac gcatcccccg gatgagtcc tcttcacacc agtggtggtc     1560
gcctgcatgt ccatcatggc cttgctgctg ctgctgctcc tgctgctatt gtacaagtat    1620
aagcagaagc ccaagtacca ggtccgctgg aagatcatcg agagctatga gggcaacagt    1680
tatacttca tcgaccccac gcagtgcct tacaacagaa agttggagtt ccccgaac         1740
aacctgcagt ttggtaagac cctcggagct ggagcctttg gaaggtggt ggaggccacg     1800
gcctttggtc tgggcaagga ggatgctgtc ctgaaggtgg ctgtgaagat gctgaagtcc    1860
acggcccatg ctgatgagaa ggaggccctc atgtccgagc tgaagatcat gagccacctg    1920
ggcagccac agaacatcgt caaccttctg ggagcctgta cccatggggg cctgtactg     1980
gtcatcacgg agtactgttg ctatggcgac ctgctcaact ttctgcgaag gaaggctgag   2040
gccatgctgg gacccagcct gagccccggc caggaccccg agggaggcgt cgactataag   2100
aacatccacc tcgagaagaa atatgtccgc agggacagtg gcttctccag ccagggtgtg    2160
gacacctatg tggagatgag gccctgtctc cacttcttcaa atgactcctt ctctgagcaa   2220
gacctggaca ggaggatgg acggcccctg gagctccggg acctgcttca cttctccagc     2280
caagtagccc agggcatggc cttcctgcgc tccaagaatt gcatccaccg ggacgtggca    2340
gcgcgtaacg tgctgttgac caatggtcat gtggccaaga ttnnngactt cgggctggct   2400
agggacatca tgaatgactc caactacatt gtcaagggca atgcccgcct gcctgtgaag   2460
tggatggccc cagagagcat ctttgactgt gtctacacgg ttcagagcga cgtctggtcc    2520
tatggcatcc tcctctggga gatcttctca cttgggctga atccctaccc tggcatcctg   2580
gtgaacagca agttctataa actggtgaag gatggatacc aaatgccca gcctgcattt    2640
gccccaaaga atatatacag catcatgcag gcctgctggg ccttggagcc cacccacaga   2700
cccaccttcc agcagatctg ctccttcctt caggagcaga cccaagagga caggagagag    2760
cgggactata ccaatctgcc gagcagcagc agaagcggtg gcagcggcag cagcagcagt    2820
gagctggagg aggagagctc tagtgagcac ctgacctgct gcgagcaagg ggatatcgcc    2880
cagcccttgc tgcagcccaa caactatcag ttctgctga                            2919

SEQ ID NO: 6              moltype = AA   length = 972
FEATURE                   Location/Qualifiers
REGION                    1..972
                          note = G795C CSF1R
source                    1..972
                          mol_type = protein
                          organism = synthetic construct
SEQUENCE: 6
MGPGVLLLLL VATAWHGQGI PVIEPSVPEL VVKPGATVTL RCVGNGSVEW DGPPSPHWTL     60
YSDGSSSILS TNNATFQNTG TYRCTEPGDP LGGSAAIHLY VKDPARPWNV LAQEVVVFED   120
QDALLPCLLT DPVLEAGVSL VRVRGRPLMR HTNYSFSPWH GFTIHRAKFI QSQDYQCSAL   180
MGGRKVMSIS IRLKVQKVIP GPPALTLVPA ELVRIRGEAA QIVCSASSVD VNFDVFLQHN   240
NTKLAIPQQS DFHNNRYQKV LTLNLDQVDF QHAGNYSCVA SNVQGKHSTS MFFRVVESAY   300
LNLSSEQNLI QEVTVGEGLN LKVMVEAYPG LQGFNWTYLG PFSDHQPEPK LANATTKDTY   360
RHTFTLSLPR LKPSEAGRYS FLARNPGGWR ALTFELTLRY PPEVSVIWTF INGSGTLLCA   420
ASGYPQPNVT WLQCSGHTDR CDEAQVLQVW DDPYPEVLSQ EPFHKVTVQS LLTVETLEHN   480
QTYECRAHNS VGSGSWAFIP ISAGAHTHPP DEFLFTPVVV ACMSIMALLL LLLLLLLYKY   540
KQKPKYQVRW KIIESYEGNS YTFIDPTQLP YNEKWEFPRN NLQFGKTLGA GAFGKVVEAT   600
AFGLGKEDAV LKVAVKMLKS TAHADEKEAL MSELKIMSHL GQHENIVNLL GACTHGGPVL   660
VITEYCCYGD LLNFLRRKAE AMLGPSLSPG QDPEGGVDYK NIHLEKKYVR RDSGFSSQGV   720
DTYVEMRPVS TSSNDSFSEQ DLDKEDGRPL ELRDLLHFSS QVAQGMAFLA SKNCIHRDVA   780
ARNVLLTNGH VAKICDFGLA RDIMNDSNYI VKGNARLPVK WMAPESIFDC VYTVQSDVWS   840
YGILLWEIFS LGLNPYPGIL VNSKFYKLVK DGYQMAQPAF APKNIYSIMQ ACWALEPTHR   900
PTFQQICSFL QEQAQEDRRE RDYTNLPSSS RSGGSGSSSS ELEEESSSEH LTCCEQGDIA   960
QPLLQPNNYQ FC                                                          972

SEQ ID NO: 7              moltype = DNA   length = 2919
FEATURE                   Location/Qualifiers
misc_feature              1..2919
                          note = CSF1R G795V
misc_difference           2383..2385
                          note = nnn is gtt
misc_difference           2383..2385
                          note = nnn is gtc
misc_difference           2383..2385
                          note = nnn is gta
```

| misc_difference | 2383..2385 |
| --- | --- |
| | note = nnn is gtg |
| source | 1..2919 |
| | mol_type = other DNA |
| | organism = synthetic construct |

SEQUENCE: 7

```
atgggcccag gagttctgct gctcctgctg gtggccacag cttggcatgg tcagggaatc    60
ccagtgata  gagcccagtgt ccctgagctg tcgtgaagc caggagcaac ggtgaccttg   120
cgatgtgtgt gcaatggcag cgtggaatgg gatggccccc catcacctca ctggacctg    180
tactctgatg gctccagcag catcctcagc accaacaacg ctaccttcca aaacacgggg   240
acctatcgct gcactgagcc tggagacccc ctgggaggca gcgccgccat ccacctctat   300
gtcaaagacc ctgccggcc  ctggaacgtg ctagcacagg aggtggtcgt gttcgaggac   360
caggacgcac tactgcctg  tctgctcaca gacccggtgc tggaagcagg cgtctcgctg   420
gtgcgtgtgc gtggccggcc cctcatgcgc cacaccaact actccttctc gccctcgcat   480
ggcttcacca tccacagggc caagttcatt cagagccagg actatcaatg cagtgccctg   540
atgggtggca ggaaggtgat gtccatcagc atccggctga agtgcagaa  agtcatccca   600
gggcccccag ccttgacact ggtgcctgca gagctggtgc ggattcgagg ggaggctgcc   660
cagatcgtgt gctcagccag cagcgttgat gttaactttg atgtcttcct ccaacacaac   720
aacaccaagc tcgcaatccc tcaacaatct gactttcata taaccgtta  ccaaaaagtc   780
ctgacccctca acctcgatca agtagatttc aacatgccg  gcaactactc ctgcgtggcc   840
agcaacgtgc agggcaagca ctccacctcc atgttcttcc gggtggtaga gagtgcctac   900
ttgaacttga gctctgagca gaacctcatc caggaggtga ctgtgggagga ggggctcaac   960
ctcaaagtca tggtggaggc ctacccaggc ctgcaaggtt ttaactggac ctacctggga  1020
ccctttctg  accaccagcc tgagcccaag cttgctaatg ctaccaccaa ggacacatac  1080
aggcacacct tcaccctctc tctgcccgc  ctgaagccct tgaggctgg  ccgctactcc  1140
ttcctggcca gaaacccagg aggctggaga ctctgacgt  ttgagctcac ccttcgatac  1200
ccccagagg  taagcgtcat atggacattc atcaacggct ctggcaccct tttgtgtgct  1260
gcctctgggt accccagcc  caacgtgaca tggctgcagt gcagtggcca cactgatagg  1320
tgtgatgagg cccaagtgct gcaggtctgg gatgacccat accctgaggt cctgagccag  1380
gagcccttcc acaaggtgac ggtgcagagc ctgctgaccg ttgagacctt agagcacaac  1440
caaacctacg agtgcagggc ccacaacagc gtggggagtg gctcctgggc cttcataccc  1500
atctctgcag gagcccacac gcatccccg  gatgagttcc tcttcacacc agtggtggtc  1560
gcctgcatgt ccatcatggc cttgctgctg ctgctgctcc tgctgctatt gtacaagtat  1620
aagcagaagc ccaagtacca ggtccgctgg aagatcatcg agagctatga gggcaacagt  1680
tatactttca tcgaccccac gcagctgcct tacaacgaga agtgggagtt ccccggaac  1740
aacctgcagt ttggtaagac cctcggagct ggaggcttg  ggaaggtggt ggaggccacg  1800
gccttggtc  tgggcaagga ggatgctgtc ctgaaggtgg ctgtgaagat gctgaagtcc  1860
acggccatg  ctgatgagaa ggaggccctc atgtccgagc tgaagatcat gagccacctg  1920
ggccagcacg agaacatcgt caaccttctg ggagcctgta cccatggagg ccctgtactg  1980
gtcatcacgg agtactgttg ctatggcgac ctgctcaact ttctgcgaag gaaggctgag  2040
gccatgctgg gacccagcct gagccccggc caggaccccg agggaggcgt cgactataag  2100
aacatccacc tcgagaagaa atatgtccgc agggacagtg gcttctccag ccagggtgtg  2160
gacacctatg tggagatgag gcctgtctcc acttcttcaa atgactcctt ctctgagcaa  2220
gacctggaca aggaggatgg acggcccctg gagctccggg acctgcttca cttctccagc  2280
caagtagccc agggcatggc cttcctgcct tccaagaatt gcatccaccg ggacgtggca  2340
gcgcgtaacg tgctgttgac caatggtcat gtggccaaga ttnnngactt cgggctggct  2400
agggacatca tgaatgactc caactacatt gtcaagggca atgcccgcct gcctgtgaag  2460
tggatggccc cagagagcat cttttgactgt gtctacacgg ttcagagcga cgtctggtcc  2520
tatggcatcc tcctctggga gatcttctca cttgggctga atccctaccc tggcatcctg  2580
gtgaacagca agttctataa actggtgaag gatggatacc aaatggccca gcctgcattt  2640
gccccaaaga atatatacag catcatgcag cctgctggg  ccttggagcc cacccacaga  2700
cccaccttcc agcagatctg ctccttcctt caggagcagg cccaagagga caggagagag  2760
cgggactata ccaatctgcc gagcagcagc agaagcggtg gcagcggcag cagcagcagt  2820
gagctggagg aggagagctc tagtgagcac ctgacctgct gcgagcaagg ggatatcgcc  2880
cagccccttgc tgcagcccaa caactatcag ttctgctga                         2919
```

| SEQ ID NO: 8 | moltype = AA length = 972 |
| --- | --- |
| FEATURE | Location/Qualifiers |
| REGION | 1..972 |
| | note = CSF1R G795V |
| source | 1..972 |
| | mol_type = protein |
| | organism = synthetic construct |

SEQUENCE: 8

```
MGPGVLLLLL VATAWHGQGI PVIEPSVPEL VVKPGATVTL RCVGNGSVEW DGPPSPHWTL    60
YSDGSSSILS TNNATFQNTG TYRCTEPGDP LGGSAAIHLY VKDPARPWNV LAQEVVVFED   120
QDALLPCLLT DPVLEAGVSL VRVRGRPLMR HTNYSFSPWH GFTIHRAKFI QSQDYQCSAL   180
MGGRKVMSIS IRLKVQKVIP GPPALTLVPA ELVRIRGEAA QIVCSASSVD VNFDVFLQHN   240
NTKLAIPQQS DFHNNRYQKV LTLNLDQVDF QHAGNYSCVA SNVQGKHSTS MFFRVVESAY   300
LNLSSEQNLI QEVTVGEGLN LKVMVEAYPG LQGFNWTYLG PFSDHQPEPK LANATTKDTY   360
RHTFTLSLPR LKPSEAGRYS FLARNPGGWR ALTFELTLRY PPEVSVIWTF INGSGTLLCA   420
ASGYPQPNVT WLQCSGHTDR CDEAQVLQVW DDPYPEVLSQ EPFHKVTVQS LLTVETELEHN   480
QTYECRAHNS VGSGSWAFIP ISAGAHTHPP DEFLFTPVVV ACMSIMALLL LLLLLLYKY   540
KQKPKYQVRW KIIESYEGNS YTFIDPTQLP YNEKWEFPRN NLQFGKTLGA GAFGKVVEAT   600
AFGLGKEDAV LKVAVKMLKS TAHADEKEAL MSELKIMSHL GQHENIVNLL GACTHGGPVL   660
VITEYCCYGD LLNFLRRKAE AMLGPSLSPG QDPEGGVDYK NIHLEKKYVR RDSGFSSQGV   720
DTYVEMRPVS TSSNDSFSEQ DLDKEDGRPL ELRDLLHFSS QVAQGMAFLA SKNCIHRDVA   780
```

```
ARNVLLTNGH VAKIVDFGLA RDIMNDSNYI VKGNARLPVK WMAPESIFDC VYTVQSDVWS  840
YGILLWEIFS LGLNPYPGIL VNSKFYKLVK DGYQMAQPAF APKNIYSIMQ ACWALEPTHR  900
PTFQQICSFL QEQAQEDRRE RDYTNLPSSS RSGGSGSSSS ELEEESSSEH LTCCEQGDIA  960
QPLLQPNNYQ FC                                                     972
```

GENETIC MODIFICATION OF MAMMALIAN CELLS TO CONFER RESISTANCE TO CSF1R ANTAGONISTS

CROSS-REFERENCES TO RELATED APPLICATIONS

This application is a continuation and claims benefit of PCT Application No. PCT/US22/23139 filed Apr. 1, 2022, which claims benefit of U.S. Provisional Application No. 63/236,951 filed Aug. 25, 2021, and U.S. Provisional Application No. 63/169,578 filed Apr. 1, 2021, the contents of which is/are incorporated herein in their entirety by reference.

STATEMENT REGARDING FEDERALLY SPONSORED RESEARCH OR DEVELOPMENT

This invention was made with government support under Grant No. RF1DA048813 awarded by the National Institutes of Health. The government has certain rights in the invention.

REFERENCE TO AN ELECTRONIC SEQUENCE LISTING

The contents of the electronic sequence listing (UCI_21_03_PCT_CON1.xml; Size: 29,716 bytes; and Date of Creation: Dec. 21, 2022) is herein incorporated by reference in its entirety.

FIELD OF THE DISCLOSURE

The present disclosure features methods and compositions for the treatment of neurological diseases; in particular, the methods and compositions feature cells with partial or complete resistance to CSF1R antagonists.

BACKGROUND OF THE DISCLOSURE

Almost every human neurological disease and injury involves impairments or alterations in the function, gene expression, and activation state of microglia, the resident immune cell of the brain. In some cases, genetic mutations in microglia are the primary cause of neurological disease, whereas, in other diseases, polymorphisms in microglial genes increase the risk of developing the disease. Unfortunately, there are few, if any, effective therapies for many of these diseases and injuries.

Microglia, monocytes, and macrophages exist within a 'niche' that can limit the total number of microglia, monocytes, and macrophages that reside within the mammalian central nervous system (CNS). Therefore, methods are needed that can help therapeutically modify microglia, monocytes, and macrophages or the cells that give rise to them to compete with endogenous microglia and partially or completely occupy the CNS niche. The goal of the present disclosure is to develop microglial-based therapeutics, including approaches to transplant genetically modified human microglia or related monocyte lineages or progenitor cells into patients.

BRIEF SUMMARY OF THE DISCLOSURE

It is an objective of the present disclosure to provide compositions and methods that allow for differential resistance to CSF1R antagonists (e.g., partial; complete; increase; decrease) for the treatment of neurological diseases.

Microglia rely on CSF1R signaling via two ligands (CSF1 and IL-34) for survival, proliferation, and self-renewal. Treatment of mammalian models with various CSF1R antagonists reduces the number of microglia within the central nervous system. Furthermore, when these compounds are removed, surviving microglia proliferate and rapidly refill the niche. Additionally, it has been found that human stem cell-derived microglia transplanted into the murine brain are also susceptible to and killed by CSF1R inhibition (FIG. 11F, 11G, 11H, 11I, 11J).

To compete with the endogenous microglia niche, therapeutic microglia, monocytes, macrophages, or their progenitors or precursors would need to have a selective advantage in comparison to endogenous brain resident microglia in their response to CSF1R inhibitors. Specifically, one would need to develop therapeutic cells that do not die at a given dose of CSF1R inhibitor that is sufficient to kill endogenous microglia. In some instances, this selective advantage should be only partial so that a higher dose of CSF1R inhibitors could also kill therapeutic microglia, macrophages, monocytes, or their progenitors or precursors should the need arise for safety purposes.

In some embodiments, the present disclosure features a cell (e.g., a modified human cell) comprising a nucleic acid encoding a modified CSF1R protein (e.g., a human CSF1R protein) exhibiting differential resistance to a CSF1R antagonist. In other embodiments, the present disclosure features a modified human cell exhibiting differential resistance to a CSF1R antagonist. In further embodiments, the present disclosure features a modified human cell comprising a nucleic acid encoding a modified CSF1R protein exhibiting differential resistance to a CSF1R antagonist.

In some embodiments, the present disclosure may also feature a method of treating a subject. In some embodiments, the method may comprise administering a CSF1R antagonist to the subject in a quantity sufficient to inhibit a CSF1R signal in a cell of the subject and contacting the subject with a modified CSF1R-expressing cell (e.g., a modified CSF1R-expressing phagocyte) having a differential resistance to the CSF1R antagonist. In other embodiments, the method may comprise contacting the subject with a modified CSF1R-expressing cell (e.g., a modified CSF1R-expressing phagocyte) having a differential resistance to a CSF1R antagonist and administering the CSF1R antagonist to the subject in a quantity sufficient to inhibit a CSF1R signal in a cell of the subject.

In further embodiments, the present disclosure also features a method of treating a subject. The method comprises contacting the subject with a modified CSF1R-expressing cell (e.g., a modified CSF1R-expressing phagocyte) and differentially altering the proliferation or survival of an unmodified CSF1R-expressing cell (e.g., a modified CSF1R-expressing phagocyte) relative to the modified CSF1R-expressing cell (e.g., a modified CSF1R-expressing phagocyte).

In some embodiments, the present disclosure may further feature a nucleic acid composition and vectors encoding a modified CSF1R protein exhibiting differential resistance to a CSF1R antagonist as described herein.

Technical features of the present disclosure include the use of differential resistance to CSF1R antagonists (e.g., partial, complete, increased, or decreased resistance) to create therapeutic microglia, macrophages, monocytes, or their progenitors or precursors for the treatment of neurological diseases. Without wishing to limit the disclosure to any theory or mechanism, it is believed that the technical feature of the present disclosure advantageously provides for the generation of microglia, monocytes, HSPCs (hematopoietic stem or progenitor cells), or primitive macrophages from pluripotent stem cells with differential resistance to CSF1R antagonists (e.g., CSF1R antagonist resistance). As described herein, without some form of conditioning or selective advantage, transplantation of the aforementioned cells will likely exhibit only partial or limited engraftment into the central nervous system (CNS). The present disclosure develops the currently described approach that will significantly facilitate the therapeutic engraftment of microglia, macrophages, or monocytes or their progenitors (HSPCs, PMPs) in the mammalian brain. None of the presently known prior references or work has the unique, inventive technical feature of the present invention.

The compositions and methods of this disclosure represent a significant departure from the current paradigm for the use of CSF1R antagonists in medicine. For example, the prior art teaches the use of a CSF1R inhibitor to clear endogenous microglia and facilitate the entry of bone marrow- and/or blood-derived monocytes into the brain. However, bone marrow- and/or blood-derived monocytes that infiltrate the brain remain functionally and transcriptionally distinct from microglia even many months after infiltration. Additionally, the bone marrow- and/or blood-derived monocytes do not have the same sensitivity to CSF1R antagonists as microglia, demonstrating that these cells are not microglia. This teaches away from the present disclosure, which facilitates the expansion of therapeutic microglia (e.g., human microglia) comprising a modified CSF1R protein for the treatment of neurological diseases.

Additionally, most major pharmaceutical companies have developed CSF1R antagonists compounds for the treatment of some forms of cancer. However, endogenous microglia are extremely sensitive to CSF1R antagonists and will die in response to treatments with higher doses of these compounds. This is true of human stem cell-derived microglia transplanted into the murine brain (FIG. 11F, 11G, 11H, 11I, 11J). and cultured human microglia as well (FIGS. 4A, 4B, 4C, 4D, and 4E). Paradoxically, the present disclosure utilizes compounds (e.g., CSF1R antagonist) that are toxic to microglia in order to improve the long-term engraftment of transplanted microglia (e.g., transplanted therapeutic microglia; i.e., microglia comprising a modified CSF1R protein). The methods of this disclosure resolve the challenge of achieving widespread engraftment of transplanted microglia (e.g., transplanted therapeutic microglia; i.e., microglia comprising a modified CSF1R protein) in an established microglial niche that would not ordinarily be amenable to such engraftment.

Furthermore, the technical features of the present disclosure contributed to a surprising result and illustrates the unpredictability of outcomes associated with these mutations. For example, two of the proposed point mutations lead to complete (100%) protection against two CSF1R inhibitors (i.e., CSF1R antagonist) across multiple escalating doses when assessed 24 hours after inhibitor treatment (FIGS. 4A, 4B, 4C, 4D, and 4E). In contrast, a third mutation, G795V, prevented the successful differentiation of iPSCs into microglia (FIG. 1). These data demonstrate the importance of the specific DNA and resulting amino acid change that is introduced into CSF1R and that while some changes will achieve the desired resistance to CSF1R inhibitors (i.e., CSF1R antagonist), others may instead compromise the ability for microglial differentiation or survival.

Thus, the present disclosure features methods and compositions to facilitate the competitive engraftment of human microglia, macrophages, and monocytes and/or their precursor cells (HSPCs, erythromyeloid progenitors (EMPs), or Primitive Macrophage Progenitors (PMPs)). Cells can be derived from a variety of sources, including but not limited to pluripotent stem cells, including embryonic stem cells and induced pluripotent stem cells (iPSCs), bone marrow-derived hematopoietic stem cells, cord blood cells, blood-derived monocytes, fetal yolk sac or tissue macrophages, adult tissue-derived macrophages, or through direct reprogramming of another cell type into a microglia, HSPC, monocyte, or macrophage. Additionally, the present disclosure may feature methods and compositions to facilitate the competitive engraftment of CSF1R expressing cells, including but not limited to cells from the heart, skin, liver, lungs, kidney, eye, prostate, and ovary.

Any feature or combination of features described herein are included within the scope of the present disclosure provided that the features included in any such combination are not mutually inconsistent as will be apparent from the context, this specification, and the knowledge of one of ordinary skill in the art. Additional advantages and aspects of the present disclosure are apparent in the following detailed description and claims.

BRIEF DESCRIPTION OF THE SEVERAL VIEWS OF THE DRAWING(S)

The features and advantages of the present disclosure will become apparent from a consideration of the following detailed description presented in connection with the accompanying drawings in which:

FIG. 1 shows in vitro growth kinetics of control and CSF1R mutant microglia. Isogenic iPSC-derived hematopoietic progenitors were differentiated towards microglia, and cell density was used for the first 14 days. The two wild-type isogenic control lines (Cntl-1 and Cntl-2) demonstrate that some degree of variability is expected in the proliferation rates of iPSC-microglia. Both the hCSF1R G795A and G785C mutants exhibit proliferation rates that are comparable to the two control lines. In contrast, the hCSFR G794V mutant exhibits a rapid reduction in cell density, with no viable cells remaining beyond day 6 of differentiation. These data demonstrate that the specific choice of amino acid substitution is critical for the successful generation of viable microglia that can also exhibit CSF1R antagonist resistance.

FIGS. 2A, 2B, 2C, 2D, 2E, and 2F show selected CSF1R mutations have little effect on transcriptomic signature while simultaneously imparting resistance to PLX5622. FIG. 2A shows a principal component analysis using the top 2,000 genes reveals that the primary source of variation in the dataset is the WT response to PLX5622. FIG. 2B and FIG. 2C shows a linear regression analysis and calculation of the Pearson correlation coefficient between DMSO-treated MUT1 (i.e., G795A; FIG. 2B) or MUT2 (i.e., G795C; FIG. 2C) and WT microglia confirmed a high degree of concordance when examining the full transcriptome, and the 249 genes core microglial gene signature. FIGS. 2D, 2E, and 2F show a 24-hour treatment of WT (FIG. 2D), MUT1 (i.e., G795A; FIG. 2E), and MUT2 (i.e., G795C; FIG. 2F) microglia with PLX5622 induced significant transcriptomic alterations in the WT cells (FDR≤0.05; log 2(FC)≥±1) when compared to DMSO-treated cells. However, treatment of both the MUT1 and MUT2 lines failed to significantly alter gene expression, suggesting that these lines are resistant to the effects of PLX5622.

Figure 3:
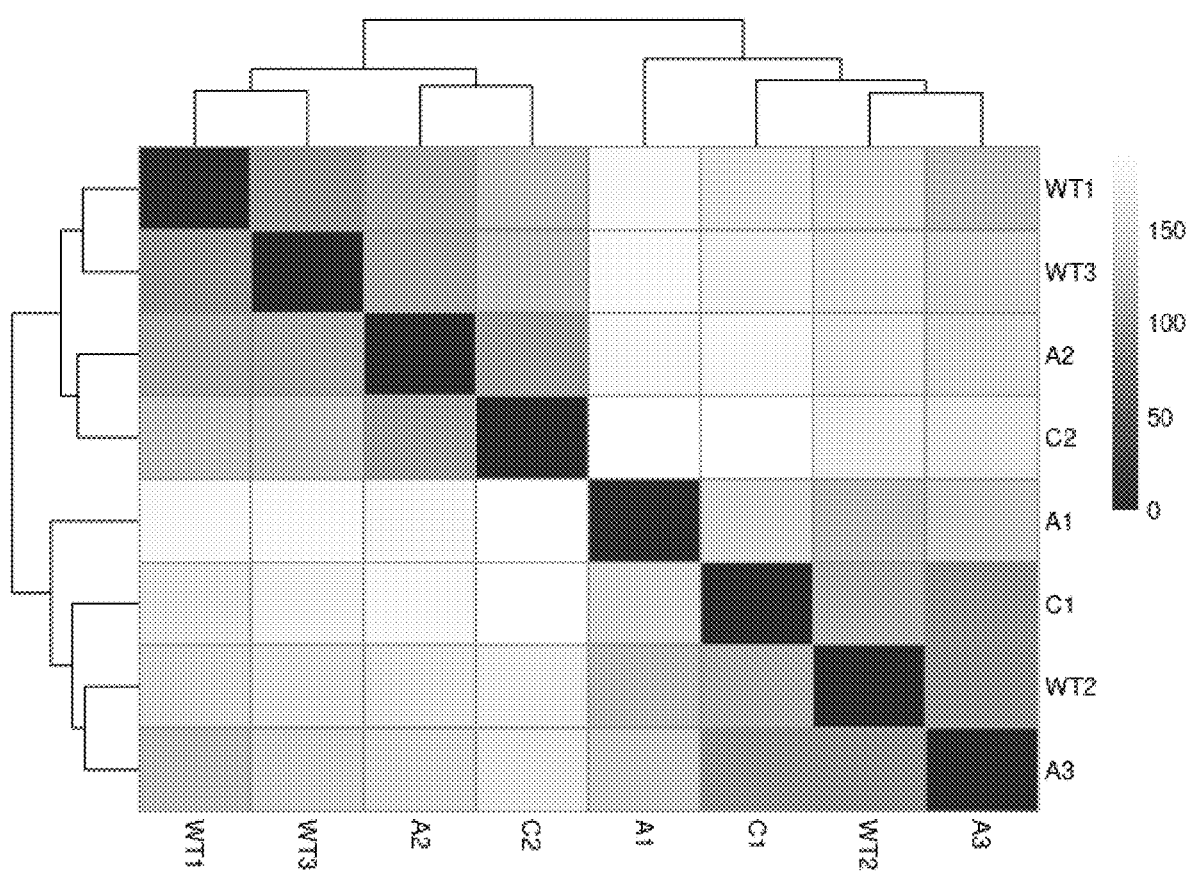

FIG. 3 shows a distance matrix of CSF1R mutants and control xMGs (microglia). RNA-seq expression counts were normalized and transformed using a variance stabilizing transformation, Pairwise Euclidean distances were calculated between all samples, and samples were hierarchically clustered by distance. These data demonstrate that the transcriptome of G795A mutant microglia is most equivalent to that of WT CSF1R microglia.

FIGS. 4A, 4B, 4C, 4D, and 4E show human stem cell-derived microglia are also susceptible to and killed by CSF1R inhibition in vitro. FIG. 4A shows caspase 3/7 levels imaged over 24 hours in culture with complete medium with 0.1% DMSO, 250 nm PLX3397, 500 nm PLX3397, and 1 μm PLX 3397. Images captured on Incucyte S3 live-cell imager. FIG. 4B shows caspase 3/7 levels imaged over 24 hours in culture with complete medium with 0.1% DMSO, 250 nm PLX5622, 500 nm PLX5622, and 1 μm PLX5622. Images captured on Incucyte S3 live-cell imager. FIG. 4C shows caspase 3/7 levels imaged over 24 hours in culture with complete medium with 0.1% DMSO, 250 nm Edicotinib (JNJ-40346527), 500 nm Edicotinib, and 1 μm Edicotinib. Images captured on Incucyte S3 live-cell imager. FIG. 4D shows caspase 3/7 levels imaged over 24 hours in culture with complete medium with 0.1% DMSO, 250 nm BLZ945, 500 nm BLZ945, and 1 μm BLZ945. Images captured on Incucyte S3 live-cell imager. FIG. 4E shows representative images of caspase 3/7 fluorescent activity for Wildtype, G795A, and G795C microglia after 24 hrs in culture with PLX3397. For all panels, n=4 images in six independent wells were quantified. Data represented as mean values±SEM.

Figure 5B:
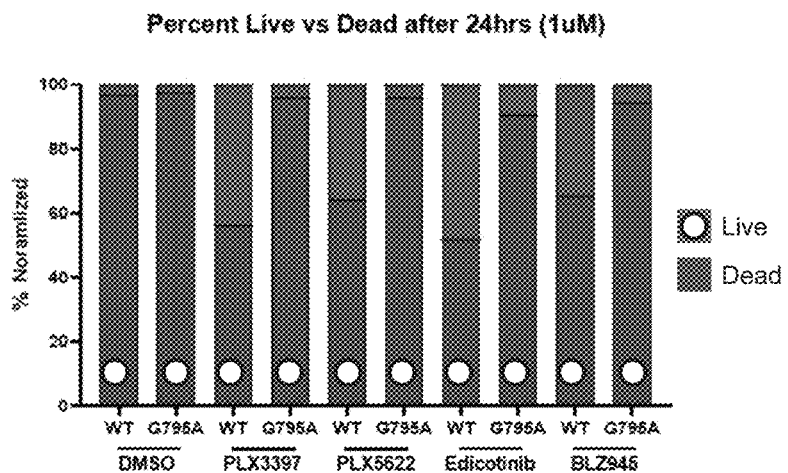

FIGS. 5A and 5B show G795A iPSC-derived microglia are resistant to CSF1R antagonist-induced cell death. As cells can die from processes other than caspase-mediated apoptosis, it is important to determine whether the G795A mutation provides a more broad-based resistance to any form of cell death induced by CSF1R antagonists. Therefore, G795A and wild-type (WT) iPSC-microglia were treated for 24 hours with either 500 nM (FIG. 5A) or 1 uM (FIG. 5B) of DMSO vehicle control or one of four CSF1R antagonists; PLX3397, PLX5622, Edicotinib, and BLZ945. The percent of live versus dead cells was then quantified using a two-color viability/cytotoxicity approach (Thermo L3224; LIVE/DEAD™ Viability/Cytotoxicity Kit). Very few dead microglia are observed 24 hours after treatment with DMSO. In contrast, treatment with CSF1R antagonists induces substantial cell death in wild-type microglia but little-to-no cell death in G795A microglia. Live cells are denoted with a circle.

Figure 6:
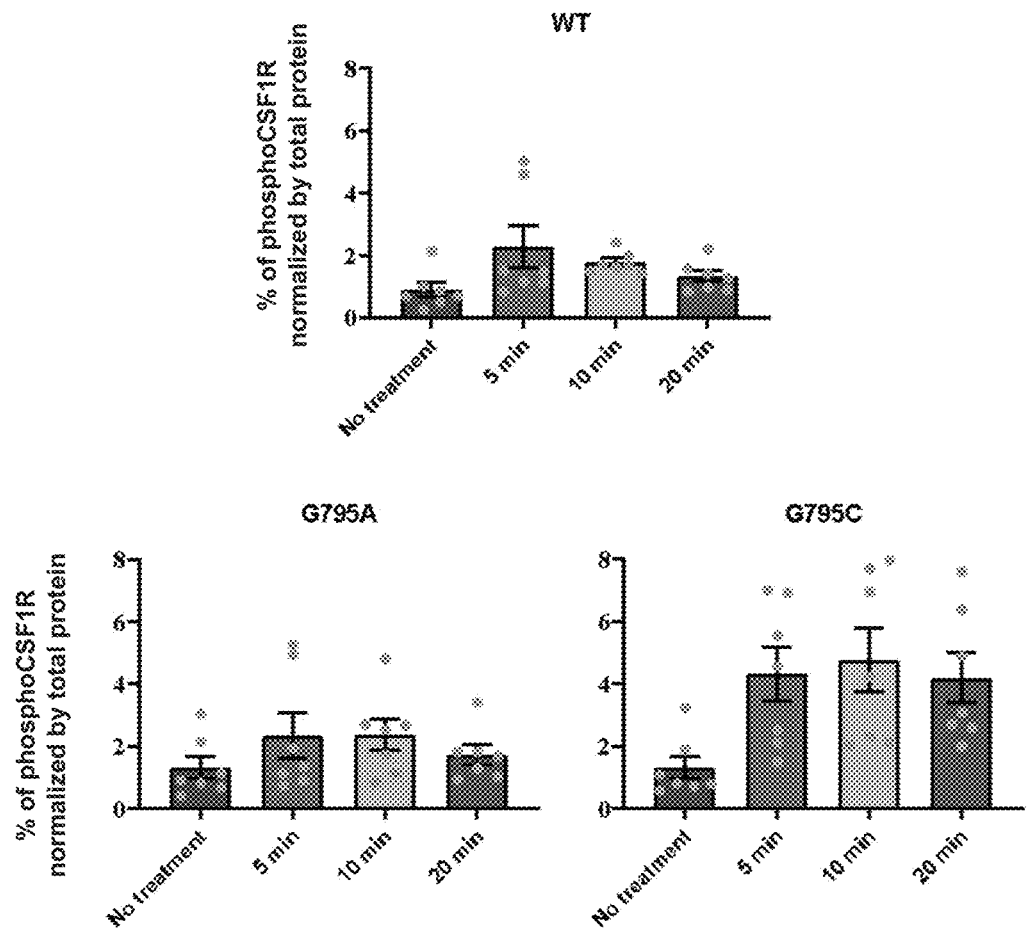

FIG. 6 shows treatment of microglia expressing mutant CSF1R with 25 ng/ml Human Macrophage Colony Stimulating Factor (Peprotech #300-25) after 48 hours stimulates tyrosine phosphorylation of CSF-1R/M-CSF-R protein, as detected by PathScan® Phospho-CSF-1R/M-CSF-R (pan-Tyr) Sandwich ELISA Kit n=7. Microglia expressing CSF1R G795A phosphorylate similarly, while microglia expressing CSF1R G795C demonstrate elevated levels of phosphorylation in comparison to WT microglia. These data suggest that whereas both G795A and G795O confer resistance to CSF1R antagonists, the G795C mutation may lead to enhanced CSF1R signaling. Data represented as mean values±SEM.

Figure 7A:
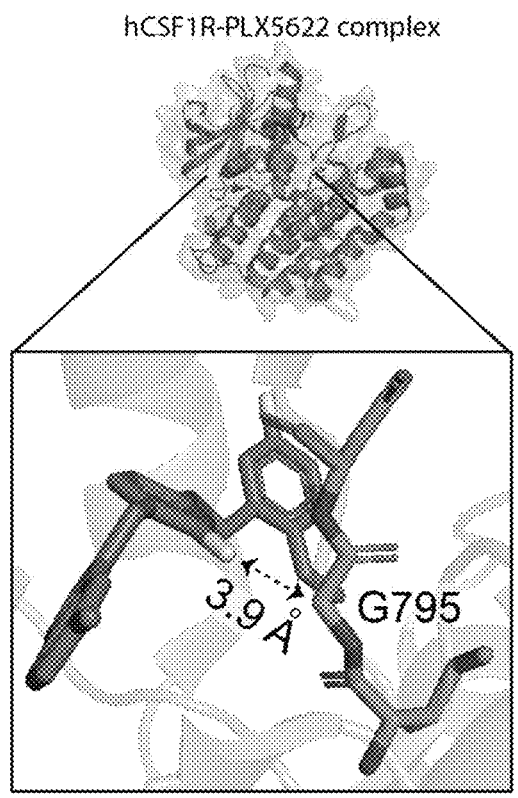
Figure 7B:
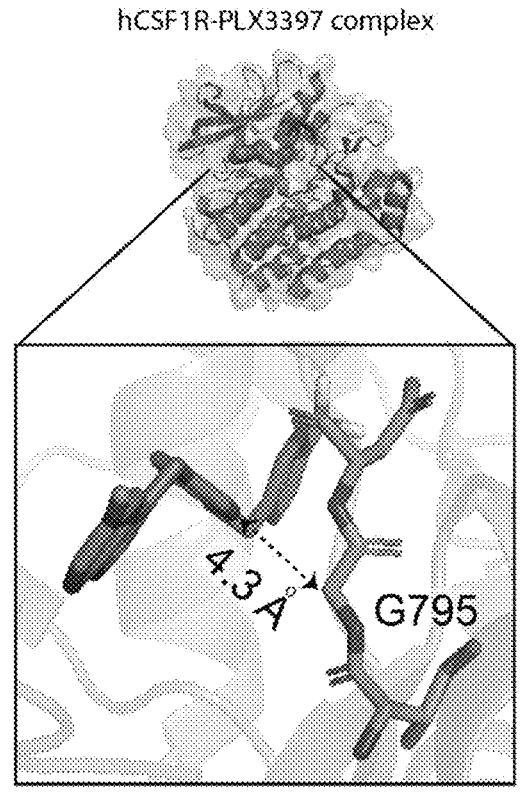
Figure 7C:
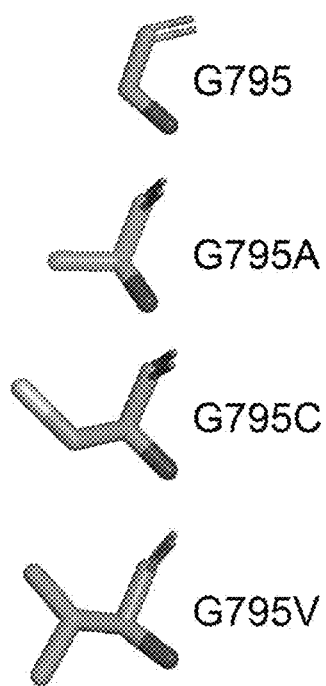
Figure 7D:
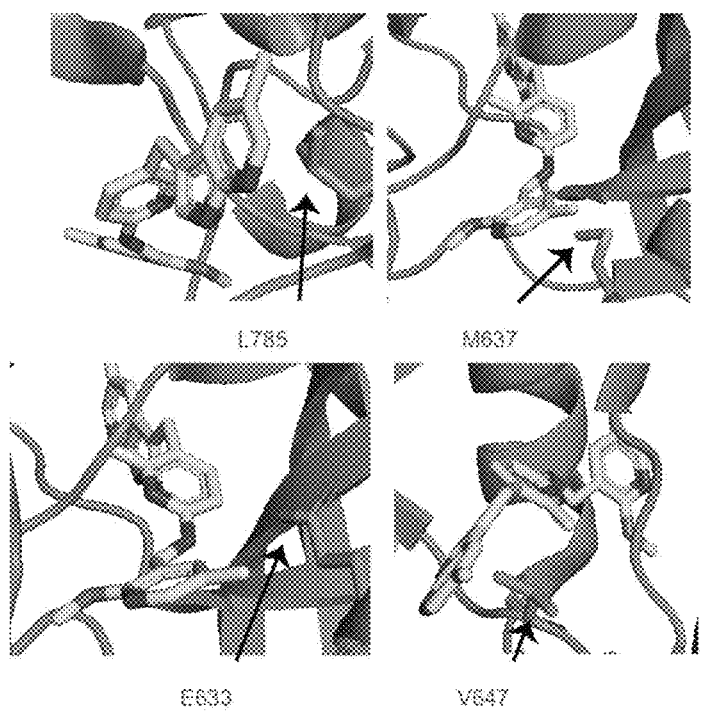

FIGS. 7A, 7B, 7C and 7D show the crystal structure of the CSF1R receptor bound to a CSF1R antagonist. FIG. 7A shows a human CSF1R receptor bound to a PLX5622 CSF1R antagonist, and FIG. 7B shows a CSF1R receptor bound to a PLX3397CSF1R antagonist. The crystal structure was examined to predict amino acid substitutions that may sterically hinder the binding of CSF1R antagonists while not impairing the normal binding of ATP into the same binding pocket. The crystal structure of the CSF1R antagonist PLX5622 (FIG. 7A) or PLX3397 (FIG. 7B) bound to human CSF1R was previously published. Using this publicly available data, the ATP binding pocket was examined. Through molecular modeling, single amino acid changes were predicted (FIG. 7C) that would likely impair the binding of PLX5622 or PLX3397 or other CSF1R antagonists while not disrupting normal ATP binding to CSF1R. Specifically, this modeling suggests that replacement of amino acid G795 with either an Alanine (A), Valine (V), or Cysteine (C) will increase the steric hindrance of PLX5622 and/or PLX3397 binding without disrupting the normal ability of ATP to bind. Other mutations could also be explored to prevent binding (FIG. 7D).

Figure 8:
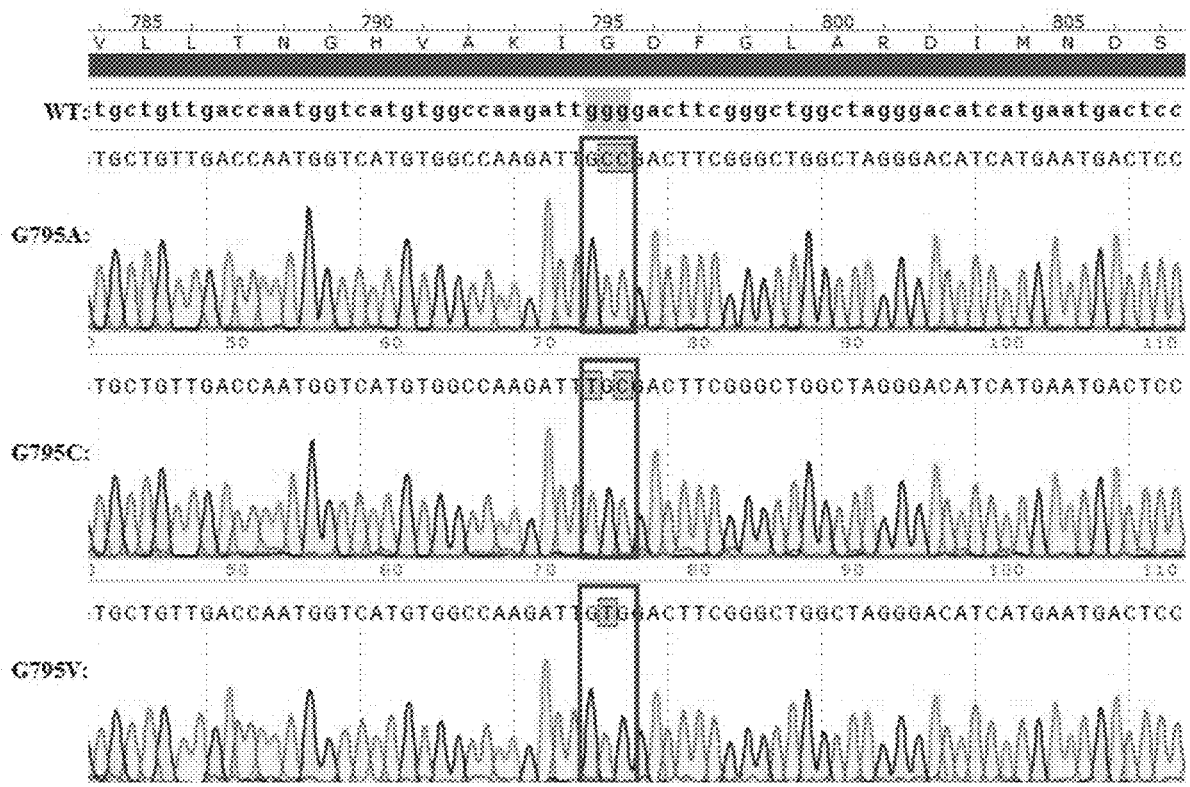

FIG. 8 shows DNA chromatograms demonstrate the successful production of isogenic human iPSC cell lines that encode single amino acid point mutations at position 795 within the CSF1R coding sequence. In this particular case, each line was generated via CRISPR-mediated gene editing. However, similar changes could be introduced via various other gene-editing methods, including but not limited to TALENs, traditional homologous recombination, viral gene delivery, or other CRISPR variants.

Figure 9A:
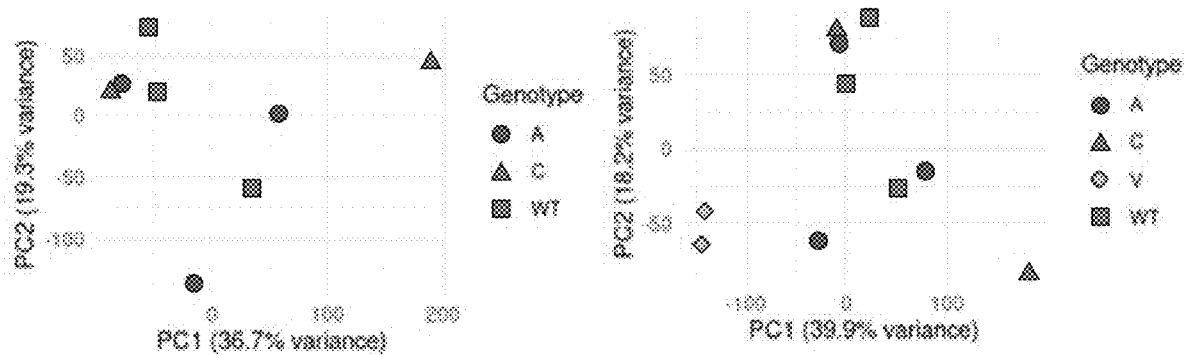
Figure 9B:
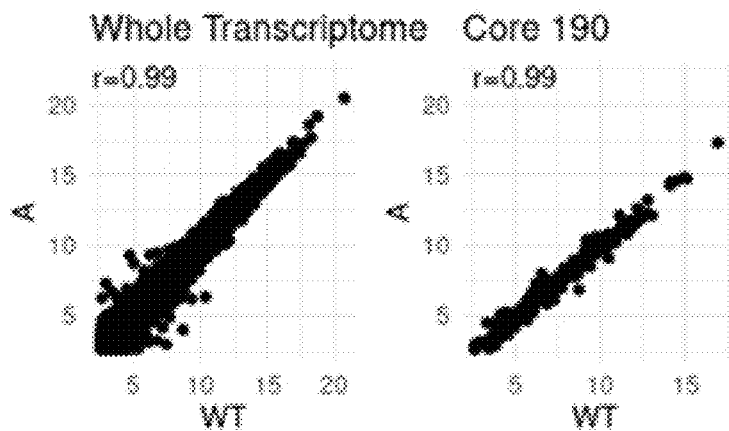
Figure 9C:
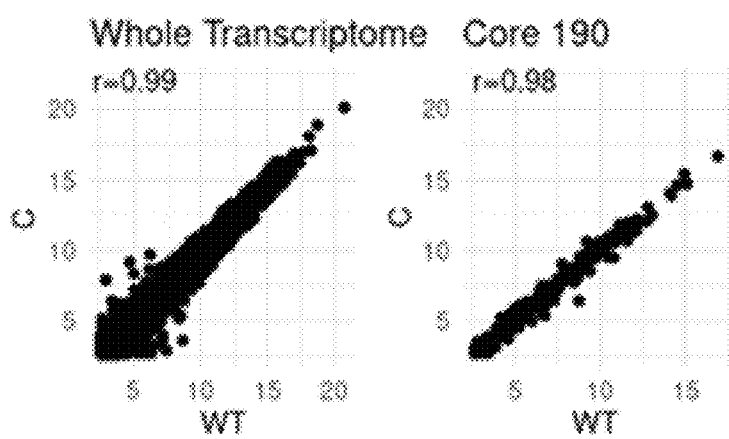
Figure 9D:
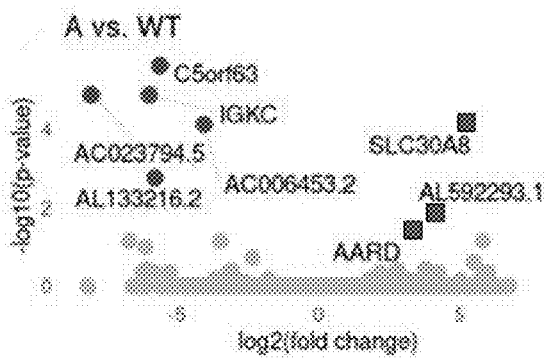
Figure 9E:
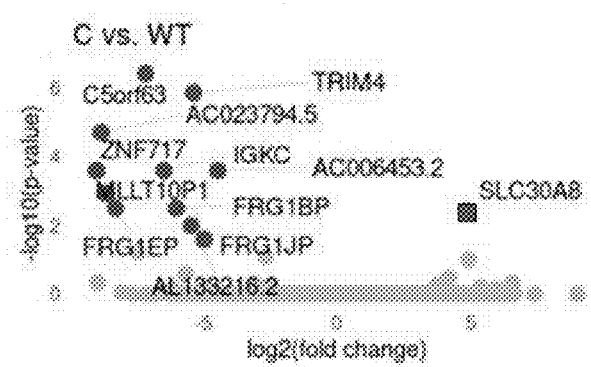

FIGS. 9A, 9B, 9C, 9D, and 9E show selected CSF1R mutations have little effect on transcriptomic signature in vivo. FIG. 9A shows a principal component analysis using the top 2,000 genes reveals that the primary source of variation between G795A, G795C, and WT microglia is attributed to individual animals and not CSF1R mutations. In contrast, when G795V is compared there is some separation based on this mutation, further indicating that G795V may not enable the generation of microglia without substantially altering gene expression. FIGS. 9B and 9C show a linear regression analysis and calculation of the Pearson correlation coefficient between G795A (FIG. 9B) or G795C (FIG. 9C) and WT microglia confirmed a high degree of concordance when examining the full transcriptome and the 190 genes core microglial signature. FIGS. 9D and 9E show a volcano plot of human microglia explanted 2-months post-transplantation in MITRG mice exhibit minimal significant transcriptomic alterations in the mutant cells (FDR≤0.05; log 2(FC)≥±1) when compared to WT cells.

Figure 10A:
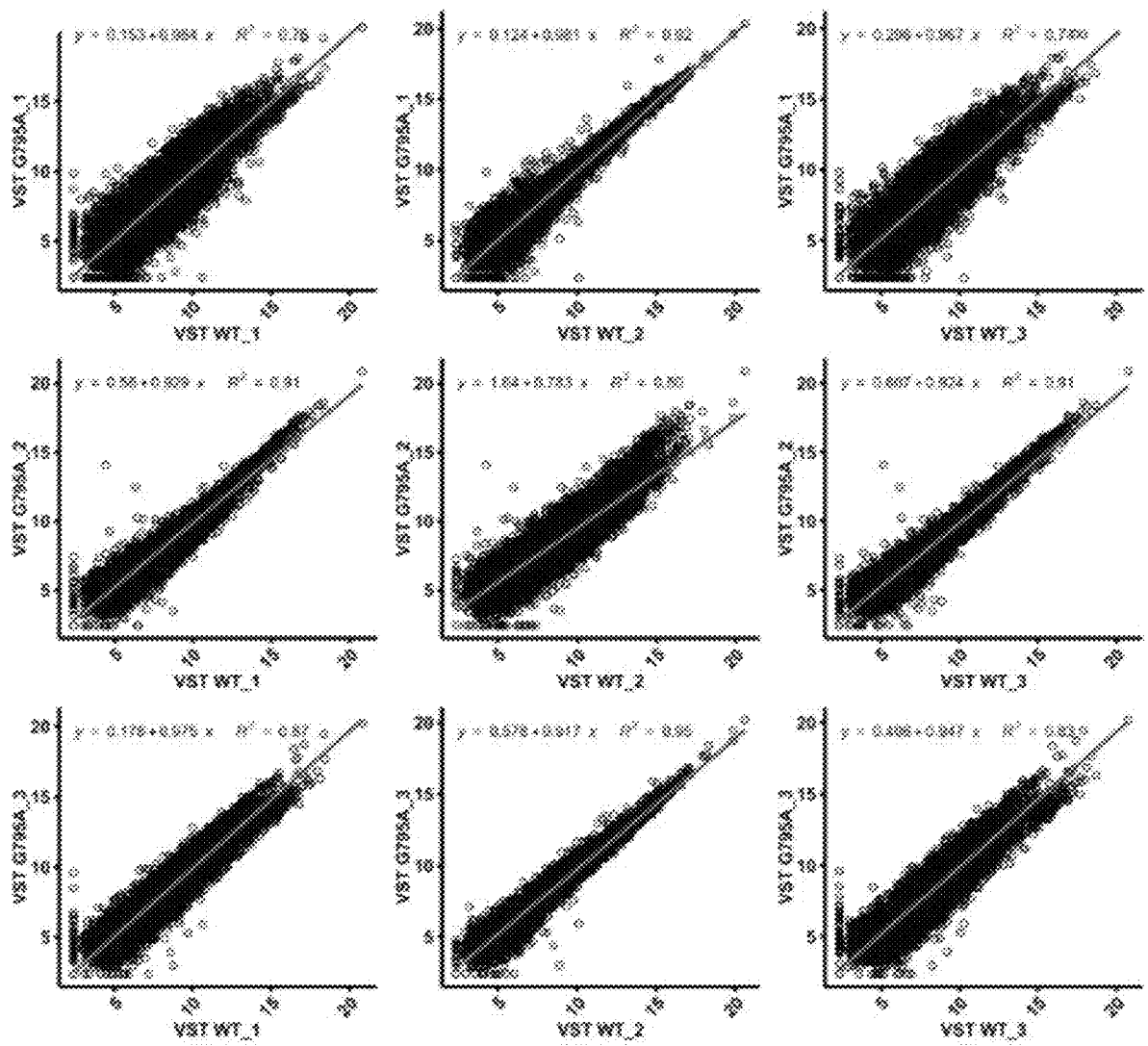
Figure 10B:
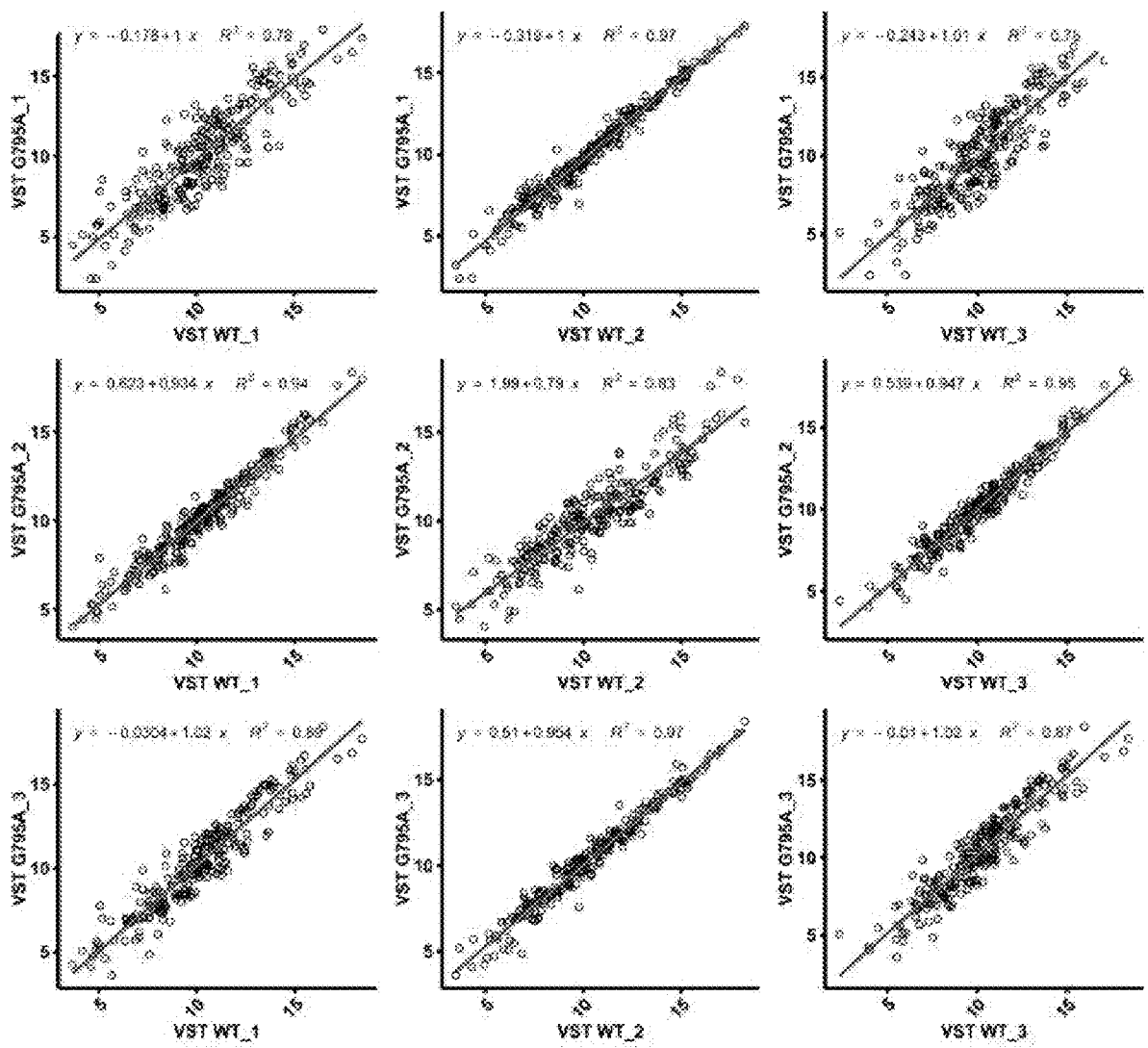

FIGS. 10A and 10B show G795A iPSC-derived microglia exhibit transcriptome signatures following xenotransplantation in vivo that are highly similar to that of isogenic wild-type iPSC-derived microglia. Xenotransplantation-compatible mice were engrafted with either wild-type (WT) or G795A iPSC-microglia, and after two months, human cells were isolated and examined via bulk RNA sequencing. FIG. 10A shows a correlation across all detected genes is shown for xMGs isolated from individual WT and G795A engrafted mice. Differences between individual mouse recipients lead to some variability, but WT and G795 xMGs remain highly correlated with $R^2$ between 0.80 and 0.95. FIG. 10B shows a similar comparison was performed using a more selected microglial-specific gene list. This comparison likewise revealed strong correlations between wild-type and G795A xMGs with $R^2$ between 0.78 and 0.97. Consistent with prior in vitro RNA-sequencing analysis, these results demonstrate that the G795A CSF1R mutation has little to no effect on the underlying transcriptome of human microglia following in vivo engraftment and that most of the detected variance is due to differences between individual mouse graft recipients.

Figure 11E:
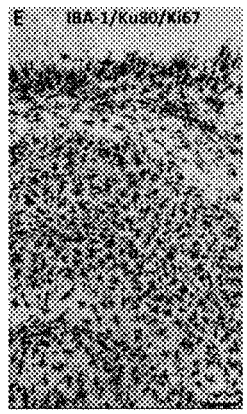

FIGS. 11A, 11B, 11O, 11D, 11E, 11F, 11G, 11H, 11I, and 11J show G795A iPSC-derived microglia are resistant to CSF1R agonist treatment and enable robust engraftment of human microglia within the adult mammalian brain. Xenotransplantation-compatible mice received bilateral stereotactic intrahippocampal injections of 500,000 iPSC-derived human microglia (xMGs) at 2-months of age. Mice received xMGs differentiated from either a homozygous CSF1R-resistant G795A human IPSO line or an isogenic unmodified Wad-Type human iPSC. At fours of age, mice were treated with 600 mg/kg of PLX3397 in rodent chow ad libitum for 4 weeks duration. Mice were then sacrificed, and half-brains were examined by fluorescent immunohistochemistry and confocal microscopy. FIG. 11A-11E shows that over the course of one-month PLX3397 treatment, G795A xMGs proliferate and expand from the initial injection sites within the hippocampus and cortex. Microglia are labeled with IBA-1 (FIGS. 11A and 11F), human-specific marker Ku80 (FIGS. 11B and 11G) is used to co-label the nuclei of human microglia, and Ki67 (FIGS. 11C and 11H) is used to demonstrate 'wavefronts' of proliferative human xMGs migrating toward remaining unoccupied niches within the cortex and thalamus (arrows). FIG. 11E shows a higher power image of the boxed region in FIG. 11D demonstrates that all IBA1+ microglia co-express Ku80. In contrast, only a handful of wild-type human xMGs survive one month of PLX3397 treatment (FIG. 11F-11I). For example, the arrows in FIG. 11J reveals just four surviving xMGs within the boxed region shown in FIG. 11I.

FIG. 12 shows quantification of CSF1R-G795A human iPSC-microglial engraftment following transplantation into adult hCSF1 mice, Transplantation of CSF1R-G795A iPSC-microglia into a fully occupied adult microglial niche (without treatment with CSF1R antagonists), produces very limited engraftment of human microglia (5-10% of total microglia) as measured by co-localization of the microglial marker IBA1 and the human-specific nuclear marker Ku80 (Ku80+/Iba1+). In contrast, when CSF1R-G795A iPSC-microglia transplantation is followed with treatment of mice for 10 days with PLX3397 containing mouse chow (600 mg/kg PLX3397 in food), the percent of human microglia increases to almost 25%. After 30 days of PLX3397 treatment (600 mg/kg PLX3397 in food), 90-95% of all microglia in the brain are human as evidenced by co-expression of Ku80 and IBA1. By transplanting CSF1R-G795A iPSC-microglia and varying the concentration and duration of CSF1R antagonist treatment either before, during, or after transplantation, one can control the degree of human iPSC-microglial engraftment.

DETAILED DESCRIPTION OF THE DISCLOSURE

Although embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. Moreover, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described herein.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Terms

As used herein, a "CSF1R expressing cell" may refer to cells that express CSF1R or cells that may be induced to express CSF1R or cells that are differentiated into cells that express CSF1R. Non-limiting examples of CSF1R-expressing cells may include but are not limited to microglia, monocytes, HSPCs (hematopoietic stem or progenitor cells), macrophages, dendritic cells, Langerhans cells, Kupffer cells, Hofbauer cells, Extravillous trophoblasts, phagocytes, or primitive macrophages from pluripotent stem cells. Additionally, a CSF1R expressing cell may refer to microglia that has been directly reprogrammed from iPSCs, monocytes, or fibroblasts via either genetic or small molecule approaches.

As used herein, "CSF1R expressing phagocyte" may refer to a cell that expresses the CSF1R receptor and has the capacity for phagocytosis; the process by which a cell uses its plasma membrane to engulf extracellular particles or bacteria, substrates, proteins, lipids, or aggregates and then internalizes this region to form a phagosome. Non-limiting examples of CSF1R-expressing phagocytes may include but are not limited to microglia, macrophages, monocytes, dendritic cells, or other phagocytes. In some embodiments, a CSF1R-expressing phagocyte is a CSF1R-expressing cell.

As used herein, "differential resistance" may refer to a state occurring in a modified cell in which the inhibition by a CSF1R antagonist of a CSF1R signal exhibits a different dose-response relationship or magnitude of response than is observed in an unmodified cell. In other embodiments, differential resistance may refer to altering the proliferation or survival of an unmodified CSF1R-expressing cell relative to the modified CSF1R-expressing cell. In some embodiments, differential resistance may comprise a partial, complete, increased, or decreased resistance to a CSF1R antagonist.

As used herein, "CSF1R signal inhibition" may refer to a dose-dependent reduction caused by a CSF1R antagonist in a step of a CSF1R signaling cascade, such as phosphorylation or dephosphorylation events, gene expression, etc.

As used herein, "partial resistance" refers to modified cells that are still destroyed by higher doses of CSF1R antagonist. Partial resistance could be due to increased binding constant (Kd) or ATP, reduced kinase activity, reduced binding affinity to CSF1 ligand, or reduced signal transduction.

As used herein, "complete resistance" refers to modified cells in which CSF1R signal inhibition never occurs at any concentration of the antagonist.

As used herein, an "increased resistance" refers to modified cells in which CSF1R signal inhibition occurs at an increased concentration of the antagonist relative to what is observed in unmodified cells.

As used herein, a "decreased resistance" refers to modified cells in which CSF1R signal inhibition occurs at a lower concentration of a receptor antagonist relative to what is observed in unmodified cells.

As used herein, the terms "subject" and "patient" are used interchangeably. As used herein, a subject can be a non-primate (e.g., cows, pigs, horses, cats, dogs, rats, mice, etc.) or a primate (e.g., monkey, ape, and human). In specific embodiments, the subject is a human. In one embodiment, the subject is a mammal (e.g., a human) having a disease, disorder, or condition described herein. In another embodiment, the subject is a mammal (e.g., a human) at risk of developing a disease, disorder or condition described herein. In certain instances, the term patient refers to a human under medical care or animals under veterinary care.

As used herein, the term "neurological diseases" refers to injuries, trauma, disorders, or diseases that affect the brain as well as the nerves found throughout the body and the spinal cord.

As used herein, the terms "treat" or "treatment" or "treating" refers to both therapeutic treatment and prophylactic or preventative measures, wherein the object is to prevent or slow the development of the disease (e.g., a neurological disease), such as slowing down the development of a disorder, or reducing at least one adverse effect or symptom of a condition, disease or disorder, e.g., any disorder characterized by insufficient or undesired organ or tissue function. Treatment is generally "effective" if one or more symptoms or clinical markers are reduced, as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of the extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" also includes ameliorating a disease, lessening the severity of its complications, preventing it from manifesting, preventing it from recurring, merely preventing it from worsening, mitigating an inflammatory response included therein, or a therapeutic effort to affect any of the aforementioned, even if such therapeutic effort is ultimately unsuccessful.

Referring now to FIG. 1-12, the present disclosure features methods and compositions for the creation and use of therapeutically designed CSF1R-expressing cells (e.g., therapeutic microglia) that have a differential resistance to CSF1R antagonists for the treatment of neurodegenerative diseases.

Cells within the central nervous system can exist inside a 'niche' which can limit the total number of cells that can reside within the mammalian CNS. The present disclosure aims to use CSF1R-expressing cells (e.g., CSF1R expressing phagocytes, HSPCs, dendritic cells, erythromyeloid progenitors, microglia, macrophages, or monocytes) to develop new treatments for neurological disease and injury. However, for some diseases, the engraftment and/or maturation of such cells within the CNS will likely be limited by the presence of existing endogenous microglia. For such indications, a method that can provide a selective survival or proliferative advantage to the transplanted mammalian cells would improve engraftment and thus therapeutic activity. Importantly, such an approach must also be safe and not induce uncontrolled proliferation.

The present disclosure features modified CSF1R-expressing cells or their progenitors or stem cells that are differentiated into cells that express CSF1R, wherein the modified CSF1R-expressing cells have differential resistance to CSF1R antagonists. Also encompassed are methods of making modified cells according to the present disclosure, which may include, in the case of an induced pluripotent stem cells (iPSC)- or hematopoietic stem and progenitor cells (HSPCs)-derived modified cell, introducing a modification into an undifferentiated cell, optionally screening or selecting for the modification, and differentiating the modified cell into a cell or cell lineages such as a monocyte or macrophage lineage.

The present disclosure features a cell (e.g., a human cell) exhibiting differential resistance to a CSF1R antagonist. In some embodiments, the present disclosure features a modified human cell exhibiting differential resistance to a CSF1R antagonist. The present disclosure may also feature a cell (e.g., a human cell) comprising a nucleic acid encoding a modified CSF1R protein exhibiting differential resistance to a CSF1R antagonist. In some embodiments, the present disclosure features a modified human cell comprising a nucleic acid encoding a modified CSF1R protein exhibiting differential resistance to a CSF1R antagonist. In some embodiments, the cell (e.g., a human cell) of the present disclosure expresses CSF1R and may be a CSF1R-expressing cell. In other embodiments, the cell (e.g., a human cell) of the present disclosure can be induced or differentiated to express CSF1R.

The present disclosure may also feature a modified cell as described herein that is expressing CSF1R. In some embodiments, the present disclosure features a modified human cell as described herein that is expressing CSF1R. The cell may be induced and/or differentiated to express CSF1R and may be selected from a group consisting of pluripotent stem cell, hematopoietic stem cell, an erythromyeloid progenitor, and hematopoietic progenitor cell.

In some embodiments, CSF1R-expressing cells (e.g., CSF1R-expressing human) cells may include but are not limited to microglia, macrophages, monocytes, or other phagocytes. In other embodiments, cells that can be induced or differentiated to express CSF1R may include but are not limited to pluripotent stem cell, hematopoietic stem cell, an erythromyeloid progenitor, or a hematopoietic progenitor cell. In some embodiments, the modified cell (e.g., the modified human cell) is a precursor cell including but not limited to microglia, monocytes, macrophages, hematopoietic progenitor cells (HPCs) and hematopoietic stem cells (HSCs), erythromyeloid progenitors (EMPs), primitive macrophages, and primitive macrophage progenitors (PMPs) or cord blood hematopoietic stem cells.

In some embodiments, the modified cells are differentially resistant to CSF1R antagonists. In some embodiments, CSF1R antagonists may include but are not limited to PLX5622, PLX3397 (pexidartinib), BLZ945, Ki20227, JNJ-40346527; JNJ-527 (Edicotinib), cFMS Receptor inhibitor 11, AZ304, ARRY-382, YM-90709, GVV2580, PLX108-01, PLX7486, PLX647, ARRY-382, JNJ-40346527, Emactuzumab (RG7155), AMG820, IMC-CS4 (LY3022855), MCS110, BPR1R024, AZD7507, JTE-952, JNJ-28312141, c-FMS-IN-8, or CSF1R-IN-22.

In other embodiments, a CSF1R antagonist may include any compound that inhibits CSF1R interaction with its cognate ligands (e.g., CSF1 or IL-34), substrates, or downstream effectors. Non-limiting examples of compounds that inhibit CSF1R interaction with its cognate ligands, substrates, or downstream effectors include but are not limited to antibodies or drugs that block the interactions between CSF1R and Phospholipase C-gamma2 (PLCg2), Spleen tyrosine kinase (Syk), and the Grb2/Gab2/Shp2 complex. In some embodiments, differential CSF1R antagonist resistance is conferred by modifying genes downstream of CSF1R. Non-limiting examples may include but are not limited to INPP5D (SHIP1), TREM2, DAP12, PLCG2, PI3K, AKT, PKC, FIMP, JNK, A-SMase, spleen tyrosine kinase (Syk), and the Grb2/Gab2/Shp2 complex. In other embodiments, partial CSF1R antagonist resistance is conferred by pretreating microglia with agonists or antagonists of CSF1R signaling. In further embodiments, CSF1R antagonists may include any compound that inhibits CSF1R signaling by blocking the ATP binding site (i.e., the ATP binding pocket).

Table 1 shows a wild type CSF1R sequence and non-limiting examples of modified CSF1R amino acid sequences (i.e., modified CSF1R protein described herein) as well as non-limiting examples of the nucleic acids sequences encoding the modified CSF1R protein described herein. Examples of such nucleic acids include those with one or more silent or conserved nucleic acid substitutions compared to the wild type nucleic acid sequence. Bolded nucleic acids (NAs) are examples of where one or more silent or conserved nucleic acid substitutions may be incorporated into the sequence. Potential nucleic acids are highlighted in the description.

| Description | Sequence | SEQ ID NO: |
|---|---|---|
| Wild Type CSF1R (nucleic acid) | atgggcccaggagttctgctgctcctgctggtggccacagcttggcatggtcagggaatcccagtgatag<br>agcccagtgtccctgagctggtcgtgaagccaggagcaacggtgaccttgcgatgtgtgggcaatggc<br>agcgtggaatgggatggcccccccatcacctcactggaccctgtactctgatggctccagcagcatcctca<br>gcaccaacaacgctaccttccaaaacacggggacctatcgctgcactgagcctggagacccctggg<br>aggcagcgccgccatccacctctatgtcaaagaccctgcccggccctggaacgtgctagcacaggag<br>gtggtcgtgttcgaggaccaggacgcactactgccctgtctgctcacagacccggtgctggaagcaggc<br>gtctcgctggtgcgtgtgcgtggccggcccctcatgcgccacaccaactactccttctcgccctggcatgg<br>cttcaccatccacagggccaagttcattcagagccaggactatcaatgcagtgccctgatgggtggcag<br>gaaggtgatgtccatcagcatccggctgaaagtgcagaaagtcatcccagggcccccagccttgacac<br>tggtgcctgcagagctggtgcggattcgaggggaggctgcccagatcgtgtgctcagccagcagcgttg<br>atgttaactttgatgtcttcctccaacacaacaacaccaagctcgcaatccctcaacaatctgactttca<br>taataaccgttaccaaaaagtcctgaccctcaacctcgatcaagtagatttccaacatgccggcaactact<br>cctgcgtggccagcaacgtgcagggcaagcactccacctccatgttcttccgggtggtagagagtgccta<br>cttgaacttgagctctgagcagaacctcatccaggaggtgaccgtgggggagggggctcaacctcaaagtc<br>atggtggaggcctacccaggcctgcaaggttttaactggacctacctgggacccttttctgaccaccagcc<br>tgagcccaagcttgctaatgctaccaccaaggacacatacaggcacaccttcaccctctctctgccccgc<br>ctgaagccctctgaggctggccgctactccttcctggccagaaacccaggaggctggagagctctgacg<br>tttgagctcacccttcgataccccccagaggtaagcgtcatatggacattcatcaacggctctggcaccct<br>tttgtgtgctgcctctgggtacccccagcccaacgtgacatggctgcagtgcagtggccacactgataggt<br>gtgatgaggcccaagtgctgcaggtctgggatgacccataccctgaggtcctgagccaggagcccttcc<br>acaaggtgacggtgcagagcctgctgactgttgagaccttagagcacaaccaaacctacgagtgcag<br>ggcccacaacagcgtggggagtggctcctgggccttcatacccatctctgcaggagcccacacgcatc<br>cccggatgagttcctcttcacaccagtggtggtcgcctgcatgtccatcatggccttgctgctgctgct<br>gctcctgctgctattgtacaagtataagcagaagcccaagtaccaggtccgctggaagatcatcgagagct<br>atgagggcaacagttatactttcatcgaccccacgcagctgccttacaacgagaagtgggagttccccg<br>gaacaacctgcagtttggtaagaccctcggagctggagcctttgggaaggtggtggaggccacggcctt<br>tggtctgggcaaggaggatgctgtcctgaaggtggctgtgaagatgctgaagtccacggcccatgctgat<br>gagaaggaggccctcatgtccgagctgaagatcatgagccacctgggccagcacgagaacatcgtca<br>accttctgggagcctgtacccatggaggccctgtactggtcatcacggagtactgttgctatggcgacctg<br>ctcaactttctgcgaaggaaggctgaggccatgctgggacccagcctgagccccggccaggaccccg<br>agggaggcgtcgactataagaacatccacctcgagaagaaatatgtccgcagggacagtggcttctcc<br>agccagggtgtggacacctatgtggagatgaggcctgtctccacttcttcaaatgactccttctctgagca<br>agacctggacaaggaggatggacggcccctggagctccgggacctgcttcacttctccagccaagtagc<br>ccagggcatggccttcctcgcttccaagaattgcatccaccgggacgtggcagcgcgtaacgtgctgttg<br>accaatggtcatgtggccaagattggggacttcgggctggctagggacatcatgaatgactccaactac<br>attgtcaagggcaatgcccgcctgcctgtgaagtggatggccccagagagcatctttgactgtgtctacac<br>ggttcagagcgacgtctggtcctatggcatcctcctctgggagatcttctcacttgggctgaatccctacc<br>ctggcatcctggtgaacagcaagttctataaactggtgaaggatggataccaaatggcccagcctgcattt<br>gccccaaagaatatatacagcatcatgcaggcctgctgggccttggagcccacccacagacccaccttc<br>cagcagatctgctccttccttcaggagcaggcccaagaggacaggagagagcgggactataccaatct<br>gccgagcagcagcagaagcggtggcagcggcagcagcagcagtgagctggaggaggagagctct<br>agtgagcacctgacctgctgcgagcaaggggatatcgcccagcccttgctgcagcccaacaactatca<br>gttctgctga | 1 |
| Wild Type CSF1R (amino acid) | MGPGVLLLLLVATAWHGQGIPVIEPSVPELVVKPGATVTLRCVGNGSVEWD<br>GPPSPHWTLYSDGSSSILSTNNATFQNTGTYRCTEPGDPLGGSAAIHLYVK<br>DPARPWNVLAQEVVVFEDQDALLPCLLTDPVLEAGVSLVRVRGRPLMRHT<br>NYSFSPWHGFTIHRAKFIQSQDYQCSALMGGRKVMSISIRLKVQKVIPGPP<br>ALTLVPAELVRIRGEAAQIVCSASSVDVNFDVFLQHNNTKLAIPQQSDFHNN<br>RYQKVLTLNLDQVDFQHAGNYSCVASNVQGKHSTSMFFRVESAYLNLSS<br>EQNLIQEVTVGEGLNLKVMVEAYPGLQGFNWTYLGPFSDHQPEPKLANAT<br>TKDTYRHTFTLSLPRLKPSEAGRYSFLARNPGGWRALTFELTLRYPPEVSV<br>IWTFINGSGTLLCAASGYPQPNVTWLQCSGHTDRCDEAQVLQVWDDPYP<br>EVLSQEPFHKVTVQSLLTVETLEHNQTYECRAHNSVGSGSWAFIPISAGAH<br>THPPDEFLFTPVVVACMSIMALLLLLLLLLLYKYKQKPKYQVRWKIIESYEG | 2 |

| Description | Sequence | SEQ ID NO: |
|---|---|---|
| | NSYTFIDPTQLPYNEKWEFPRNNLQFGKTLGAGAFGKVVEATAFGLGKED<br>AVLKVAVKMLKSTAHADEKEALMSELKIMSHLGQHENIVNLLGACTHGGPV<br>LVITEYCCYGDLLNFLRRKAEAMLGPSLSPGQDPEGGVDYKNIHLEKKYVR<br>RDSGFSSQGVDTYVEMRPVSTSSNDSFSEQDLDKEDGRPLELRDLLHFS<br>SQVAQGMAFLASKNCIHRDVAARNVLLTNGHVAKIGDFGLARDIMNDSNYI<br>VKGNARLPVKWMAPESIFDCVYTVQSDVWSYGILLWEIFSLGLNPYPGILV<br>NSKFYKLVKDGYQMAQPAFAPKNIYSIMQACWALEPTHRPTFQQICSFLQE<br>QAQEDRRERDYTNLPSSSRSGGSGSSSSELEEESSSEHLTCCEQGDIAQ<br>PLLQPNNYQFC | |
| G795A CSF1R (nucleic acid) where NNN may include: GCT, GCC, GCA, and GCG. | atgggcccaggagttctgctgctcctgctggtggccacagcttggcatggtcagggaatcccagtgatag<br>agcccagtgtccctgagctggtcgtgaagccaggagcaacggtgaccttgcgatgtgtgggcaatggc<br>agcgtggaatgggatggccccccatcacctcactggaccctgtactctgatggctccagcagcatcctca<br>gcaccaacaacgctaccttccaaaacacggggacctatcgctgcactgagcctggagaccccctggg<br>aggcagcgccgccatccacctctatgtcaaagaccctgcccggcctggaacgtgctagcacaggag<br>gtggtcgtgttcgaggaccaggacgcactactgccctgtctgctcacagacccggtgctggaagcaggc<br>gtctcgctggtcgtgtgcgtggccggccctcatgcgccacaccaactactccttctcgcctggcatgg<br>cttcaccatccacagggccaagttcattcagagccaggactatcaatgcagtgccctgatgggtggcag<br>gaaggtgatgtccatcagcatccggctgaaagtgcagaaagtcatcccagggccccagccttgacac<br>tggtgcctgcagagctggtgcggattcgaggggaggctgcccagatcgtgtgctcagccagcagcgttg<br>atgttaactttgatgtcttcctccaacacaacaacaccaagctcgcaatccctcaacaatctgactttcat<br>aataaccgttaccaaaaagtcctgaccctcaacctgcgatcagtagatttccaacatgccggcaactactc<br>ctgcgtggccagcaacgtgcagggcaagcactccacctccatgttcttccgggtggtagagagtgcctact<br>tgaacttgagctctgagcagaacctcatccaggaggtgaccgtggggagggggctcaacctcaaagtc<br>atggtggaggcctaccaggcctgcaaggttttaactggacctacctgggacccttttctgaccaccagcc<br>tgagcccaagcttgctaatgctaccaccaaggacatacagccacaccttcacctctctctgccccgc<br>ctgaagccctctgaggctggccgctactccttcctggccagaaacccaggaggctggagagctctgacg<br>tttgagctcaccttcgataccccccagaggtaagcgtcatatgggacattcatcaacggctctggcaccct<br>tttgtgtgctgcctctgggtaccccagcccaacgtgacatggctgcagtgcagtggccacactgataggt<br>gtgatgaggcccaagtgctgcaggtctgggatgaccccatacctgaggtcctgagccaggagcccttcc<br>acaaggtgacggtgcagacctgctgactgttgagaccttagagcacaaccaaacctacgagtgcag<br>ggcccacaacagcgtggggagtggctcctgggccttcatacccatctctgcaggagcccacacgcatc<br>ccccggatgagttcctcttcacaccagtggtggtcgcctgcatgtccatcatgggccttgctgctgctgctg<br>ctcctgctgctattgtacaagtataagcagaagcccaagtaccaggtccgctggaagatcatcgagagcta<br>tgagggcaacagttatactttcatcgaccccacgcagcctgcttacaacgagaagtggagttcccccg<br>gaacaacctgcagtttggtaagaccctcggagctggagcctttgggaaggtggtggaggccacggcctt<br>tggtctgggcaaggaggatgctgtcctgaaggtggctgtgaagatgctgaagtccacggcccatgctgat<br>gagaaggaggccctcatgtccgagctgaagatcatgagccacctgggccagcacgagaacatcgtca<br>accttctgggagcctgtacccatgaggccctgtactggtcactcacggcctactgttgctatgctggcgacctg<br>ctcaactttctgcgaaggaaggctgaggccatgctgggacccagcctgagccccggccaggaccccg<br>agggaggcgtcgactataagaacatccacctcgaaagaaatatgtccgcagggacagtggcttctcc<br>agccagggtgtggacacctatgtggagatgaggcctgtctccacttcttcaaatgactccttctctgagca<br>agacctggacaaggaggatgacggccctggagctccgggacgtcgttcacttctccagccaagtagc<br>ccagggcatggccttcctcgcttccaagaattgcatccaccgggacgtggcagcgcgtaacgctgcttg<br>accaatggtcatgtggccaagattNNNgacttcgggctggctagggacatcatgaatgactccaacta<br>cattgtcaagggcaatgcccgcctgcctgtgaagtggatggcccagagagcatctttgactgtgtctaca<br>cggttcagagcgacgtctggtcctatggcatcctcctctgggagatcttctcttcacttgggctgaatcccta<br>ccctggcatcctggtgaacagcaagttctataaactggtgaaggatggatgataccaaatgcccagcctgcatt<br>tgccccaaagaatatacagcatcatgcaggcctgctgggcttggagcccacccacagacccaccttt<br>ccagcagatctgctccttcttcaggagcaggcccaagaggacaggagagagcgggactataccaat<br>ctgccgagcagcagcagaagcggtggcagcggcagcagcagcagtgagctggaggaggagagct<br>ctagtgagcacctgacctgctgcgagcaaggggatatcgcccagcccttgctgcagcccaacaactatc<br>agttctgctga | 3 |
| G795A CSF1R (amino acid) | MGPGVLLLLLVATAWHGQGIPVIEPSVPELVVKPGATVTLRCVGNGSVEWD<br>GPPSPHWTLYSDGSSSILSTNNATFQNTGTYRCTEPGDPLGGSAAIHLYVK<br>DPARPWNVLAQEVVVFEDQDALLPCLLTDPVLEAGVSLVRVRGRPLMRHT<br>NYSFSPWHGFTIHRAKFIQSQDYQCSALMGGRKVMSISIRLKVQKVIPGPP<br>ALTLVPAELVRIRGEAAQIVCSASSVDVNFDVFLQHNNTKLAIPQQSDFHNN<br>RYQKVLTLNLDQVFQHAGNYSCVASNVQGKHSTSMFFRVVESAYLNLSS<br>EQNLIQEVTVGEGLNLKVMVEAYPGLQGFNWTYLGPFSDHQPEPKLANAT<br>TKDTYRHTFTLSLPRLKPSEAGRYSFLARNPGGWRALTFELTLRYPPEVSV<br>IWTFINGSGTLLCAASGYPQPNVTWLQCSGHTDRCDEAQVLQVWDDPYP<br>EVLSQEPFHKVTVQSLLTVETLEHNQTYECRAHNSVGSGSWAFIPISAGAH<br>THPPDEFLFTPVVVACMSIMALLLLLLLLLLYKYKQKPKYQVRWKIIESYEG<br>NSYTFIDPTQLPYNEKWEFPRNNLQFGKTLGAGAFGKVVEATAFGLGKED<br>AVLKVAVKMLKSTAHADEKEALMSELKIMSHLGQHENIVNLLGACTHGGPV<br>LVITEYCCYGDLLNFLRRKAEAMLGPSLSPGQDPEGGVDYKNIHLEKKYVR<br>RDSGFSSQGVDTYVEMRPVSTSSNDSFSEQDLDKEDGRPLELRDLLHFS<br>SQVAQGMAFLASKNCIHRDVAARNVLLTNGHVAKIADFGLARDIMNDSNYI<br>VKGNARLPVKWMAPESIFDCVYTVQSDVWSYGILLWEIFSLGLNPYPGILV<br>NSKFYKLVKDGYQMAQPAFAPKNIYSIMQACWALEPTHRPTFQQICSFLQE<br>QAQEDRRERDYTNLPSSSRSGGSGSSSSELEEESSSEHLTCCEQGDIAQ<br>PLLQPNNYQFC | 4 |

| Description | Sequence | SEQ ID NO: |
|---|---|---|
| G795C CSF1R (nucleic acid): where NNN may include: TGT and TGC. | atgggcccaggagttctgctgctcctgctggtggccacagcttggcatggtcagggaatcccagtgatag<br>agcccagtgtccctgagctggtcgtgaagccaggagcaacggtgaccttgcgatgtgtgggcaatggc<br>agcgtggaatgggatggccccccatcacctcactggaccctgtactctgatggctccagcagcatcctca<br>gcaccaacaacgctaccttccaaaacacggggacctatcgctgcactgagcctggagacccctggg<br>aggcagcgccgccatccacctctatgtcaaagaccctgcccggccctggaacgtgctagcacaggag<br>gtggtcgtgttcgaggaccaggacgcactactgccctgtctgctcacagacccggtgctggaagcaggc<br>gtctcgctggtgcgtgtgcgtggccggcccctcatgcgccacaccaactactcctttctcgccctggcatgg<br>cttcaccatccacagggccaagttcattcagagccaggactatcaatgcagtgccctgatgggtggcag<br>gaaggtgatgtccatcagcatccggctgaaagtgcagaaagtcatcccagggcccccagccttgacac<br>tggtgcctgcagagctggtgcggattcgaggggaggctgcccagatcgtgtgctcagccagcagcgttg<br>atgttaactttgatgtcttcctccaacacaacaacaccaagctcgcaatccctcaacaatctgactttcat<br>aataaccgttaccaaaaagtcctgaccctcaacctcgatcaagtagatttccaacatgccggcaactactc<br>ctgcgtggccagcaacgtgcagggcaagcactccacctccatgttcttccgggtggtagagagtgcctact<br>tgaacttgagctctgagcagaacctcatccaggaggtgaccgtggggagggctcaacctcaaagtc<br>atggtggaggcctaccaggcctgcaaggttttaactggacctacctgggaccttttctgaccaccagcc<br>tgagcccaagcttgctaatgctaccaccaaggacacatacaggcacaccttcaccctctctctgccccgc<br>ctgaagccctctgaggctggccgctactccttcctggccagaaacccaggaggctggagagctctgacg<br>tttgagctcacccttcgatacccccccagaggtaagctcatatggacattcatcaacggctctggcaccct<br>tttgtgctgcctctgggtaccccagcccaacgtgacatggctgcagtgcagtggccacactgataggt<br>gtgatgaggcccaagtgctgcaggtctgggatgacccataccctgaggtcctgagccaggagcccttcc<br>acaaggtgacggtgcagagcctgctgactgttgagaccttagagcacaaccaaacctacgagtgcag<br>ggcccacaacagcgtggggagtggctcctgggccttcatacccatctctgcaggagcccacacgcatc<br>ccccggatgagttcctcttcacaccagtggtggtcgcctgcatgtccatcatggccttgctgctgctgctg<br>ctcctgctgctattgtacaagtataagcagaagcccaagtaccaggtccgctggaagatcatcgagagcta<br>tgagggcaacagttatactttcatcgaccccacgcagctgccttacaacgagaagtgggagttcccccg<br>gaacaacctgcagtttggtaagaaccctcggagctggagccttggaaggtggtggaggccacggcctt<br>tggtctgggcaaggaggatgctgtcctgaaggtggctgtgaagatgctgaagttccacgccatgctgat<br>gagaaggaggccctcatgtccgagctgaagatcatgagccacctgggccagcacgagaacatcgtca<br>accttctgggagcctgtacccatggaggccctgtactggtcatcacggagtactgttgctatggcgacctg<br>ctcaacttctctgcaaggaaggctgaggccatgctgggacccagcctgagcccggccaggacccg<br>agggaggcgtcgactataagaacatccacctcgagaagaaatatgtccgcagggacagtggcttctcc<br>agccagggtgtggacacctatgtggagatgaggcctgtctccactctcttcaaatgactcctctctgagca<br>agacctggacaaggaggatggacgcccctggagctccgggacctgcttcacttctccagccaagtagc<br>ccagggcatggccttcctcgcttccaagaattgcatccaccgggacgtggcagcgcgtaacgtgctgttg<br>accaatggtcatgtggccaagattNNNgacttcgggctggcagacatcatgaatgactccaacta<br>cattgtcaagggcaatgcccgcctgctgtgaagtggatggccccagagagcatctttgactgtgtctaca<br>cggttcagagcgacgtctggtcctatggcatcctcctctgggagatcttctcacttgggctgaatccctac<br>cctggcatcctggtgaacagcaagttctataaactggtgaaggatggataccaaatggcccagcctgcatt<br>tgccccaaagaatatatacagcatcatgcaggcctgctgggcctccaccacagacccacctt<br>ccagcagatctgctccttccttcaggagcaggcccaagaggacaggagagagcgggactataccaat<br>ctgccgagcagcagcagaagcggtggcagcggcagcagcagcagtgagctggaggaggagagct<br>ctagtgagcacctgacctgctgcgagcaaggggatatcgcccagcccttgctgcagcccaacaactatc<br>agttctgctga | 5 |
| G795C CSF1R (amino acid) | MGPGVLLLLLVATAWHGQGIPVIEPSVPELVVKPGATVTLRCVGNGSVEWD<br>GPPSPHWTLYSDGSSSILSTNNATFQNTGTYRCTEPGDPLGGSAAIHLYVK<br>DPARPWNVLAQEVVVFEDQDALLPCLLTDPVLEAGVSLVRVRGRPLMRHT<br>NYSFSPWHGFTIHRAKFIQSQDYQCSALMGGRKVMSISIRLKVQKVIPGPP<br>ALTLVPAELVRIRGEAAQIVCSASSVDVNFDVFLQHNNTKLAIPQQSDFHNN<br>RYQKVLTLNLDQVDFQHAGNYSCVASNVQGKHSTSMFFRVVESAYLNLSS<br>EQNLIQEVTVGEGLNLKVMVEAYPGLQGFNWTYLGPFSDHQPEPKLANAT<br>TKDTYRHTFTLSLPRLKPSEAGRYSFLARNPGGWRALTFELTLRYPPEVSV<br>IWTFINGSGTLLCAASGYPQPNVTWLQCSGHTDRCDEAQVLQVWDDPYP<br>EVLSQEPFHKVTVQSLLTVETLEHNQTYECRAHNSVGSGSWAFIPISAGAH<br>THPPDEFLFTPVVVACMSIMALLLLLLLLLYKYKQKPKYQVRWKIIESYEG<br>NSYTFIDPTQLPYNEKWEFPRNNLQFGKTLGAGAFGKVVEATAFGLGKED<br>AVLKVAVKMLKSTAHADEKEALMSELKIMSHLGQHENIVNLLGACTHGGPV<br>LVITEYCCYGDLLNFLRRKAEAMLGPSLSPGQDPEGGVDYKNIHLEKKYVR<br>RDSGFSSQGVDTYVEMRPVSTSSNDSFSEQDLDKEDGRPLELRDLLHFS<br>SQVAQGMAFLASKNCIHRDVAARNVLLTNGHVAKICDFGLARDIMNDSNYI<br>VKGNARLPVKWMAPESIFDCVYTVQSDVWSYGILLWEIFSLGLNPYPGILV<br>NSKFYKLVKDGYQMAQPAFAPKNIYSIMQACWALEPTHRPTFQQICSFLQE<br>QAQEDRRERDYTNLPSSSRSGGSGSSSSELEEESSSEHLTCCEQGDIAQ<br>PLLQPNNYQFC | 6 |
| CSF1R G795V (nucleic acid) where NNN may include: GTT, GTC, GTA, and GTG | atgggcccaggagttctgctgctcctgctggtggccacagcttggcatggtcagggaatcccagtgatag<br>agcccagtgtccctgagctggtcgtgaagccaggagcaacggtgaccttgcgatgtgtgggcaatggc<br>agcgtggaatgggatggccccccatcacctcactggaccctgtactctgatggctccagcagcatcctca<br>gcaccaacaacgctaccttccaaaacacggggacctatcgctgcactgagcctggagacccctggg<br>aggcagcgccgccatccacctctatgtcaaagaccctgcccggccctggaacgtgctagcacaggag<br>gtggtcgtgttcgaggaccaggacgcactactgccctgtctgctcacagacccggtgctggaagcaggc<br>gtctcgctggtgcgtgtgcgtggccggcccctcatgcgccacaccaactactcctttctcgccctggcatgg<br>cttcaccatccacagggccaagttcattcagagccaggactatcaatgcagtgccctgatgggtggcag<br>gaaggtgatgtccatcagcatccggctgaaagtgcagaaagtcatcccagggcccccagccttgacac<br>tggtgcctgcagagctggtgcggattcgaggggaggctgcccagatcgtgtgctcagccagcagcgttg | 7 |

| Description | Sequence | SEQ ID NO: |
|---|---|---|
| | atgttaactttgatgtcttcctccaacacaacaacaccaagctcgcaatccctcaacaatctgactttcat<br>aataaccgttaccaaaaagtcctgaccctcaacctcgatcaagtagatttccaacatgccggcaactactc<br>ctgcgtggccagcaacgtgcagggcaagcactccacctccatgttcttccgggtggtagagagtgcctact<br>tgaacttgagctctgagcagaacctcatccaggaggtgaccgtggggagggggctcaacctcaaagtc<br>atggtggaggcctacccaggcctgcaaggttttaactggacctacctgggaccctttctgaccaccagcc<br>tgagcccaagcttgctaatgctaccaccaaggacacatacaggcacaccttcaccctctctctgccccgc<br>ctgaagccctctgaggctggccgctactccttcctggccagaaacccaggaggctggagagctctgacg<br>tttgagctcaccttcgatacccccagaggtaagcgtcatatggacattcatcaacggctctggcaccct<br>tttgtgtgctgcctctgggtaccccagcccaacgtgacatggctgcagtgcagtggccacactgataggt<br>gtgatgaggcccaagtgctgcaggtctggatgaccatcctgaggtcctgagccaggagccctcc<br>acaaggtcggtgcagagcctgctgactgttgagaccttagagcacaaccaaacctacgagtgcag<br>ggcccacaacagcgtggggagtggctcctgggccttcatacccatctctgcaggagcccacacgcatc<br>ccccggatgagttcctcttcacaccagtggtggtcgcctgcatgtccatcatggccttgctgctgctgctg<br>ctcctgctgctattgtacaagtataagcagaagcccaagtaccaggtccgctggaagatcatcgagagcta<br>tgagggcaacagttatactttcatcgaccccacgcagctgccttacaacgagaagtgggagttccccg<br>gaacaacctgcagtttggtaagaccctcggagctggagcctttgggaaggtggtggaggccacggcctt<br>tggtctgggcaaggaggatgctgtcctgaaggtggctgtgaagatgctgaagtccacggccatgctgat<br>gagaaggaggccctcatgtccgagctgaagatcatgagccacctgggccagcacgagaacatcgtca<br>accttctgggagcctgtacccatggaggccctgtactggtcatcacggagtactgttgctatggcgacctg<br>ctcaactttctgcgaaggaaggctgaggccatgctgggacccagcctgagccccggccaggaccccg<br>agggaggcgtcgactataagaacatccacctgagaagaaatatgtccgcagggacagtggcttctcc<br>agccagggtgtggacacctatgtggagatgaggcctgtctccacttcttcaaatgactccttctctgagca<br>agacctggacaaggaggatggacggccctggagctccgggacctgcttcacttctccagccaagtagc<br>ccagggcatggccttcctcgcttccaagaattgcatccaccgggacgtggcagcgcgtaacgtgctgttg<br>accaatggtcatgtggccaagattNNNgacttcgggctggctagggacatcatgaatgactccaacta<br>cattgtcaagggcaatgcccgcctgcctgtgaagtggatggcccagagagcatctttgactgtgctaca<br>cggttcagagcgacgtctggtcctatggcatcctcctctgggagatcttctcacttgggctgaatccctac<br>cctggcatcctggtgaacagcaagttctataaactggtgaaggatggataccaaatggcccagcctgcatt<br>tgccccaaagaatatatacagcatcatgcaggcctgctgggccttggagcccacccacagacccaccttt<br>ccagcagatctgctcttccttcaggagcaggcccaagaggacaggagagagcgggactataccaat<br>ctgccgagcagcagcagaagcggtggcagcggcagcagcagcagtgagctggaggaggagagct<br>ctagtgagcacctgacctgctgcgagcaaggggatatcgcccagcccttgctgcagcccaacaactatc<br>agttctgctga | |
| CSF1R<br>G795V (amino acid) | MGPGVLLLLLVATAWHGQGIPVIEPSVPELVVKPGATVTLRCVGNGSVEWD<br>GPPSPHWTLYSDGSSSILSTNNATFQNTGTYRCTEPGDPLGGSAAIHLYVK<br>DPARPWNVLAQEVVVFEDQDALLPCLLTDPVLEAGVSLVRVRGRPLMRHT<br>NYSFSPWHGFTIHRAKFIQSQDYQCSALMGGRKVMSISIRLKVQKVIPGPP<br>ALTLVPAELVRIRGEAAQIVCSASSVDVNFDVFLQHNNTKLAIPQQSDFHNN<br>RYQKVLTLNLDQVDFQHAGNYSCVASNVQGKHSTSMFFRVVESAYLNLSS<br>EQNLIQEVTVGEGLNLKVMVEAYPGLQGFNWTYLGPFSDHQPEPKLANAT<br>TKDTYRHTFTLSLPRLKPSEAGRYSFLARNPGGWRALTFELTLRYPPEVSV<br>IWTFINGSGTLLCAASGYPQPNVTWLQCSGHTDRCDEAQVLQVWDDPYP<br>EVLSQEPFHKVTVQSLLTVETLEHNQTYECRAHNSVGSGSWAFIPISAGAH<br>THPPDEFLFTPVVVACMSIMALLLLLLLLLYKYKQKPKYQVRWKIIESYEG<br>NSYTFIDPTQLPYNEKWEFPRNNLQFGKTLGAGAFGKVVEATAFGLGKED<br>AVLKVAVKMLKSTAHADEKEALMSELKIMSHLGQHENIVNLLGACTHGGPV<br>LVITEYCCYGDLLNFLRRKAEAMLGPSLSPGQDPEGGVDYKNIHLEKKYVR<br>RDSGFSSQGVDTYVEMRPVSTSSNDSFSEQDLDKEDGRPLELRDLLHFS<br>SQVAQGMAFLASKNCIHRDVAARNVLLTNGHVAKIVDFGLARDIMNDSNYI<br>VKGNARLPVKWMAPESIFDCVYTVQSDVWSYGILLWEIFSLGLNPYPGILV<br>NSKFYKLVKDGYQMAQPAFAPKNIYSIMQACWALEPTHRPTFQQICSFLQE<br>QAQEDRRERDYTNLPSSSRSGGSGSSSSELEEESSSEHLTCCEQGDIAQ<br>PLLQPNNYQFC | 8 |

In some embodiments, the cell (e.g., the modified human cell) comprises one or more genetic modifications in a gene for a CSF1R receptor (i.e., CSF1R protein). In some embodiments, the cell (e.g., the modified human cell) comprises one or more genetic modifications in a CSF1R protein (i.e., a CSF1R receptor).

In some embodiments, the one or more genetic modifications in the CSF1R receptor (i.e., CSF1R protein) do not induce constitutively active CSF1R signaling. The modified CSF1R receptor (i.e., CSF1R protein) may still be activated (e.g., phosphorylated) with a ligand of the CSF1R protein. In some embodiment, the ligand of the CSF1R protein may include but is not limited to CSF1, IL-34, a CSF1R agonist or activating antibody, or a combination thereof. In some embodiments, the modified CSF1R protein is activated by a CSF1 ligand. In some embodiments, the CSF1 ligand induces phosphorylation of the modified CSF1R protein. In other embodiments, the modified CSF1R protein is activated by an IL-34 ligand. In some embodiments, the IL-34 ligand induces phosphorylation of the modified CSF1R protein.

In some embodiments, the one or more genetic modifications result in a modified ATP binding pocket. The modified ATP binding pocket of the CSF1R receptor (i.e., CSF1R protein) may have a reduced binding space (compared to a wild type CSF1R protein). In some embodiments, the modified ATP binding pocket cannot bind a drug (e.g., a CSF1R antagonist or agonist). In other embodiments, the modified ATP binding pocket can bind ATP. In some embodiments, the one or more genetic modifications in the CSF1R receptor do not interfere with the ATP binding activity of the CSF1R protein. In some embodiments, the one or more genetic modifications in the CSF1R receptor lack a pocket for a drug (e.g., a CSF1R antagonist or agonist) to bind but do not interfere with the normal ATP binding activity of the CSF1R protein.

In some embodiments, the one or more genetic modifications is a point mutation. In some embodiments, the one or more genetic modifications result in a single amino acid substitution. In other embodiments, the one or more genetic modifications result in single amino acid insertion. In further embodiments, the one or more genetic modifications result in single amino acid deletion.

In some embodiments, the one or more genetic modifications result in a change in the amino acid sequence of the CSF1R protein. The change in the amino acid sequence may optionally comprise the substitution of an amino acid residue selected from G795, L785, M637, E633, and V647. In some embodiments, the one or more genetic modifications result in an amino acid substitution. In some embodiments, the one or more genetic modifications result in a single amino acid substitution. The single amino acid point mutations may be selected from a group consisting of G795A, G795V, and G795C.

In some embodiments, the CSF1R gene is modified to confer partial or complete resistance to the CSF1R antagonist in the modified cells. In some embodiments, the CSF1R gene is modified with a single point mutation. In other embodiments, single point mutations of the CSF1R gene may include but are not limited to these single amino acid substitutions at positions G795, L785, M637, E633, and/or V647. As non-limiting examples, the substitutions may comprise G795A, G795V, or G795C, or G795D, or G795E, or G795F, or G795G, or G795H, or G795I, or G795K, or G795L, or G795M, or G795N, or G795P, or G795Q, or G795R or G795S, or G795T, or G795W, or G795Y.

Without wishing to be bound by any theories or mechanisms, the substitution of these residues or any other amino acid residue that is in direct contact with small molecule inhibitors bound to the ATP binding site would be predicted to alter their binding. Amino acid substitutions comprising slightly larger functional groups: serine; threonine; cysteine; valine; leucine; isoleucine; and methionine are expected to introduce bulky substituents that clash with plexxikon binding yet still permit ATP binding for CSF1R function. Much larger amino acid substitutions: phenylalanine, tyrosine, lysine, arginine, and tryptophan, are expected to sterically clash with both inhibitors and ATP thereby inhibiting normal CSF1R function. By contrast, substitutions with amino acids with less bulky side chains such as glycine or alanine may improve binding to antagonist species that are only weakly bound by the native sequence due to steric hindrance by slightly larger or incompatibly polar side chains. Those of skill in the art will appreciate, then, that these and other residues that define binding sites for allosteric antagonists may be subject to modification in accordance with the object of this disclosure.

In other embodiments, the one or more genetic modifications result in a change in a plurality of amino acids of the CSF1R protein. In some embodiments, the change in a plurality of amino acids are to adjacent amino acids. In other embodiments, the change in a plurality of amino acids are to non-adjacent amino acids.

In some embodiments, the one or more genetic modifications (e.g., point mutations) are within the ATP-binding pocket of the CSF1R protein (i.e., a CSF1R receptor). In other embodiments, the one or more genetic modifications (e.g., point mutations) are outside the ATP-binding pocket of the CSF1R protein (i.e., a CSF1R receptor). Without wishing to limit the present disclosure to any theories or mechanisms, it is believed that mutations outside the ATP-binding pocket of the CSF1R protein may work through allostery to inhibit antagonist binding.

In some embodiments, the one or more genetic modifications are introduced ex vivo. In other embodiments, the one or more genetic modifications are induced by transfecting or introducing into a cell (e.g., a human cell) a nucleic acid encoding a transgene. In further embodiments, the one or more genetic modifications are introduced by transduction or introduction of a targeted nuclease, nickase, or base-editing effector or ribonucleoprotein complex. In some embodiments, introducing the nucleic acid encoding a transgene in a cell comprises contacting the cell (e.g., the human cell) with a viral vector.

In some embodiments, the one or more genetic modifications (e.g., point mutations) in the CSF1R gene are generated via site-directed or random mutagenesis methods known in the art, including, without limitation, CRISPR-Cas, TALEN, and ZFN genome editing systems. Alternatively, or additionally, modified CSF1R transgenes may be introduced into cells (e.g., human cells) by, e.g., DNA or RNA vectors such as naked nucleic acids, liposome or other encapsulated nucleic acid vectors, artificial chromosomes, and/or viral vectors such as lentiviral and adeno-associated viral vectors.

In some embodiments, cells (e.g., human cells) comprising a modified CSF1R protein as described herein retain a gene expression profile of a cell (e.g., a human cell) comprising a wild-type CSF1R protein. In some embodiments, in vitro cells (e.g., in vitro human cells) comprising a modified CSF1R protein have a similar gene expression profile as in vitro cells (e.g., in vitro human cells) comprising a wild-type CSF1R protein. In other embodiments, cells (e.g., human cells) comprising a modified CSF1R protein that are transplanted in vivo have a similar gene expression profile of a transplanted cell (e.g., human cell) that does not compromise a modified CSF1R protein. In further embodiments, modified CSF1R-expressing cells (e.g., CSF1R-expressing phagocytes) as described herein retain a gene expression profile of wild-type CSF1R-expressing cells (e.g., CSF1R-expressing phagocytes).

The present disclosure may also feature a composition comprising a CSF1R-expressing cell as described herein. The present disclosure may also feature a composition comprising a CSF1R-expressing phagocyte as described herein. In some embodiments, the composition comprises a plurality of cells. In some embodiments, at least 0.1%, at least 1%, at least 5%, at least 10%, at least 20%, at least 30%, at least 40, at least 50%, or at least 60%, or at least 70%, or at least 80%, or at least 90%, or at least 99% or at least 99.5% of the plurality of cells are CSF1R-expressing cells having differential resistance to a CSF1R antagonist. In other embodiments, at least 0.1%, at least 1%, at least 5%, at least 10%, at least 20%, at least 30%, at least 40, at least 50%, or at least 60%, or at least 70%, or at least 80%, or at least 90%, or at least 99% or at least 99.5% of the plurality of cells are CSF1R-expressing phagocytes having differential resistance to a CSF1R antagonist.

The present disclosure features a method of treating a subject. The method comprises administering a CSF1R antagonist to the subject in a quantity sufficient to inhibit a CSF1R signal in a cell of the subject and contacting the subject with a modified CSF1R-expressing cell (e.g., a modified CSF1R-expressing phagocyte) having a differential resistance to a CSF1R antagonist. In other embodiments, the method comprises contacting the subject with a modified CSF1R-expressing cell (e.g., a modified CSF1R-expressing phagocyte) having a differential resistance to a CSF1R antagonist and administering the CSF1R antagonist to the subject in a quantity sufficient to inhibit a CSF1R signal in a cell of the subject. In some embodiments, differential resistance to the CSF1R antagonist is partial resistance or complete resistance to the CSF1R antagonist.

The modified CSF1R-expressing cells (e.g., modified human CSF1R-expressing cells) described herein may further comprise one or more modifications (e.g., one or more genetic modifications in another gene (e.g., outside of the CSF1R gene). In some embodiments, the modified CSF1R-expressing cell (e.g., a modified CSF1R-expressing phagocyte) expresses a gene product useful to treat, cure, ameliorate, prevent or palliate a neurological disease. In some embodiments, the gene product is not otherwise expressed by the CSF1R-expressing cell (e.g., a modified CSF1R-expressing phagocyte). In other embodiments, the modified CSF1R-expressing cell (e.g., a modified CSF1R-expressing phagocyte) expresses other genetic modifications useful to treat, cure, ameliorate, prevent or palliate a neurological disease. In other embodiments, other genetic modifications (outside of the CSF1R gene) are used to correct a mutated gene to treat a disease caused by mutations in that other gene.

In some embodiments, the CSF1R signal that is inhibited by the CSF1R antagonist is the proliferation or survival of a CSF1R-expressing cell (e.g., a CSF1R-expressing phagocyte) that is endogenous to the subject. In other embodiments, the CSF1R antagonist is administered to the subject in a quantity sufficient to reduce the proliferation or survival of the endogenous CSF1R-expressing cell (e.g., a CSF1R-expressing phagocyte) of the subject relative to the modified CSF1R-expressing cell (e.g., a modified CSF1R-express phagocyte).

The present disclosure may also feature a method of treating a subject. The method may comprise contacting the subject with a modified CSF1R-expressing cell (e.g., a modified CSF1R-expressing phagocyte) and differentially altering the proliferation or survival of an unmodified CSF1R-expressing cell (e.g., an unmodified CSF1R-expressing phagocyte) relative to the modified CSF1R-expressing cell (e.g., a modified CSF1R-expressing phagocyte). In some embodiments, the modified CSF1R-expressing cell (e.g., a modified CSF1R-expressing phagocyte) is partially resistant to a CSF1R antagonist. In some embodiments, the step of differentially altering the proliferation or survival of the unmodified CSF1R-expressing cell (e.g., an unmodified CSF1R-expressing phagocyte) comprises administering the CSF1R antagonist to the subject in a quantity sufficient to reduce proliferation or survival of the unmodified CSF1R-expressing cell (e.g., an unmodified CSF1R-expressing phagocyte) relative to the modified CSF1R-expressing cell (e.g., a modified CSF1R-expressing phagocyte).

The methods described herein may kill about 0.1%, or about 1%, or about 5%, or about 10%, or about 20%, or about 30%, or about 40%, or about 50%, or about 60%, or about 70%, or about 80%, or about 90%, or about 99%, or about 99.5% of endogenous CSF1R-expressing phagocyte within the CNS of the subject. In other embodiments, the methods described herein may kill all the endogenous CSF1R-expressing phagocytes within the CNS of the subject.

The methods described herein may further allow for the engraftment of about 0.1%, or about 1%, or about 5%, or about 10%, or about 20%, or about 30%, or about 40%, or about 50%, or about 60%, or about 70%, or about 80%, or about 90%, or about 99%, or about 99.5% of the modified CSF1R-expressing phagocyte within the CNS of the subject. In some embodiments, the methods described herein allow for complete engraftment of the modified CSF1R-expressing phagocyte within the CNS of the subject.

In some embodiments, the methods described herein are directed towards treating, preventing, palliating, or ameliorating a neurological disease by contacting a subject with a modified cell or vector of this disclosure. In some embodiments, a neurological disease comprises a disease of the nervous system. Non-limiting examples of neurological diseases may include but are not limited to dementia, a neurodegenerative disease, a genetic disease, a spinal cord injury, a traumatic brain injury, a disease caused or worsened by exposure to a chemical or other agent, etc.

The present disclosure may also feature a composition for the treatment of neurological disease, the composition comprising a plurality of modified cells having differential (e.g., increased, decreased, partial or complete) resistance to CSF1R antagonists. In some embodiments, the modified cells are CSF1R-expressing cells.

The present disclosure may further feature nucleic acid compositions and vectors encoding a modified CSF1R protein exhibiting differential resistance to a CSF1R antagonist as described herein. In some embodiments, the nucleic acid compositions and vectors may include a payload including but not limited to a transgene, a marker or reporter gene, etc. In some embodiments, the expression vector comprises a nucleic acid composition as described herein operably linked to an expression control sequence.

In some embodiments, the nucleic acid composition comprises a modified CSF1R protein exhibiting differential resistance to a CSF1R antagonist. In some embodiments, the differential resistance to the CSF1R antagonist is partial resistance, complete, increased, or decreased resistance to the CSF1R antagonist.

In other embodiments, the nucleic acid composition comprises a modified CSF1R protein comprising one or more genetic modifications. In some embodiments, the one or more genetic modifications result in an amino acid substitution which is selected from a group consisting of G795A, G795V, G795C, L785, M637, E633, and V647.

In some embodiments, the present disclosure features an expression vector comprising a nucleic acid composition comprising a modified CSF1R protein exhibiting differential resistance to a CSF1R antagonist.

In some embodiments, the expression vectors described herein may be used to modify cultured or endogenous cells. In some embodiments, the expression vectors described herein are used to transfect a cultured cell, such that the culture cell or the progeny of said cell express the polypeptide. In other embodiments, the expression vectors described herein are used to modify an endogenous CSF1R-expressing cell by transducing the nucleic acid (e.g., by infecting with the viral vector to create a CSF1R-antagonist resistant cell in situ).

Methods and compositions of the present disclosure may advantageously be used in human or veterinary applications whereby a modified cell or a vector or genome-editing-system (e.g, a CRISPR-Cas, TALEN, or ZFN system) configured to introduce a mutation of the instant disclosure and thereby create a modified cell, is used in the prevention, palliation, amelioration or cure of a disease or disorder. In general, these methods will comprise the steps of contacting a subject with a modified cell or a vector or genome editing system configured to generate such a cell and contacting the subject with a CSF1R antagonist.

Turning first to subjects for whom the methods of this disclosure may be suitable, any subject may be a candidate for treatment according to these methods, but it may be advantageous to treat those subjects who suffer from, or are predicted or predisposed to suffering from, a disease such as a neurological disease that can be prevented, palliated, ameliorated or cured by contacting the subject with a cell of the present disclosure characterized by a differential response to CSF1R antagonists relative to a native or endogenous cell of the subject. Without limiting the foregoing, a neurological disease amenable to treatment by methods of this disclosure may comprise dementia, a neurodegenerative disease, a demyelinating disease, a mood or personality disorder, a traumatic brain injury, a genetic disease, a malignant or benign tumor, a metastatic tumor, or growth, etc.

A subject can be contacted with a modified cell or a vector of the disclosure at any suitable time and by any suitable route of administration, including without limitation by intravenous, intramuscular, intraperitoneal, intraparenchymal, intrathecal, intercranial, interosseus or other injection or infusion, transdermal administration (for vectors) and/or by surgical implantation or transplantation. Any suitable number of cells or titer of the vector may be administered, e.g., $10^1$, $10^2$, $10^3$, $10^4$, $10^5$, $10^6$, $10^7$, $10^8$, etc. cells, and/or $10^{14}$, $10^{13}$, $10^{12}$, $10^{11}$, $10^{10}$, $10^9$, or fewer virions or viral genomes. With respect to modified cells, the cells with which the subject is contacted may be derived from the subject's own cells (autologous cells) or they may be from another donor (allogeneic cells).

Those of skill in the art will appreciate that the differential sensitivity of modified cells of this disclosure to CSF1R antagonists may be most clearly manifest in the presence of a CSF1R antagonist. Therefore, while the subject may be contacted at any time with a CSF1R antagonist (including without limitation as pre-treatment or conditioning treatment prior to contacting a subject with a modified cell of this disclosure), some embodiments of this disclosure comprise administering a CSF1R antagonist to a subject simultaneously with and/or following the step of contacting the subject with the modified cell or vector. The CSF1R antagonist may be administered continuously or discontinuously, and the initiation or discontinuation of the administration may be scheduled or pre-programmed, or it may be in response to a physiological readout from the subject such as a biomarker concentration, a serum or tissue concentration of a biomarker or a small molecule active ingredient or metabolite thereof, an imaging signal or sign, etc.

As one non-limiting example, in the case of a modified cell that exhibits reduced sensitivity (i.e., partial or complete resistance) to a CSF1R antagonist, said CSF1R antagonist may be administered to a subject to reduce the proliferation or survival of native cells within a niche occupied by such cells, thereby imparting a selective advantage to modified cells and optionally increasing a rate of engraftment or other behavior of the modified cells relative to that observed in the absence of the CSF1R antagonist. This administration may be initiated—and optionally terminated—prior to, simultaneously, or subsequently to the step of contacting the subject with the modified cell or vector. Without limiting the foregoing, in the case where the modified cell is a microglial cell or microglial progenitor cell, a CSF1R antagonist may be administered to a subject prior to, coincident with, and/or subsequent to the transplantation of modified microglial-lineage cells to limit the proliferation and/or survival of endogenous microglia, thereby imparting an advantage to the modified microglia which may result in a greater degree of engraftment and/or a greater spatial distribution of the modified microglia than might otherwise be observed.

Alternatively, or additionally, a modified cell of this disclosure may exhibit increased sensitivity to CSF1R antagonists relative to an unmodified cell. In this instance, the CSF1R antagonist is generally (but not necessarily) withheld before and during the step of contacting the subject with the modified cell, and instead is administered after the subject has been contacted with the modified cell or vector, for instance, to limit the proliferation or survival of the modified cells at the conclusion of a course of treatment, in response to a signal from a physiological or pharmacological measurement, and/or in response to an adverse event or a reduction in the efficacy of a therapeutic intervention utilizing the modified cells.

A modified cell of this disclosure optionally comprises one or more additional modifications relative to a native cell, of the same type. These modifications may include, without limitation, one or more transgenes, or one or more genetic modifications that correct a mutation or reduce or increase the expression of a gene product. Without limiting the foregoing, this disclosure includes a microglial cell engineered to express a CSF1R allele with reduced sensitivity to a CSF1R antagonist, and a secreted transgene such as an enzyme or a binding protein, an RNA such as antisense, miRNA, or siRNA, a cell surface protein such as a chimeric antigen receptor, a membrane-bound immunoglobulin or fragment thereof, an aptamer, etc. The disclosure also comprises vectors and methods of making such cells substantially as described above, and a method of treating a subject using a cell or vector to treat the subject.

Without wishing to limit the present disclosure to any theory or mechanism, it is believed that a variety of methods could be used to achieve the presently claimed cells that have a differential resistance to a CSF1R antagonist. Described herein are non-limiting methodologies/examples that accomplish this goal. Equivalents or substitutes are within the scope of the present disclosure.

EXAMPLE

The following is a non-limiting example of the present invention. It is to be understood that said example is not intended to limit the present invention in any way. Equivalents or substitutes are within the scope of the present invention.

To facilitate the competitive engraftment of human microglia, macrophages, and monocytes and/or their precursor cells (hematopoietic progenitor cells (HPCs) and hematopoietic stem cells (HSCs), erythromyeloid progenitors (EMPs), or Primitive Macrophage Progenitors (PMPs), several approaches could be used independently or in combination. 1) using the previously published crystal structure of the CSF1R receptor bound to an antagonist (PMID: 31434879) to predict amino acid substitutions that may sterically hinder the binding of CSF1R antagonists while not impairing the normal binding of ATP into the same binding pocket. 2) Using PCR-mediated random mutagenesis to introduce amino acid changes followed by exposure of iPS-microglia to CSF1R antagonists and then sequencing of surviving mutants to identify mutations that confer resistance to CSF1R antagonists, but which do not concurrently induce constitutively active CSF1R signaling. 3) Modifying genes downstream of CSF1R, for example, delete or transiently reduce expression of SHIP1 (INPP5D) to enhance CSF1R signal transduction. 4) Pretreat microglia being transplanted with agonists of CSF1R signaling, could also use a siRNA or microRNA gene delivery approach to modulate and transiently increase CSF1R signaling in transplanted cells to promote resistance to CSF1R antagonist treatments. Below are provided additional details and data related to the first two strategies.

Strategy 1: A crystal structure of the CSF1R receptor bound to an antagonist (PMID: 31434879) to predict amino acid substitutions that may sterically hinder the binding of CSF1R antagonists while not impairing the normal binding of ATP into the same binding pocket. The crystal structure of PLX5622 bound to human CSF1R was obtained and the ATP binding pocket was examined (FIG. 7A). Through molecular modeling single amino acid changes were predicted that would likely impair the binding of PLX5622 or PLX3397 or other CSF1R antagonists while not disrupting normal ATP binding to CSF1R. Specifically, this modeling suggests that replacement of amino acid G795 with either an Alanine (A), Valine (V), or Cysteine (C) will increase the steric hindrance of PLX5622 and/or PLX3397 binding without disrupting the normal ability of ATP to bind (FIGS. 7A and 7B). Other mutations could also be explored to prevent binding (FIG. 7D). A CRISPR targeting strategy was designed to generate human iPSCs carrying each of these single amino acid substitutions; G795A, G795V, G795C, and successfully produced these modified human iPSC lines (Sanger Sequencing Chromatograms demonstrating the edited sequences are shown in FIG. 8). The resulting iPSCs were then differentiated into microglia and exposed to varying concentrations of either PLX3397 or PLX5622. To detect microglial cell death (apoptosis) a caspase-3/7 fluorogenic reporter was used. FIG. 4A demonstrates the dose-dependent induction of cell death in wild-type (WT) unedited human iPSC-microglia versus the G795A and G795C CSF1R mutant lines in response to PLX3397 and FIG. 4B shows the response to PLX5622. Within 24 hours of PLX compound treatment WT human microglia exhibit a robust dose-dependent induction of apoptosis in response to either compound. In contrast, both the G795A and G795C mutant lines show complete resistance to cell death. FIG. 4F provided representative images of cell density (phase-contrast microscopy, $1^{st}$ column) and fluorescent Caspase-3/7 activity ($2^{nd}$ column) across each dose of PLX3397 and PLX5622.

Further inspection of the crystal structure also presents other positions which, if mutated, could result in a reduction of PLX5622 and/or PLX3397 binding. Examples include L785, M637, E633, and V647 (FIG. 4D). These positions are all within close contact to PLX5622 and/or PLX3397 binding sites and may prevent binding when mutated.

Strategy 2: PCR-mediated random mutagenesis will be used to introduce amino acid changes followed by exposure of iPS-microglia to CSF1R antagonists and then sequencing of surviving mutants to identify mutations that confer resistance to CSF1R antagonists, but which do not concurrently induce constitutively active or suppressed CSF1R signaling. A pool of iPSC or monocyte cell lines will be generated that carry random mutations in the CSF1R gene. This pool will then be differentiated into microglia and the survival of cells monitored in response to either CSF1/IL-34 withdrawal or CSF1R antagonist treatments. Cells that survive for longer under these conditions will be examined via PCR and sequencing to identify CSF1R mutations that may confer resistance to CSF1R antagonists. Counter screens will then be performed to identify those CSF1R mutations that do not also lead to hyperproliferation or significant loss in proliferation. Once optimal mutations are identified iPSC lines carrying these mutations will be expanded and microglia derived from these lines will be examined in vivo in chimeric models to determine resistance to CSF1R antagonists in vivo.

Resistance to each of the CSF1R inhibitors tested was quantified using a fluorogenic caspase 3/7 detector (Essen BioScience) and time-lapse imaging over 24 hours. WT microglia exhibited significant levels of increased caspase to increasing concentrations of PLX3397 (MedChemExpress), PLX5622 (MedChemExpress), Edicotinib, and BLZ945, as compared to DMSO control treatment over 24 hours of imaging, signifying an increased cell death response to inhibiting the macrophage-colony stimulating factor/colony-stimulating factor 1 receptor (CSF1R). On the other hand, G795A and G795C iPSC-microglia exhibited no significant increase in caspase levels to increasing concentrations of either PLX3397, PLX5622, Edicotinib, or BLZ945, as compared to DMSO control treatment. These results indicate an acquired resistance to PLX treatment as a result of the genetically modified CSF1 receptor (see FIGS. 4A, 4B, 4C, 4D, and 4E).

Cell death assay: iPS-microglia were plated at 70K cells per 96-well plate (6 wells per line per condition). At time 0, all microglia were treated with IncuCyte Caspase-3/7 Green Apoptosis Assay Reagent 1:1000. Cells were maintained in the described medium: fresh complete medium+0.1% DMSO, complete media+250 nM PLX3397, complete medium+500 nM PLX3397, complete medium+1 μm PLX3397, complete medium+250 nM PLX5622, complete medium+500 nM PLX5622, complete medium+1 μm PLX5622, complete medium+250 nM Edicotinib, complete medium+500 nM Edicotinib, complete medium+1 μm Edicotinib, complete medium+250 nM BLZ945, complete medium+500 nM BLZ945, complete medium+1 μm BLZ945. Four 20× images per well were collected every hour for 24 hours. Using IncuCyte 2020B software, image masks for phase confluence (visually gated out apoptotic cells) as well as caspase 3/7 signal (green) were generated. Graphs display caspase normalized to phase confluence, completed with 3 lines: WT, G795A, G795C (see FIGS. 4A, 4B, 4C, 4D, and 4E).

EMBODIMENTS

The following embodiments are intended to be illustrative only and not to be limiting in any way.

Embodiment 1: A modified human cell exhibiting differential resistance to a CSF1R antagonist.

Embodiment 2: The cell of embodiment 1, comprising a nucleic acid encoding a modified CSF1R protein exhibiting differential resistance to a CSF1R antagonist.

Embodiment 3: A modified human cell comprising a nucleic acid encoding a modified CSF1R protein exhibiting differential resistance to a CSF1R antagonist.

Embodiment 4: The cell of any one of embodiments 1-3, comprising one or more genetic modifications in the CSF1R protein.

Embodiment 5: The cell of embodiment 4, wherein the one or more genetic modifications results in a change in the amino acid sequence of CSF1R, the change optionally comprising the substitution of an amino acid residue selected from G795, L785, M637, E633, and V647.

Embodiment 6: The cell of any one of embodiments 1-5, wherein the one or more genetic modifications results in a modified ATP binding pocket.

Embodiment 7: The cell of embodiment 6, wherein the modified ATP binding pocket has reduced binding space.

Embodiment 8: The cell of embodiment 7, wherein the modified ATP binding pocket cannot bind a CSF1R antagonist.

Embodiment 9: The cell of embodiment 6, wherein the modified ATP binding pocket can bind ATP.

Embodiment 10: The cell of any one of embodiments 1-9, wherein the one or more genetic modifications in the CSF1R protein do not interfere with ATP binding activity of the CSF1R protein.

Embodiment 11: The cell of any one of embodiments 1-10, wherein the one or more genetic modifications in the CSF1R protein do not induce constitutively active CSF1R signaling.

Embodiment 12: The cell of embodiment 11, wherein the modified CSF1R protein is activated by a CSF1 ligand.

Embodiment 13: The cell of embodiment 12, wherein the CSF1 ligand induces phosphorylation of the modified CSF1R protein.

Embodiment 14: The cell of embodiment 11, wherein the modified CSF1R protein is activated by an IL-34 ligand.

Embodiment 15: The cell of embodiment 14, wherein the IL-34 ligand induces phosphorylation of the modified CSF1R protein.

Embodiment 16: The cell of embodiment 4, wherein the one or more genetic modifications are introduced ex vivo.

Embodiment 17: The cell of embodiment 4, wherein the one or more genetic modifications are induced by transfecting or introducing into the cell a nucleic acid encoding a transgene, or by transduction or introduction of a targeted nuclease, nickase or base-editing effector or ribonucleoprotein complex.

Embodiment 18: The cell of embodiment 17, wherein introducing the nucleic acid encoding a transgene in a cell comprises contacting the cell with a viral vector.

Embodiment 19: The cell of any one of embodiments 1-18, wherein the cell comprising a modified CSF1R protein retains a gene expression profile of a cell comprising a wild-type CSF1R protein.

Embodiment 20: The cell of any one of embodiments 1-19, further comprising one or more modifications in another gene.

Embodiment 21: A modified human cell according to any one of embodiments 1-20 that is expressing CSF1R.

Embodiment 22: The cell of embodiment 21, wherein the cell is induced and differentiated to express CSF1R and is selected from a group consisting of pluripotent stem cell, hematopoietic stem cell, an erythromyeloid progenitor, and hematopoietic progenitor cell.

Embodiment 23: The cell of embodiment 22, wherein the cell is a CSF1R-expressing cell and is selected from a group consisting of microglia, macrophages, monocytes, or other phagocytes.

Embodiment 24: A composition comprising a CSF1R-expressing cell according to any one of embodiments 20-23.

Embodiment 25: The composition of embodiment 24, wherein the CSF1R-expressing cell is a CSF1R-expressing cell.

Embodiment 26: The composition of embodiment 25, comprising a plurality of cells, wherein at least 0.1%, 1%, 5%, 10%, 20%, 30%, 40%, 50%, 60%, 70%, 80%, 90%, 95%, or 99% of the cells are CSF1R expressing cells having differential resistance to a CSF1R antagonist.

Embodiment 27: A method of treating a subject, the method comprising: (a) administering a CSF1R antagonist to the subject in a quantity sufficient to inhibit a CSF1R signal in a cell of the subject; and (b) contacting the subject with a modified CSF1R-expressing cell having a differential resistance to the CSF1R antagonist.

Embodiment 28: A method of treating a subject, the method comprising: (a) contacting the subject with a modified CSF1R-expressing cell having a differential resistance to a CSF1R antagonist; and (b) administering the CSF1R antagonist to the subject in a quantity sufficient to inhibit a CSF1R signal in a cell of the subject.

Embodiment 29: The method of embodiment 27 and embodiment 28, wherein the CSF1R-expressing cell is a CSF1R-expressing cell.

Embodiment 30: The method of any one of embodiments 27-29, wherein the differential resistance to the CSF1R antagonist is partial resistance or complete resistance to the CSF1R antagonist.

Embodiment 31: The method of any one of embodiments 27-30, wherein the modified CSF1R-expressing cell retains a gene expression profile of a wild-type CSF1R-expressing cell.

Embodiment 32: The method of any one of embodiments 27-31, wherein the modified CSF1R-expressing cell expresses a gene product or other genetic modification useful to treat, cure, ameliorate, prevent or palliate a neurological disease.

Embodiment 33: The method of embodiment 32, wherein the gene product is a transgene that is not otherwise expressed by the CSF1R-expressing cell.

Embodiment 34: The method of embodiment 33, wherein the CSF1R signal that is inhibited by the CSF1R antagonist is proliferation or survival of a CSF1R-expressing cell that is endogenous to the subject.

Embodiment 35: The method of any one of embodiments 27-34, wherein the CSF1R antagonist is administered to the subject in a quantity sufficient to reduce the proliferation and/or survival of the endogenous CSF1R-expressing cell relative to the modified CSF1R-expressing cell.

Embodiment 36: A method of treating a subject, the method comprising: (a) contacting the subject with a modified CSF1R-expressing cell, and (b) differentially altering the proliferation or survival of an unmodified CSF1R-expressing cell relative to the modified CSF1R-expressing cell.

Embodiment 37: The method of embodiment 36, wherein the modified CSF1R-expressing cell is a CSF1R-expressing phagocyte.

Embodiment 38: The method of embodiment 36 and embodiment 37, wherein the modified CSF1R-expressing cell is partially resistant to a CSF1R antagonist.

Embodiment 39: The method of embodiment 36, wherein the step of differentially altering the proliferation or survival of the unmodified CSF1R-expressing cell comprising administering the CSF1R antagonist to the subject in a quantity sufficient to reduce proliferation and/or survival of the unmodified CSF1R-expressing cell relative to the modified CSF1R-expressing cell.

Embodiment 40: A nucleic acid composition encoding a modified CSF1R protein exhibiting differential resistance to a CSF1R antagonist.

Embodiment 41: The composition of embodiment 40, wherein the differential resistance to the CSF1R antagonist is partial resistance or complete resistance to the CSF1R antagonist.

Embodiment 42: The composition of embodiment 40, wherein the differential resistance to the CSF1R antagonist is an increased resistance to the CSF1R antagonist.

Embodiment 43: The composition of embodiment 40, wherein the differential resistance to the CSF1R antagonist is a decreased resistance to the CSF1R antagonist.

Embodiment 44: The composition of any one embodiments 40-43, wherein the modified CSF1R protein comprises one or more genetic modifications.

Embodiment 45: The composition of embodiment 44, wherein the one or more genetic modifications results in a change in the amino acid sequence of CSF1R, the change optionally comprising the substitution of an amino acid residue selected from G795, L785, M637, E633, and V647.

Embodiment 46: The composition of embodiment 44, wherein the one or more genetic modifications results in a modified ATP binding pocket.

Embodiment 47: The composition of embodiment 46, wherein the modified ATP binding pocket has reduced binding space.

Embodiment 48: The composition of embodiment 47, wherein the modified ATP binding pocket cannot bind a CSF1R antagonist.

Embodiment 49: The composition of embodiment 46, wherein the modified ATP binding pocket can bind ATP.

Embodiment 50: The composition of embodiment 44, wherein the one or more genetic modifications in the CSF1R protein do not interfere with ATP binding activity of the CSF1R protein.

Embodiment 51: The composition of embodiment 44, wherein the one or more genetic modifications in the CSF1R protein do not induce constitutively active CSF1R signaling.

Embodiment 52: The composition of embodiment 51, wherein the modified CSF1R protein is activated by a CSF1 ligand.

Embodiment 53: The composition of embodiment 52, wherein the CSF1 ligand induces phosphorylation of the modified CSF1R protein.

Embodiment 54: The composition of embodiment 51, wherein the modified CSF1R protein is activated by an IL-34 ligand.

Embodiment 55: The cell of embodiment 54, wherein the IL-34 ligand induces phosphorylation of the modified CSF1R protein.

Embodiment 56: An expression vector comprising the nucleic acid composition of any one of embodiments 40-55 operably linked to an expression control sequence.

Embodiment 57: A cultured cell transfected with the vector of embodiment 56, or a progeny of said cell, wherein the cultured cells express the polypeptide.

Embodiment 58: An endogenous cell infected with the vector of embodiment 56, wherein the endogenous cells express the polypeptide.

As used herein, the term "about" refers to plus or minus 20% of the referenced number.

Although there has been shown and described the preferred embodiment of the present disclosure, it will be readily apparent to those skilled in the art that modifications may be made thereto which do not exceed the scope of the appended claims. Therefore, the scope of the disclosure is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the disclosure described herein using the phrase "comprising" includes embodiments that could be described as "consisting essentially of" or "consisting of", and as such the written description requirement for claiming one or more embodiments of the present disclosure using the phrase "consisting essentially of" or "consisting of" is met.

What is claimed is:

1. An isolated and modified human induced pluripotent stem cell (iPSC)-derived microglial cell comprising a polynucleotide comprising a nucleic acid sequence encoding a modified CSF1R protein that comprises a glycine-to-cysteine amino acid substitution at an amino acid residue corresponding to glycine 795 (G795C) of SEQ ID NO: 2, wherein the modified CSF1R protein:
   (i) binds to ATP;
   (ii) is activated by a CSF1R ligand that induces phosphorylation of the modified CSF1R protein; and
   (iii) has a reduced sensitivity to a CSF1R inhibitor compared to a CSF1R protein consisting of the amino acid sequence of SEQ ID NO: 2.

2. The isolated and modified human induced pluripotent stem cell (iPSC)-derived microglial cell of claim 1, further comprising a transgene that expresses a protein that is not the modified CSF1R protein that comprises the glycine-to-cysteine amino acid substitution at the amino acid residue corresponding to glycine 795 (G795C) of SEQ ID NO: 2.

3. The isolated and modified human induced pluripotent stem cell (iPSC)-derived microglial cell of claim 1, wherein an in vitro cell population comprises a plurality of cells, wherein at least 20% of the plurality of cells are the isolated and modified human induced pluripotent stem cell (iPSC)-derived microglial cell.

4. The isolated and modified human induced pluripotent stem cell (iPSC)-derived microglial cell of claim 1, wherein the isolated and modified human induced pluripotent stem cell (iPSC)-derived microglial cell has a higher expression level of SLC30A8 compared to an isolated and modified human induced pluripotent stem cell (iPSC)-derived microglial cell that does not express the modified CSF1R protein that comprises the glycine-to-cysteine amino acid substitution at the amino acid residue corresponding to glycine 795 (G795C) of SEQ ID NO: 2.

5. The isolated and modified human induced pluripotent stem cell (iPSC)-derived microglial cell of claim 1, wherein the isolated and modified human induced pluripotent stem cell (iPSC)-derived microglial cell has a lower expression level of AC023794.5, IGKC, C5orf63, AL133216.2, or AC006453.2 compared to an isolated and modified human induced pluripotent stem cell (iPSC)-derived microglial cell that does not express the modified CSF1R protein that comprises the glycine-to-cysteine amino acid substitution at the amino acid residue corresponding to glycine 795 (G795C) of SEQ ID NO: 2.

6. The isolated and modified human induced pluripotent stem cell (iPSC)-derived microglial cell of claim 1, wherein, compared to an isolated and modified human induced pluripotent stem cell (iPSC)-derived microglial cell that does not express the modified CSF1R protein that comprises the glycine-to-cysteine amino acid substitution at the amino acid residue corresponding to glycine 795 (G795C) of SEQ ID NO: 2, the isolated and modified human induced pluripotent stem cell (iPSC)-derived microglial cell has a modified expression level of SLC30A8, AC023794.5, IGKC, C5orf63, AL133216.2, or AC006453.2.

7. The isolated and modified human induced pluripotent stem cell (iPSC)-derived microglial cell of claim 1, wherein the CSF1R inhibitor is selected from the group consisting of: PLX5622, PLX3397 (pexidartinib), BLZ945, Ki20227, JNJ-40346527(Edicotinib), cFMS Receptor Inhibitor II, AZ304, ARRY-382, YM-90709, GW2580, PLX108-01, PLX7486, PLX647, Emactuzumab (RG7155), AMG820, IMC-CS4 (LY3022855), MCS110, BPR1R024, AZD7507, JTE-952, JNJ-28312141, c-FMS-IN-8, CSF1R-IN-22, and any combinations thereof.

8. The isolated and modified human induced pluripotent stem cell (iPSC)-derived microglial cell of claim 1, wherein the isolated and modified human induced pluripotent stem cell (iPSC)-derived microglial cell is capable of engraftment into a brain of a subject.

9. The isolated and modified human induced pluripotent stem cell (iPSC)-derived microglial cell of claim 8, wherein, subsequent to engraftment of the isolated and modified human induced pluripotent stem cell (iPSC)-derived microglial cell in the brain of the subject, the isolated and modified human induced pluripotent stem cell (iPSC)-derived microglial cell makes up at least about 5% of microglial cells in the brain of the subject.

10. The isolated and modified human induced pluripotent stem cell (iPSC)-derived microglial cell of claim 9, wherein, subsequent to engraftment of the isolated and modified human induced pluripotent stem cell (iPSC)-derived microglial cell in the brain of the subject, the isolated and modified human induced pluripotent stem cell (iPSC)-derived microglial cell makes up at least about 20% of microglial cells in the brain of the subject.

11. The isolated and modified human induced pluripotent stem cell (iPSC)-derived microglial cell of claim 10, wherein, at least 10 days subsequent to engraftment of the isolated and modified human induced pluripotent stem cell (iPSC)-derived microglial cell in the brain of the subject, the isolated and modified human induced pluripotent stem cell (iPSC)-derived microglial cell makes up at least about 25% of microglial cells in the brain of the subject.

12. The isolated and modified human induced pluripotent stem cell (iPSC)-derived microglial cell of claim 11, wherein, subsequent to engraftment of the isolated and modified human induced pluripotent stem cell (iPSC)-derived microglial cell in the brain of the subject, the isolated and modified human induced pluripotent stem cell (iPSC)-derived microglial cell makes up at least about 70% of microglial cells in the brain of the subject.

13. A method comprising administering the isolated and modified human induced pluripotent stem cell (iPSC)-derived microglial cell of claim 1 to a subject.

14. The isolated and modified human induced pluripotent stem cell (iPSC)-derived microglial cell of claim 9, wherein, after at least 10 days subsequent to engraftment of the isolated and modified human induced pluripotent stem cell (iPSC)-derived microglial cell in the brain of the subject, the isolated and modified human induced pluripotent stem cell (iPSC)-derived microglial cell makes up at least about 25% of microglial cells in the brain of the subject.

15. The isolated and modified human induced pluripotent stem cell (iPSC)-derived microglial cell of claim 1, wherein the isolated and modified human induced pluripotent stem cell (iPSC)-derived microglial cell has complete resistance to inhibition by the CSF1R inhibitor.

16. The isolated and modified human induced pluripotent stem cell (iPSC)-derived microglial cell of claim 15, wherein the CSF1R inhibitor is PLX3397 (pexidartinib).

17. The isolated and modified human induced pluripotent stem cell (iPSC)-derived microglial cell of claim 7, wherein the CSF1R inhibitor is present at a concentration of at least about 250 nanomolar (nM).

18. The isolated and modified human induced pluripotent stem cell (iPSC)-derived microglial cell of claim 1, wherein the polynucleotide comprises a nucleic acid sequence encoding a modified human CSF1R protein having the amino acid sequence of SEQ ID NO: 6,
   wherein the isolated and modified human induced pluripotent stem cell (iPSC)-derived microglial cell has a reduced sensitivity to treatment of the CSF1R inhibitor compared to an isolated and modified human induced pluripotent stem cell (iPSC)-derived microglial cell that does not express the modified human CSF1R protein having the amino acid sequence of SEQ ID NO: 6; and wherein the CSF1R inhibitor is PLX3397.

19. The isolated and modified human induced pluripotent stem cell (iPSC)-derived microglial cell of claim 18, wherein the isolated and modified human induced pluripotent stem cell (iPSC)-derived microglial cell has complete resistance to exposure to PLX3397 at a concentration of at least about 250 nanomolar (nM).

20. The isolated and modified human induced pluripotent stem cell (iPSC)-derived microglial cell of claim 19, wherein the isolated and modified human induced pluripotent stem cell (iPSC)-derived microglial cell has complete resistance to exposure to PLX3397 at a concentration of at least about 250 nanomolar (nM) to about 1 micromolar (1 µM).

21. The isolated and modified human induced pluripotent stem cell (iPSC)-derived microglial cell of claim 18, wherein the isolated and modified human induced pluripotent stem cell (iPSC)-derived microglial cell has:
   a) at least about a 2-fold higher expression level of SLC30A8, and
   b) at most about 50% of the expression level of AC023794.5, IGKC, C5orf63, AL133216.2, or AC006453.2
   compared to an isolated and modified human induced pluripotent stem cell (iPSC)-derived microglial cell that does not express the modified human CSF1R protein having the amino acid sequence of SEQ ID NO: 6.

22. The isolated and modified human induced pluripotent stem cell (iPSC)-derived microglial cell of claim 18, wherein, at least 30 days subsequent to engraftment in a brain of a subject and at least 10 days subsequent to administration of the CSF1R inhibitor to the subject, a plurality of isolated and modified human induced pluripotent stem cell (iPSC)-derived microglial cells in the brain of the subject make up at least about 70% of microglial cells in the brain of the subject.

23. A method comprising administering the isolated and modified human induced pluripotent stem cell (iPSC)-derived microglial cell of claim 18 to a subject.

24. The method of claim 18, wherein the isolated and modified human induced pluripotent stem cell (iPSC)-derived microglial cell engrafts for at least 10 days in the brain of the subject.

* * * * *